(12) United States Patent
Kobori et al.

(10) Patent No.: US 6,340,697 B1
(45) Date of Patent: Jan. 22, 2002

(54) OXIME DERIVATIVES AND AGRICULTURAL CHEMICALS CONTAINING THE SAME

(75) Inventors: Takeo Kobori, Atsugi; Tomoko Goto, Sakura; Hitoshi Kondo, Chiba; Hiroyuki Tsuboi, Yachiyo; Mika Iiyama, Sakura; Toru Asada, Inba-gun; Takashi Goto, Sakura, all of (JP)

(73) Assignee: Dainippon Ink and Chemicals, Inc., Tokyo (JP)

( * ) Notice: Subject to any disclaimer, the term of this patent is extended or adjusted under 35 U.S.C. 154(b) by 0 days.

(21) Appl. No.: 09/581,288

(22) PCT Filed: Dec. 9, 1998

(86) PCT No.: PCT/JP98/05558

§ 371 Date: Jun. 12, 2000

§ 102(e) Date: Jun. 12, 2000

(87) PCT Pub. No.: WO99/29689

PCT Pub. Date: Jun. 17, 1999

(30) Foreign Application Priority Data

Dec. 10, 1997 (JP) .............................................. 9-339790

(51) Int. Cl.$^7$ ........................ C07D 417/12; A01N 43/82
(52) U.S. Cl. ........................ 514/364; 514/340; 514/342; 514/361; 514/362; 546/177; 546/277; 548/125; 548/127; 548/134
(58) Field of Search ................................. 548/127, 134, 548/125; 546/277, 177; 511/364, 362, 361, 340, 342

(56) References Cited

FOREIGN PATENT DOCUMENTS

JP          07252242     * 10/1995   .................. 548/125

* cited by examiner

Primary Examiner—Robert Gerstl
(74) Attorney, Agent, or Firm—Armstrong, Westerman, Hattori, McLeland & Naughton, LLP

(57) ABSTRACT

Various oxime derivatives are provided, which do not cause any chemical damage to plants and which exhibit sufficient effectiveness against various plant diseases. The oxime derivatives are expressed by two general chemical formulas (1) and (2), as follows.

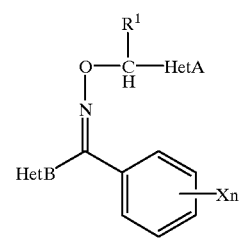

(1)

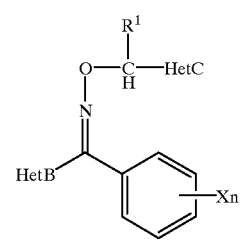

(2)

Agricultural chemicals and plant disease control chemicals are also provided which contain the above mentioned oxime derivatives as active ingredients. Test results of these agricultural chemicals and the plant disease control chemicals are proved to be very effective for downey mildews and late blights or Phytophthora rot etc.

14 Claims, No Drawings

OXIME DERIVATIVES AND AGRICULTURAL CHEMICALS CONTAINING THE SAME

TECHNICAL FIELD

This invention relates to novel oxime derivatives and agricultural chemicals including the oxime derivatives as active ingredients and, particularly relates to control chemicals for plant diseases.

BACKGROUND ART

Regarding oxime derivatives which are effective as agricultural chemicals or pesticides, Japanese Patent Application, First Publication No. Hei 7-25224 by the present inventors discloses, for example, that 4, 5-substituted-1, 2, 3-thiadiazole derivatives are effective as control chemicals for plant diseases.

Although the above derivatives are effective as control chemicals, it is desired to develop new agricultural chemicals which are superior in effects in a lesser amount than the above thiadiazole derivatives.

DISCLOSURE OF INVENTION

The problems to be solved by the present invention are, therefore, to provide a new oxime derivative which is sufficiently effective to treat plant diseases in small amounts without causing damage or phytotoxicity to the plant and agricultural chemicals or pesticides containing the above mentioned oxime derivative as an active ingredients, particularly, as the control chemicals for plant diseases.

The inventors of the present invention have synthesized new oxime derivatives and have investigated bioactivities of these derivatives in order to solve the above problems. After a series of investigations, this invention was completed by discovering that oxime derivatives represented by general chemical formulas (1) and (2) are particularly effective, showing superior bioactivity against various bacteria causing plant diseases, and without showing any phytotoxicity.

The present invention provides the following oxime derivatives and agricultural chemicals containing said oxime derivatives as effective agents:

(1) an oxime derivative represented by the following general chemical formula (1),

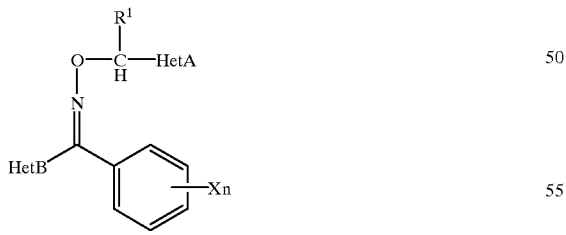

(1)

wherein,
$R^1$ represents a hydrogen atom or a lower alkyl group; X represents a halogen atom, a nitro group, a hydroxyl group, a cyano group, a carboxyl group, an alkoxy-carbonyl group, a lower alkyl group which may be substituted with halogen atoms; a lower alkoxy group which may be substituted with halogen atoms; a lower alkylthio group which may be substituted with halogen atoms; a lower alkylsulfonyl group which may be substituted with a halogen atom; an aryl group which may be substituted with a halogen atom or a lower alkyl group; an aryloxy group which may be substituted with a halogen atom or a lower alkyl group; or an amino group which may be substituted with a lower alkyl group; and n represents an integer from 0 to 3; and Het A represents a 6-membered aromatic nitrogen-containing ring which contains one or two nitrogen atoms or its benzo-condensation ring-type nitrogen containing aromatic ring which may be substituted with one or two substitutable groups selected from the group consisting of a halogen atom, a lower alkyl group, a lower alkylthio group, a lower alkylsulfonyl group, a lower alkoxy group, a trifluoromethyl group, and a cyano group; and Het B represents oxime derivatives, each ring structure, expressed by the following formulas,

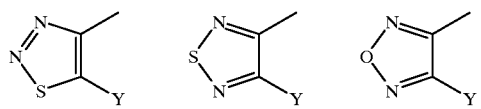

wherein,
Y represents a hydrogen atom, a halogen atom, or a lower alkyl group which may be substituted with a halogen atom;

(2) an oxime derivative expressed by the following general chemical formula (2);

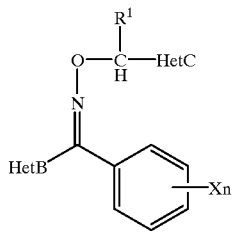

(2)

[wherein,
$R^1$, X, n, Het B, and Y are the same as those defined in the chemical formula (1), and Het C represents a 5-membered nitrogen containing aromatic ring or its benzo-condensation ring-type nitrogen containing aromatic ring which contains more than one nitrogen atom, or which may contain a sulfur atom or an oxygen atom, and which may be substituted with more than one substituting group, and the substitutable groups on a nitrogen atom of said 5-membered nitrogen containing aromatic ring are groups selected from the group consisting of a lower alkyl group, a lower alkyl-sulfonyl group, triphenylmethyl group, a lower alkoxymethyl group and a N, N-di-substituted sulfamoyl group substituted with lower alkyl groups, and the substitutable groups on a carbon atom of said 5 membered nitrogen containing aromatic ring are groups selected from the group consisting of a halogen atom, a cyano group, an alkyl group ranging from $C_1$ to $C_6$ which may be substituted with a halogen atom, and a cycloalkyl group ranging from $C_3$ to $C_6$; and
an alkenyl group ranging from $C_2$ to $C_6$, an alkinyl group ranging from $C_2$ to $C_6$, an alkoxy group ranging from $C_1$ to $C_5$ which may be substituted with a halogen atom, a lower alkylthio group which may be substituted with a halogen atom, a lower alkylsulfonyl group which may be substituted with a halogen atom, a lower alkyl sulfinyl group which may be substituted with halogen atoms, an amino group which may be substituted with a lower alkyl group or a cycloalkyl group ranging from $C_3$ to $C_6$ or a triphenyl-methyl group; and a lower alkoxy-carbonyl group, a carbamoyl group which may be substituted with lower alkyl groups, an aminomethyl group which may be substituted with lower alkyl groups, an acylaminomethyl group, N-alkoxycarbonyl-aminomethyl group, an alkyl thiomethyl group, aryl group which may be substituted with halogen atoms, and a heteroaryl group which may be substituted with halogen atoms, and a group expressed by —N ($R^2$) C (=O) $R^3$ (wherein, $R^2$ represents a hydrogen atom or a methyl group, and R represents a hydrogen atom, an alkyl group ranging from $C_1$ to $C_{10}$ which may be substituted with halogen atoms, a cycloalkyl group ranging from $C_3$ to $C_8$, an alkenyl group ranging from $C_2$ to $C_6$, an alkinyl atoms ranging from $C_2$ to $C_4$, an aralkyl group, a lower alkyl group substituted with an amino group, an aralkyl group substituted with an amino group, a lower alkyl group substituted with an acylamino group, an aralkyl group substituted with an acylamino group, a lower alkyl group substituted with an alkoxy-carbonyl-amino group, an aralkyl group substituted with an alkoxy-carbonyl-amino group, an aryl group which may be substituted with halogen atoms, lower alkyl groups which may be substituted with halogen atoms, lower alkoxy groups, lower alkylthio groups, amino groups, nitro groups or cyano groups, a heteroaryl group, a lower alkoxy group, a cycloalkyloxy group ranging from $C_3$ to $C_6$, a benzyloxy group and an aryloxy group)], (3) an oxime derivative expressed by the chemical formula (1), wherein Het A is a pyridyl group which may be substituted with one halogen atom or a lower alkyl group;

(4) an oxime derivative expressed by the chemical formula (2), wherein the Het C is a thiazolyl group which is expressed by the following chemical formula,

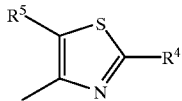

[wherein, $R^4$ represents a hydrogen atom, an amino group, an alkoxy group ranging from $C_1$ to $C_5$ which may be substituted with halogen atoms, a lower alkylthio group which may be substituted with halogen atoms, a lower alkylsulfonyl group which may be substituted with halogen atoms, a lower alkylsulfinyl group which may be substituted with halogen atoms; or a —NHC (=O) $R^3$ group (wherein, $R^3$ represents a hydrogen atom, an alkyl group ranging from $C_1$ to $C_{10}$ which may be substituted with halogen atoms, a cycloalkyl group ranging from $C_3$ to $C_8$, an alkenyl group ranging from $C_2$ to $C_6$, an alkinyl group ranging from $C_2$ to $C_4$, an aralkyl group, a lower alkyl group substituted with an amino group, an aralkyl group substituted with an amino group, a lower alkyl group substituted with an acylamino group, an aralkyl group substituted with an acylamino group, a lower alkyl group substituted with an alkoxycarbonylamino group, an aralkyl group substituted with an alkoxycarbonylamino group; an aryl group which may be substituted with halogen atoms, lower alkyl groups which may be substituted with halogen atoms, lower alkoxy groups, lower alkylthio groups, amino groups, nitro groups, or cyano groups; a heteroaryl group, a lower alkoxy group, or a cycloalkyloxy group ranging from $C_3$ to $C_6$, a benzyl oxy group, or a aryloxy group); and $R^5$ represents a hydrogen atom, a halogen atom, or a lower alkyl group which may be substituted with a halogen atom];

(5) the oxime derivative recited in the above (4), in which $R^4$ is a group expressed by —NHC (=O) $R^3$ (wherein, $R^3$ represents a hydrogen atom, an alkyl group ranging from $C_1$ to $C_6$ which may be substituted with halogen atoms, a lower cycloalkyl group ranging from $C_3$ to $C_6$, an aryl group which may be substituted with halogen atoms, lower alkyl groups which may be substituted with halogen atoms, lower alkoxy groups, amino groups, or cyano groups; a heteroaryl group, or a lower alkoxy group), and $R^5$ is a hydrogen atom;

(6) a pesticide which contains at least one of the oxime derivatives of the above components recited in (1) to (5) as active ingredient;

(7) a plant disease control agent which contains at least one of the oxime derivatives of the above components recited in (1) to (5) as active ingredient;

(8) a plant disease control agent as recited in (7), which is effective for plant diseases caused by mold fungi.

BEST MODE FOR CARRYING OUT THE INVENTION

In the oxime derivatives expressed by the general chemical formulas (1) and (2), $R^1$ represents a hydrogen atom or a lower alkyl group. The structure of the lower alkyl group may be linear or branched, and examples of the lower alkyl group include, for example, a methyl group, an ethyl group, a n-propyl group, an isopropyl group, a n-butyl group, an isobutyl group, a sec-butyl group, and a cyclopropyl group, all of which range from $C_1$ to $C_4$. Particularly preferable groups are a hydrogen atom and a methyl group.

In the general formulas (1) and (2), X represents halogen atoms, a nitro group, a hydroxyl group, a cyano group, a carboxyl group, an alkoxycarbonyl group, a lower alkyl group which may be substituted with halogen atoms, a lower alkoxy group which may be substituted with halogen atoms, an alkylthio group which may be substituted with halogen atoms, a lower alkylsulfonyl group which may be substituted with halogen atoms, an aryl group which may be substituted with halogen atoms or lower alkyl groups, an aryloxy group which may be substituted with halogen atoms or lower alkyl groups, or an amino group which may be substituted with lower alkyl groups.

Here, examples of the halogen atoms include a chlorine atom, a bromine atom, a iodine atom, and a fluorine atom; and examples of the alkoxycarbonyl group include a methoxycarbonyl group, a ethoxycarbonyl group, and a n-propylcarbonyl group; examples of the lower alkyl groups which may be substituted with halogen atoms include linear or branched lower alkyl groups ranging from $C_1$ to $C_4$ such as a methyl group, an ethyl group, a n-propyl group, an isopropyl group, a n-propyl group, a n-butyl group, an isobutyl group, a sec-butyl group, a tert-butyl group, lower halogen-substituted alkyl groups such as a chloromethyl group, a difluoromthyl group, a trifluoromethyl group, a difluorochloromethyl group, a pentafluoroethyl group, 3. 3. 3-trifluoro-n-propyl group.

Examples of lower alkoxy groups which may be substituted with halogen atoms include a methoxy group, an ethoxy group, a n-propoxy group, an isopropoxy group, a n-butoxy group, an isobutoxy group, a sec-butoxy group, a tert-butoxy group, a cyclopropyloxy group, a difluromethoxy group; and examples of lower alkylthio groups which may be substituted with halogen atoms include a methylthio group, an ethylthio group, a n-propylthio group, an isopropylthio group, an n-butylthio group, an isobutylthio group, a sec-butylthio group, a difluoromethylthio group, a trifluoromethylthio group, and a cyclopropylthio group.

Examples of lower alkylsulfonyl groups which may be substituted with halogen atoms include methanesulfonyl group, a ethanesulfonyl group, a n-propanesulfonyl group, an isopropanesulfonyl group, a n-butanesulfonyl group, a difluoromethanesulfonyl group, and a trifluoromethanesulfonyl group. Examples of aryl groups which may be substituted with halogen atoms or lower alkyl groups include a phenyl group, a 4-chlorophenyl group, a 4-tolyl group, and a 3-fluorophenyl group.

Examples of aryloxy groups which may be substituted with halogen atoms or lower alkyl groups include a phenoxy group and a 4-florophenoxy group; and examples of amino groups which may be substituted with lower alkyl groups include an amino group, a methylamino group, an ethylamino group, a n-propylamino group, an isoproylamino group, a n-butylamino group, an isobutylamino group, a sec-butylamino group, a tert-butylamino group, a dimethylamino group, a diethylamino group, a di-n-propylamino group, a di-n-butylamino group, an ethylmethylamino group, a methyl-n-propylamino group, an ethyl-n-propylamino group, an ethyl-n-propylamino group, and a cyclopropylamino group.

The substituting position of X is not limited, and n represents an integer ranging from 0 to 3. When n is 2 or 3, X may be identical or different. Preferable examples of X include a hydrogen atom, a lower alkyl group ranging from $C_1$ to $C_3$, a fluoroalkyl group ranging from $C_1$ to $C_2$, and a halogen atom, and the most preferable examples include a hydrogen atom, a trifluoromethyl group, a fluorine atom, and a chlorine atom.

The Het A in the general formula (1) represents a 6-membered nitrogen containing aromatic ring which contains 1 or 2 nitrogen atoms , or its benzo-condensation ring-type nitrogen-containing ring, which may be substituted with 1 or 2 substituting groups. Examples of the 6-membered nitrogen containing aromatic rings include a pyridine ring, a pyrimidine ring, a pyrazine ring, and a pyridazine ring; and examples of the benzo-condensation ring-type nitrogen containing aromatic rings include a quinoline ring, a quinazoline ring, and a quinoxaline ring.

Examples of substitutable groups on the Het A include a halogen atom, a lower alkyl group, a lower alkylthio group, a lower alkylsulfonyl group, a lower alkoxy group, a trifluoromethyl group and a cyano group, and, in more detail, the halogen atoms may include a chlorine atom, a bromine atom, a fluorine atom; the lower alkyl groups may include linear or branched lower alkyl groups such as a methyl group, an ethyl group, a n-propyl group, an isopropyl group, a n-butyl group, an isobutyl group, and a sec-butyl group; and examples of the lower alkylthio groups are linear or branched alkylthio groups such as a methylthio group, an ethylthio group, a n-propylthio group, an isopropylthio group, a n-butylthio goup, an isobutylthio group, and a sec-butylthio group.

Examples of the lower alkylsulfonyl groups include linear or branched alkylsulfonyl groups such as a methanesulfonyl group, an ethanesulfonyl group, a propanesulfonyl group, an isopropanesulfonyl group, a butanesulfonyl group, an isobutanesulfonyl group, and a sec-butanesulfonyl group; and examples of the lower alkoxy groups includes linear or branched lower alkoxy groups such as a methoxy group, an ethoxy group, a n-butoxy group, an isobutoxy group, and a sec-butoxy group.

A preferable example of the Het A is a pyridin-2-yl group, and the most preferable examples of the Het A include a pyridin-2-yl group or a 5-methylpyridin-2-yl group.

Het B in the general formulas (1) and (2) is expressed by the following formulas,

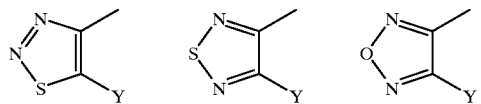

(wherein, Y represents a hydrogen atom, a halogen atom, and a lower alkyl group which may be substituted with a halogen atom), and wherein, Het B represents a 1, 2, 3-thiadiazol-4-yl group, a 1, 2, 5-thiadiazol-3-yl group, or 1, 2, 5-oxyadiazol-3-yl group or their halogenaged derivatives, or derivatives substituted with a lower alkyl group which is substituted with a halogen or not substituted.

Examples of the halogen atoms represented by Y include a fluorine atom, a chlorine atom, a bromine atom; and examples of the lower alkyl groups which may be substituted with halogen atoms include lower alkyl groups ranging from $C_1$ to $C_4$ such as a methyl group, an ethyl group, a n-propyl group, an isoropyl group, a difluoromethyl group, and a trifluoromethyl group, and the most preferable group is a methyl group.

Het C in the general formula (2) represents a 5-membered nitrogen containing aromatic ring or its benzo-condensation nitogen containing aromatic ring, which contains more than one nitrogen atom, which may contain a sulfur atom or a oxygen atom, and which may be substituted with more than one substituting group.

Examples of the 5-membered nitrogen containing aromatic rings include a pyrrole ring, a imidazole ring, a oxazole ring, a thiazole ring, a pyrazole ring, an isoxazole ring, an isothiazole ring, a 1, 2, 3-triazole ring, a 1, 2, 4-triazole ring, a 1, 2, 3-oxadiazole ring, a 1, 2, 4-oxadiazole ring, a 1, 2, 5-oxadiazole ring, a 1, 3, 4-oxadiazole ring, a 1, 2, 3-thiadiazole ring, a 1, 2, 4 thiadiazole ring, a 1, 3, 4 thiadiazole ring, 1, 2, 4 thiadiazole ring and a tetrazole ring; and examples of its benzo-condensation ring-type nitrogen containing aromatic rings include a benzimidazole ring, a benzoxazole, a benzthiazole, a imidazo [1, 2-a] pyridine ring, a [1, 2, 4] triazo [1, 5-a] pyridine ring.

Examples of the groups substitutable on the nitrogen atom of the Het C group include a lower alkyl group, a lower alkylsulfonyl group, a triphenylmethyl group, a lower alkoxymethyl group, and a N, N-di-substituted-sulfamoyl group substituted with lower alkyl groups, wherein examples of the lower alkyl groups include a methyl group, an ethyl group, a n-propyl group, an isopropyl group, a n-butyl group, an isobutyl group, and a sec-butyl group; and examples of lower alkylsulfonyl group include a methanesulfonyl group, an ethanesulfonyl group, a n-propanesulfonyl group, an isopropanesulfonyl group, a n-butanesulfonyl group, and an isobutanesulfonyl group; example of lower alkoxymethyl group include a methoxymethyl group and an ethoxymethyl group; examples of N,N-di-substituted sulfamoyl group substituted with lower alkyl groups include a dimethylsulfamoyl group and a diethylsulfamoyl group.

Examples of groups which are substitutable on the carbon atom of the Het C group include a halogen atom, a cyano group, an alkyl group ranging from $C_1$ to $C_6$ which may be substituted with halogen atoms, a cycloalkyl group ranging from $C_3$ to $C_6$, an alkenyl group ranging from $C_2$ to $C_6$, an alkynyl group ranging from $C_2$ to $C_6$, an alkoxy group ranging from $C_1$ to $C_5$ which may be substituted with halogen atoms, a lower alkylthio group which may be substituted with halogen atoms, a lower alkylsulfonyl group which may be substituted with halogen atoms, a lower alkylsulfinyl group which may be substituted with halogen atoms, and an amino group which may be substituted with lower alkyl groups or cycloalkyl groups ranging from $C_3$ to $C_6$ or triphenylmethyl groups; and a group expressed by a formula —N ($R^2$) C (=O) $R^3$ (wherein, $R^2$ represents a hydrogen atom or a methyl group and $R^1$ represents a hydrogen atom, an alkyl group ranging from $C_1$ to $C_{10}$ which may be substituted with halogen atoms, preferably from $C_1$ to $C_8$, a cycloalkyl group ranging from $C_3$ to $C_8$, preferably from $C_3$ to $C_6$, an alkenyl group ranging from $C_2$ to $C_6$, an aralkyl group, a lower alkyl group substituted with an amino group, an aralkyl group substituted with an amino group, a lower alkyl group substituted with an acylamino group, an aralkyl group substituted with an acylamino group, a lower alkyl group substituted with an alkoxycarbonylamino group, an aralkyl group substituted with an alkoxycarbonylamino group; and a halogen atom, and a lower alkyl group which may be substituted with halogen atoms, a lower alkoxy group, a lower alkylthio group, an amino group, an aryl group which may be substituted with a nitro group or a cyano group; a heteroaryl group, a lower alkoxy group, a cycloalkyloxy group, a benzyloxy group or a aryloxy group); and a lower alkoxycarbonyl group, a carbamoyl group which may be substituted with lower alkyl groups, an aminomethyl group which may be substituted with lower alkyl groups, an acylaminomethyl group, a N-alkoxycarbonylaminomethyl group, an alkylthioethyl group, and an aryl group or a heteroaryl group which may be substituted with halogen atoms.

More practically, examples of the halogen atoms include a chlorine atom, a fluorine atom, and a bromine atom; examples of the alkyl groups which may be substituted with halogen atoms include a methyl group, an ethyl group, a n-propyl group, an isopropyl group, a n-butyl group, an isobutyl group, a n-hexyl group, a difluoromethyl group, and a trifluoromethyl group; examples of the cycloalkyl groups ranging from $C_3$ to $C_6$ include a cyclopropyl group, a cyclopentyl group, and a cyclohexyl group; and examples of the alkenyl groups ranging from $C_2$ to $C_6$ include a vinyl group, an allyl group, a butenyl group, and a hexenyl group.

Examples of the alkynyl groups ranging from $C_2$ to $C_6$ include a ethynyl group, a propargyl group, and a butynyl group; and examples of the lower alkoxy groups ranging from $C_1$ to $C_5$ carbon atoms, which may be substituted with halogen atoms include a methoxy group, an ethoxy group, a n-propoxy group, an isopropoxy group, a n-butoxy group, an isobutoxy group, a sec-butoxy group, a n-pentyloxy group, a difluoromethoxy group, and a trifloromethoxy group.

Examples of lower alkylthio groups which may be substituted with halogen atoms include a methylthio group, an ethylthio group, a propylthio group, an isopropylthio group, a butylthio group, an isobutylthio group, a sec-butylthio group, a difluoromethylthio group, and a trifluoromethylthio group.

Examples of lower alkylsulfonyl groups which may be substituted with halogen groups include a methanesufonyl group, an ethanesulfonyl group, a propanesulfonyl group, an isopropanesulfonyl group, a butanesulfonyl group, a difluoromethanesulfonyl group, and a trifluoromethanesulfonyl group; and examples of lower alkylsulfinyl groups which may be substituted with halogen atoms include a difluoromethanesulfinyl group and a trifluoromethanesulfinyl group.

Examples of the amino groups which may be substituted with lower alkyl groups or cycloalkyl groups ranging from $C_3$ to $C_6$ include an amino group, a methylamino group, an ethylamino group, a propylamino group, an isopropylamino group, a butylamino group, an isobutylamino group, a sec-butylamino group, a dimethylamino group, a diethylamino group, a dipropylamino group, a dibutylamino group, an ethylmethylamino group, a methylpropylamino group, anethylpropylamino group, a cyclopropylamino group, a cyclopentylamino group, and a cyclohexylamino group.

Examples of the lower alkoxycarbonyl groups include a methoxycarbonyl group, an ethoxycarbonyl group, and a propoxycarbonyl group; examples of carbamoyl groups which may be substituted with lower alkyl groups include a N-methylcarbamoyl group, a N-ethylcarbamoyl group, a N-isopropylcarbamoyl group, and a N, N-diethylcarbamoyl group; and examples of the aminomethyl group which may be substituted with a lower alkyl groups include an aminomethyl group, a N-methylaminomethyl group, a N-ethylaminomethyl group, a N-propylaminomethyl group, a N-isopropylaminomethyl group, a N-butylaminomethyl group, a N,N-dimethylaminomethyl group, and a N,N-diethylaminomethyl group.

Examples of the acylaminomethyl groups include a formylaminomethyl group, an acetylaminomethyl group, a propionylaminomethyl group, a butyrylaminomethyl group, an isobutyrylaminomethyl group, a benzoylaminomethyl group, and a N-acetyl-N-isopropylaminomethyl group; examples of the N-alkoxycarbonylaminomethyl groups include a methoxycarbonylaminomethyl group, an ethoxycarbonylaminomethyl group, a t-butoxycarbonylaminomethyl group, and a N-(t-butoxycarbonyl)-N-isopropylaminomethyl group; and an example of the alkylthiomethyl group is a isopropylaminomethyl group.

Examples of the aryl groups which may be substituted with halogen atoms include a phenyl group, a 2-fluorophenyl group, a 3-fluorophenyl group, a 4-fluorophenyl group, a 2-chlorophenyl group, a 3-chlorophenyl group, a 4-chlorophenyl group, a 2, 4-dichlorophenyl group, a 3, 4-dichlorophenyl group, a 2, 6-dichlorophenyl group, a naphthyl group, and a biphenyl group; and examples of the heteroaryl groups include a pyridin-2-yl group, a pyridin-4-yl group, a pyridin-3-yl group, a 2-furyl group, a 3-furyl group, a 2-thienyl group, a 3-thienyl group, a quinoyl group, a indolyl group, a benzofuranyl group, a benzthienyl group, a benzthiazolyl group, a benzisoxazolyl group, and a benzisothiazolyl group.

Practical examples of the $R^3$ in the —N ($R^2$) C (=O) $R^3$ group have two groups, one of which is the alkyl groups which may be substituted with halogen atoms ranging from $C_1$ to $C_{10}$, preferably from $C_1$ to $C_8$, including a methyl group, an ethyl group, a n-propyl group, an isopropyl group, a t-butyl group, a n-butyl group, an isobutyl group, a sec-butyl group, a n-pentyl group, a 1-ethylpropyl group, a n-decyl group, a chloromethyl group, a trifluoromethyl group, a trichloromethyl group, a 1-bromoisopropyl group, a chlorodifluromethyl group, and 1-chloromethyl-1-methylethyl group; and another one of which is cycloalkyl groups ranging from $C_3$ to $C_8$, preferably from $C_3$ to $C_6$, including a cyclopropyl group, a cyclobutyl group, a cyclopentyl group, and a cyclo-octyl group.

Examples of alkenyl groups ranging from $C_2$ to $C_6$ include a vinyl group, an allyl group, a butenyl group, and a hexenyl group; examples of alkynyl groups ranging from $C_2$ to $C_4$ include an ethynyl group, a propargyl group, and a butynyl group; examples of the aralkyl groups include a benzyl group and a 2-phenylethyl group; the lower alkyl groups substituted with an amino group include aminomethyl group and a 1-aminoisobutyl group; example of aralkyl groups substituted with an amino group is a 1-amino-2-phenylethyl groups etc.; and examples of the lower alkyl groups substituted with an acylamino group include an acetylaminomethyl group and a 1-acetylaminoisobutyl group.

An example of an aralalkyl group substituted with an acylamino group is a 1-acetylamino-2-phenyl group; examples of lower alkyl groups substituted with an alkoxycarbonylamino group include a t-butoxycarbonylaminomethyl group and a 1-(t-butoxycarbonyl amino) isobutyl group; and an example of aralkyl group substituted with an alkoxycarbonylamino group is a 1-(benzyloxycarbonylamino)-2-phenylethyl group.

Examples of the aryl groups which may be substituted with halogen atoms, lower alkyl groups which may be substituted with halogen atoms, a lower alkylthio group, an amino group, a nitro group or a cyano group include a phenyl group, a 2-fluorophenyl group, a 3-fluorophenyl group, a 4-fluorophenyl group, a 2-chlorophenyl group, a 3-chlorophenyl group, a 4-chlorophenyl group, a 2, 4-dichlorophenyl group, a 3, 4-dichlorophenyl group, a 2, 6-dichlorophenyl group, a 4-methylphenyl group, a 2-methylphenyl group, a 2, 4-dimethylphenyl group, a 4-trifluoromethylphenyl group, a 2-methoxyphenyl group, a 3-methoxyphenyl group, a 4-methoxyphenyl group, a 2-methylthiophenyl group, a 4-aminophenyl group, a 4-acetylaminophenyl group, a 2-cyanophenyl group, a 3-cyanophenyl group, a 4-cyanophenyl group, a 4-nitrophenyl group, and a naphthyl group.

Examples of the heteroaryl groups include a 2-furyl group, a 2-thienyl group, a pyridin-4-yl group, a pyridin-2-yl group, a thiazol-4-yl group, an oxazol-4-yl group, a pyrazol-3-yl group, an imidazol-4-yl group, an isothiazol-5-yl group, an isoxyazol-5-yl group, a pyrazinyl group, a pyrimidin-2-yl group, a pyridazin-3-yl group, a (1, 2, 3-thiaziazol)-4-yl group, a (1, 2, 5-thiaziazol)-3-yl group, a furazanyl group, a benzothiazol-2-yl group, a benzothiazol-2-yl group, a benzoimidazol-2-yl group, a quinolin-2-yl group, an isoquinolin-2-yl group, and a quinoxalin-2-yl group.

Examples of the lower alkoxy groups include a methoxy group, an ethoxy group, a n-propoxy group, an isopropoxy group, a butoxy group, a t-butoxy group, and a 1-ethylpropoxy group; examples of the cycloalkyloxy groups ranging $C_3$ to $C_6$ include a cyclopropyloxy group, a cyclopentyloxy group, and a cyclohexyloxy group; and an example of the aryloxy group is a phenoxy group. The substituting groups which are substitutable with the nitrogen atom and the carbon atom on the Het C may be two or more.

Preferable examples of Het C are groups such as a thiazol-2-yl group which may be substituted, a thiazol-4-yl group which may be substituted, and a thiazol-4-yl group which may be substituted. The most preferable examples are groups such as a thiazol-2-yl group, a thiazol-4-yl group, a 2-aminothiazol-4-yl group, a 2-acylaminothiazol-4-yl group, a 2-alkoxycarbonylaminothiazol-4-yl group, a 2-alkoxythiazol-4-yl group, a 2-alkylthiothiazol-4-yl group, 2-alkylsulfinylthiazol-4-yl group, a 2-alkylsulfonylthiazol-4-yl group, a 2-arylthiazol-4-yl group, and a 2-bromothiazol-4-yl group.

There are two solid structures, i.e., an "E" form and a "Z" form in the oxime portions in the oxime derivatives represented by the general formulas (1) and (2). The solid structures of both the "E" and "Z" forms are included in the scope of the present invention. In general, synthesized products of oxime derivatives include both forms as mixtures, and it is possible to isolate by a separation and purification processes.

Although the "Z" form of the oxime derivative is more effective as the plant disease control chemical than the "E" form, the "Z" form gradually changes into the "E" form under ordinary conditions and the ratio between the "E" and "Z" forms is stabilized at a constant ratio. The constant ratio between the "E" and "Z" forms varies with the types of oxime derivatives.

The oxime derivatives of the present invention, which are represented by the general formulas (1) and (2) may be manufactured by, for example, the following methods. However, it is to be understood that the methods of manufacturing the oxime derivatives of the present invention are not limited to the methods described in the following manufacturing examples.

Manufacturing Method A

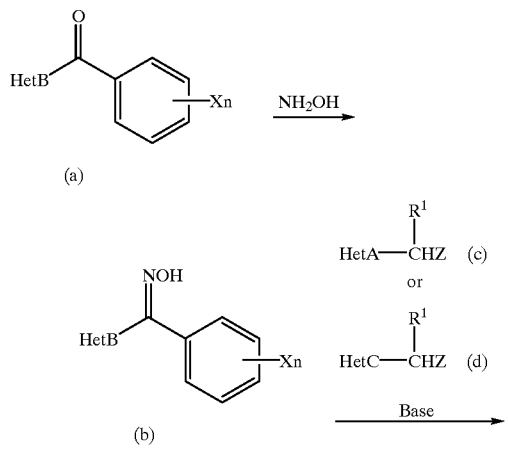

-continued

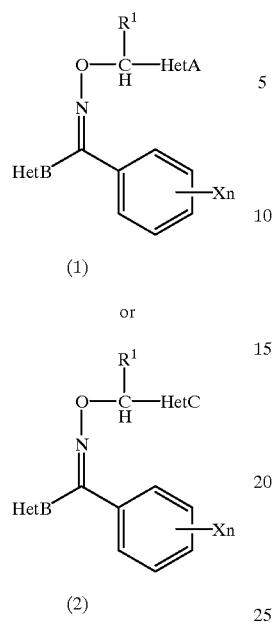

(In the formula, the definitions of HetA, HetB, Het C, X, n, and $R^1$ are the same as those defined hereinbefore.)

An oxime compound expressed by general chemical formulas (1) or (2) is manufactured by the following steps of, obtaining a hydroxyimino compound (b) by reacting an azole-methanone compound (a) with hydroxylamine; and reacting the obtained hydroxyimino compound with halogenized compounds (c) or (d) in the presence of salts (such as sodium hydride, sodium hydroxide, pottasium hydroxide, sodium carbonate, pottasium carbonate, cesium carbonate, triethylamine, pyridine, N,N-dimethylaminopyridine). As a process for synthesizing the azole-methanone compound, a process described in, for example, "Synthesis", p. 976 (1982), is applicable.

The practical chemical structures of the compounds expressed by the general formulas (1) and (2), and which are manufactured by the above manufacturing steps are shown in Tables 1 to 66.

TABLE 1

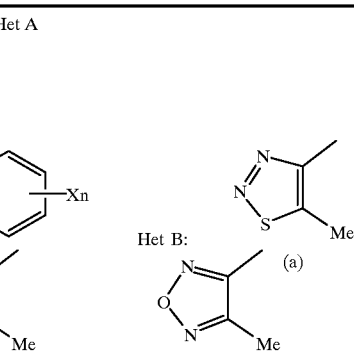

TABLE 1-continued

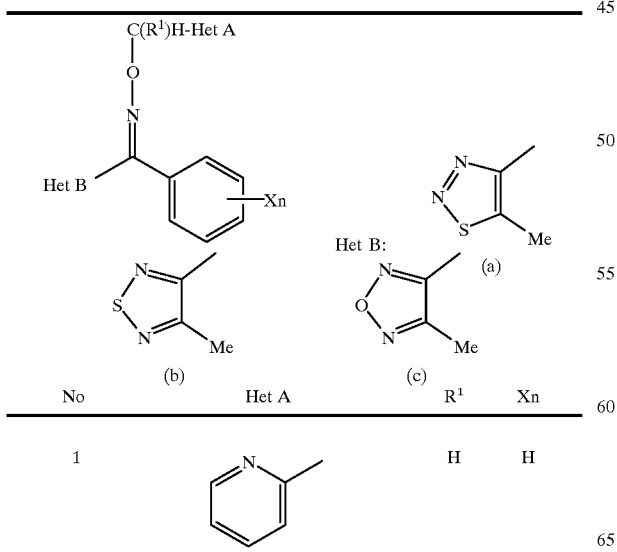

| No | Het A | $R^1$ | Xn |
|----|-------|-------|-----|
| 2 | 3-pyridyl | H | H |
| 3 | 4-pyridyl | H | H |
| 4 | 4-pyrimidinyl | H | H |
| 5 | 2-pyrazinyl | H | H |
| 6 | 2-pyrimidinyl | H | H |
| 7 | 3-pyridazinyl | H | H |
| 8 | 6-methyl-2-pyridyl | H | H |
| 9 | 5-methyl-2-pyridyl | H | H |
| 10 | 4-methyl-2-pyridyl | H | H |

TABLE 1-continued

Het B—C(=N—O—C(R¹)H-Het A)—C₆H₄—Xn

Het B:

(a) 4-methyl-5-methyl-1,2,3-thiadiazole
(b) 4-methyl-1,2,5-thiadiazole (dimethyl)
(c) 4-methyl-3-methyl-1,2,5-oxadiazole

| No | Het A | R¹ | Xn |
|---|---|---|---|
| 11 | 2-methyl-3-methyl-pyridine | H | H |
| 12 | 6-chloro-2-methyl-pyridine | H | H |
| 13 | 5-chloro-2-methyl-pyridine | H | H |
| 14 | 4-chloro-2-methyl-pyridine | H | H |
| 15 | 3-chloro-2-methyl-pyridine | H | H |
| 16 | 6-fluoro-2-methyl-pyridine | H | H |
| 17 | 5-fluoro-2-methyl-pyridine | H | H |
| 18 | 5-CF₃-2-methyl-pyridine | H | H |
| 19 | 5-MeS-2-methyl-pyridine | H | H |
| 20 | 5-MeS(O)₂-2-methyl-pyridine | H | H |
| 21 | 5-CN-2-methyl-pyridine | H | H |
| 22 | 5-MeO-2-methyl-pyridine | H | H |
| 23 | 3-Cl-5-CF₃-2-methyl-pyridine | H | H |
| 24 | 3,5-dichloro-2-methyl-pyridine | H | H |
| 25 | 3-Cl-5-Me-2-methyl-pyridine | H | H |
| 26 | 3-Cl-5-F-2-methyl-pyridine | H | H |

TABLE 2
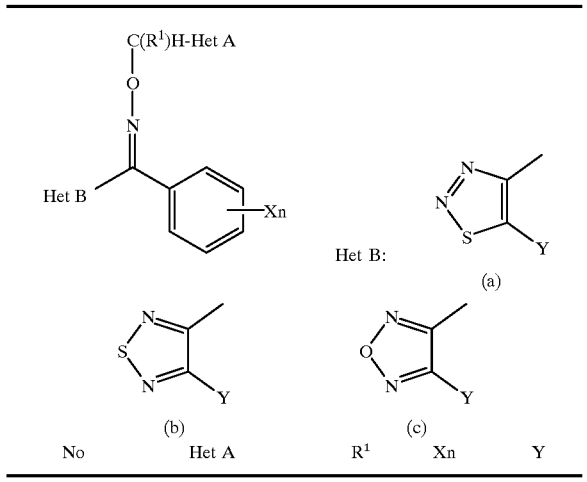
| No | Het A | R¹ | Xn | Y |
|---|---|---|---|---|
| 1 | 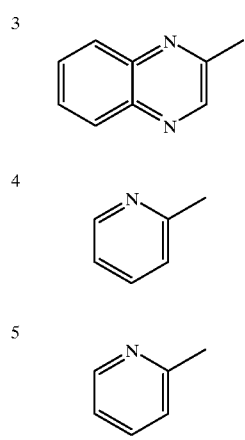 quinoline-2-yl | H | H | $CH_3$ |
| 2 | quinazoline-2-yl | H | H | $CH_3$ |
| 3 | quinoxaline-2-yl | H | H | $CH_3$ |
| 4 | pyridin-2-yl | $CH_3$ | H | $CH_3$ |
| 5 | pyridin-2-yl | $C_2H_5$ | H | $CH_3$ |
| 6 | pyridin-2-yl | $C_3H_7$ | H | $CH_3$ |
| 7 | pyridin-2-yl | H | H | $C_2H_5$ |
| 8 | pyridin-2-yl | H | 3-$CF_3$ | $C_3H_7$ |
TABLE 2-continued
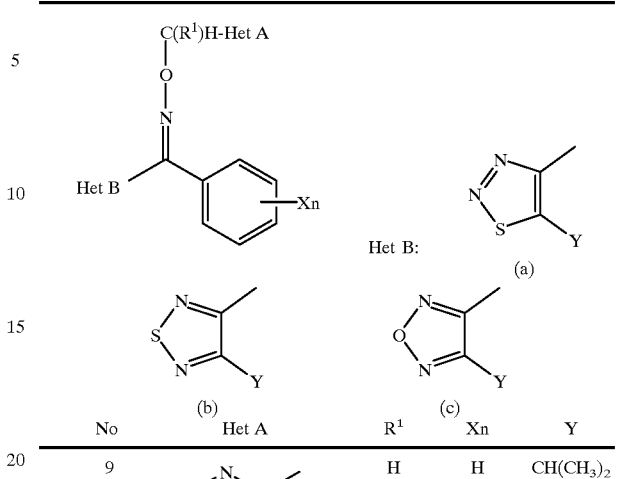
| No | Het A | R¹ | Xn | Y |
|---|---|---|---|---|
| 9 | pyridin-2-yl | H | H | $CH(CH_3)_2$ |
| 10 | pyridin-2-yl | H | H | H |
TABLE 3
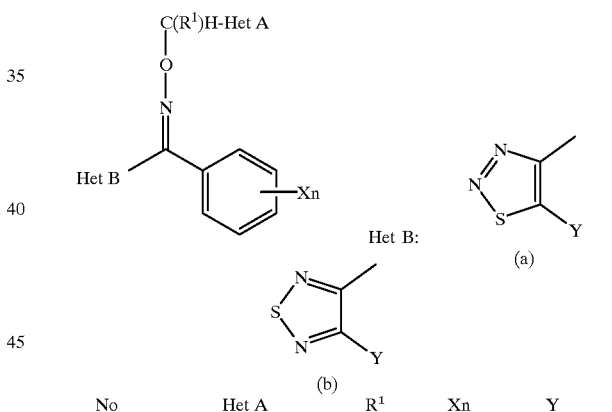
| No | Het A | R¹ | Xn | Y |
|---|---|---|---|---|
| 1 | pyridin-2-yl | H | H | $CF_3$ |
| 2 | pyridin-2-yl | H | 4-Cl | $CF_3$ |
| 3 | pyridin-2-yl | H | 3-Cl | $CF_3$ |
| 4 | pyridin-2-yl | H | 4-F | $CF_3$ |

TABLE 3-continued

Structure: C(R¹)H-Het A attached via O-N=C(Het B)(phenyl-Xn)

Het B:
(a) 4-methyl-1,2,3-thiadiazol-5-yl with Y substituent
(b) 4-methyl-1,2,3-thiadiazol-5-yl with Y at 4-position (isomer)

| No | Het A | R¹ | Xn | Y |
|----|-------|----|----|---|
| 5 | 2-pyridyl (6-methyl) | H | 3-F | CF₃ |
| 6 | 2-pyridyl (6-methyl) | H | H | Cl |
| 7 | 2-pyridyl (6-methyl) | H | 4-Cl | Cl |
| 8 | 2-pyridyl (6-methyl) | H | 3-Cl | Cl |
| 9 | 2-pyridyl (6-methyl) | H | 4-F | Cl |
| 10 | 2-pyridyl (6-methyl) | H | 3-F | Cl |

TABLE 4

Structure: 2-pyridyl-CH₂-O-N=C(Het B)(phenyl-Xn)

Het B:
(a) 4-methyl-5-methyl-1,2,3-thiadiazole
(b) 3,4-dimethyl-1,2,5-thiadiazole
(c) 3,4-dimethyl-1,2,5-oxadiazole

| No | Xn |
|----|-----|
| 1 | 2-Cl |
| 2 | 3-Cl |
| 3 | 4-Cl |
| 4 | 2,3-(Cl)₂ |
| 5 | 2,4-(Cl)₂ |
| 6 | 2,5-(Cl)₂ |
| 7 | 2,6-(Cl)₂ |
| 8 | 3,4-(Cl)₂ |
| 9 | 3,5-(Cl)₂ |
| 10 | 2,4,6-(Cl)₃ |
| 11 | 2-F |
| 12 | 3-F |
| 13 | 4-F |
| 14 | 2,3-(F)₂ |
| 15 | 2,4-(F)₂ |
| 16 | 2,5-(F)₂ |
| 17 | 2,6-(F)₂ |
| 18 | 3,4-(F)₂ |
| 19 | 3,5-(F)₂ |
| 20 | 2,4,6-(F)₃ |
| 21 | 2-CH₃ |
| 22 | 3-CH₃ |
| 23 | 4-CH₃ |
| 24 | 2,3-(CH₃)₂ |
| 25 | 2,4-(CH₃)₂ |
| 26 | 2,5-(CH₃)₂ |
| 27 | 2,6-(CH₃)₂ |
| 28 | 3,5-(CH₃)₂ |
| 29 | 3-Cl, 5-CH₃ |
| 30 | 3-F, 5-CH₃ |
| 31 | 3-F, 5-Cl |
| 32 | 2-CF₃ |
| 33 | 3-CF₃ |
| 34 | 4-CF₃ |
| 35 | 2-CN |
| 36 | 3-CN |
| 37 | 4-CN |
| 38 | 2-SMe |
| 39 | 3-SMe |
| 40 | 4-SMe |
| 41 | 2-SO₂Me |
| 42 | 3-SO₂Me |
| 43 | 4-SO₂Me |
| 44 | 2-Br |
| 45 | 3-Br |
| 46 | 4-Br |
| 47 | 2-OH |
| 48 | 3-OH |
| 49 | 4-OH |
| 50 | 2-OMe |
| 51 | 3-OMe |
| 52 | 4-OMe |

TABLE 5
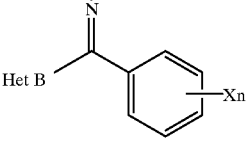
| No | Xn |
|----|-----|
| 1 | 2-OPh |
| 2 | 3-OPh |
| 3 | 4-OPh |
| 4 | 2-OCF$_2$H |
| 5 | 3-OCF$_2$H |
| 6 | 4-OCF$_2$H |
| 7 | 2-CO$_2$H |
| 8 | 3-CO$_2$H |
| 9 | 4-CO$_2$H |
| 10 | 2-CO$_2$Me |
| 11 | 3-CO$_2$Me |
| 12 | 2-CF$_2$Cl |
| 13 | 3-CF$_2$Cl |
| 14 | 4-CF$_2$Cl |
| 15 | 2-NO$_2$ |
| 16 | 3-NO$_2$ |
| 17 | 4-NO$_2$ |
| 18 | 2-NH$_2$ |
| 19 | 3-NH$_2$ |
| 20 | 4-NH$_2$ |
| 21 | 4-Ph |
| 22 | 2-OCF$_3$ |
| 23 | 3-OCF$_3$ |
| 24 | 4-OCF$_3$ |
| 25 | 2,4-(CF$_3$)$_2$ |
| 26 | 2,5-(CF$_3$)$_2$ |
| 27 | 2,6-(CF$_3$)$_2$ |
| 28 | 3,4-(CF$_3$)$_2$ |
| 29 | 2,5-(CF$_3$)$_2$ |
| 30 | 2-Me, 4-Cl |
| 31 | 2-Me, 3-Cl |
| 32 | 2-Cl, 4-Me |
| 33 | 2-Et, 6-Me |
| 34 | 2-Cl, 5-CF$_3$ |
| 35 | 2-Cl, 6-F |
| 36 | 2,4,6-(Me)$_3$ |
TABLE 6
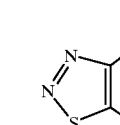
| No | Het C | R$^1$ | Xn |
|----|-------|-------|-----|
| 1 | 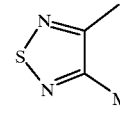 | H | H |
| 2 | 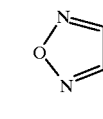 | H | H |
| 3 |  | H | H |
| 4 | 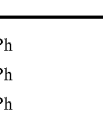 | H | H |
| 5 | | H | H |
| 6 | | H | H |
| 7 | | H | H |
| 8 | | H | H |
| 9 | | H | H |

TABLE 6-continued

| No | Het C | R¹ | Xn |
|---|---|---|---|
| 10 | (N-methylimidazole) | H | H |
| 11 | (N-methylpyrazole) | H | H |
| 12 | (N-methyltriazole) | H | H |
| 13 | (N-methyltriazole) | H | H |
| 14 | (N-methyltetrazole) | H | H |
| 15 | (oxazole) | H | H |
| 16 | (oxazole) | H | H |
| 17 | (isoxazole) | H | H |
| 18 | (thiazole) | H | H |
| 19 | (thiazole) | H | H |
| 20 | (isothiazole) | H | H |
| 21 | (thiadiazole) | H | H |
| 22 | (thiadiazole) | H | H |
| 23 | (thiadiazole) | H | H |
| 24 | (thiadiazole) | H | H |
| 25 | (thiadiazole) | H | H |
| 26 | (oxadiazole) | H | H |

TABLE 7
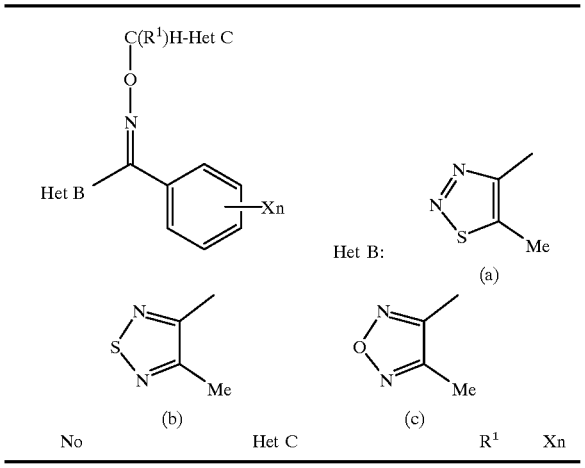
| No | Het C | R¹ | Xn |
|---|---|---|---|
| 1 | | H | H |
| 2 | | H | H |
| 3 | | H | H |
| 4 | | H | H |
| 5 | | H | H |
| 6 | | H | H |
| 7 | | H | H |
| 8 | | H | H |
| 9 | | H | H |
TABLE 7-continued
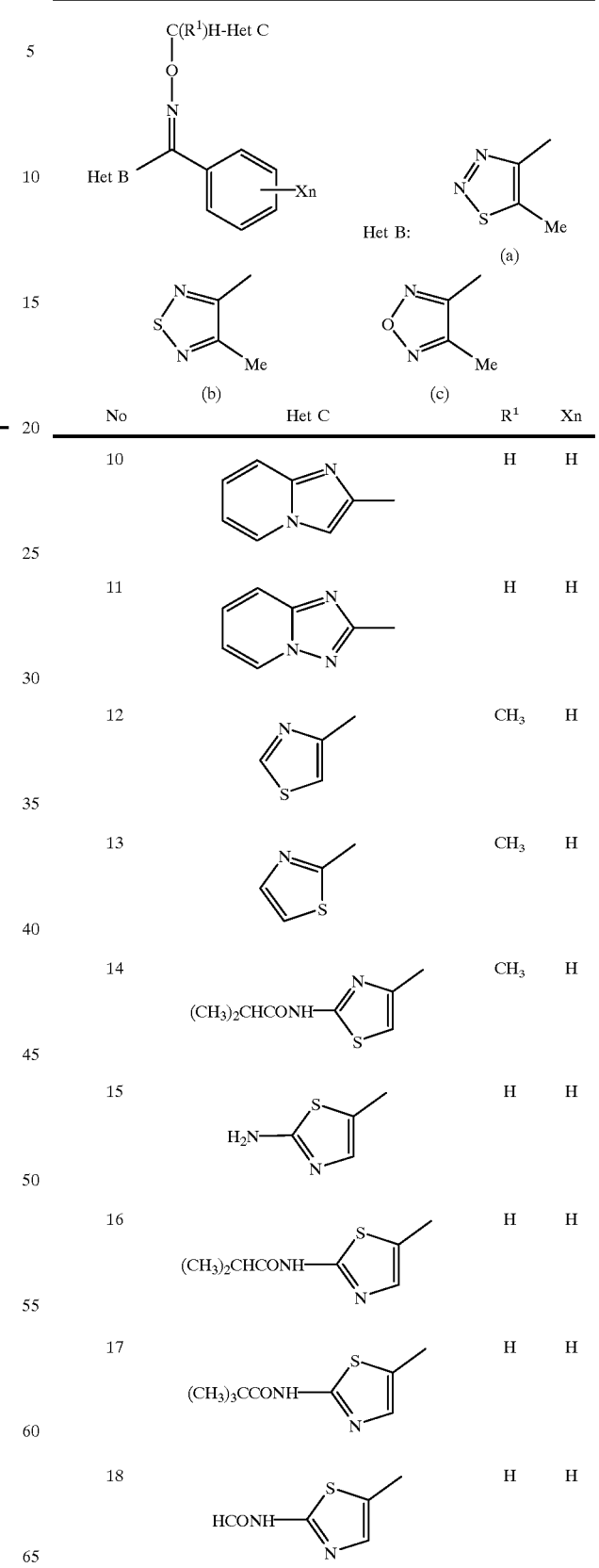
| No | Het C | R¹ | Xn |
|---|---|---|---|
| 10 | | H | H |
| 11 | | H | H |
| 12 | | $CH_3$ | H |
| 13 | | $CH_3$ | H |
| 14 | | $CH_3$ | H |
| 15 | | H | H |
| 16 | | H | H |
| 17 | | H | H |
| 18 | | H | H |

TABLE 7-continued

Structure: Het B−C(=N−O−C(R¹)H−Het C)−C₆H₄−Xn

Het B:
(a) 4-methyl-5-methyl-1,2,3-thiadiazole
(b) 4-methyl-3-methyl-1,2,5-thiadiazole
(c) 4-methyl-3-methyl-1,2,5-oxadiazole

| No | Het C | R¹ | Xn |
|---|---|---|---|
| 19 | CH₃CONH-(5-methyl-thiazol-2-yl) | H | H |
| 20 | (CH₃)₂CHCH₂CONH-(5-methyl-thiazol-2-yl) | H | H |
| 21 | PhCONH-(5-methyl-thiazol-2-yl) | H | H |

TABLE 8

Structure: Het B−C(=N−O−C(R¹)H−Het C)−C₆H₄−Xn

Het B:
(a) 4-methyl-5-methyl-1,2,3-thiadiazole
(b) 4-methyl-3-methyl-1,2,5-thiadiazole
(c) 4-methyl-3-methyl-1,2,5-oxadiazole

| No | Het C | R¹ | Xn |
|---|---|---|---|
| 1 | H₂N-(4-methyl-thiazol-2-yl) | H | H |
| 2 | HCONH-(4-methyl-thiazol-2-yl) | H | H |
| 3 | CH₃CONH-(4-methyl-thiazol-2-yl) | H | H |
| 4 | C₂H₅CONH-(4-methyl-thiazol-2-yl) | H | H |
| 5 | C₃H₇CONH-(4-methyl-thiazol-2-yl) | H | H |
| 6 | C₄H₉CONH-(4-methyl-thiazol-2-yl) | H | H |
| 7 | (CH₃)₂CHCONH-(4-methyl-thiazol-2-yl) | H | H |
| 8 | (CH₃)₂CHCH₂CONH-(4-methyl-thiazol-2-yl) | H | H |
| 9 | C₂H₆(CH₃)CHCONH-(4-methyl-thiazol-2-yl) | H | H |
| 10 | (CH₃)₃CCONH-(4-methyl-thiazol-2-yl) | H | H |
| 11 | (CH₃)₃CCH₂CONH-(4-methyl-thiazol-2-yl) | H | H |

TABLE 8-continued

Het B—C(=N—O—C(R¹)H-Het C)—C₆H₄—Xn

Het B:

(a) 4-methyl-5-methyl-1,2,3-thiadiazole (b) 3-methyl-4-methyl-1,2,5-thiadiazole (c) 3-methyl-4-methyl-1,2,5-oxadiazole

| No | Het C | R¹ | Xn |
|---|---|---|---|
| 12 | C₂H₅(CH₃)₂CCONH-thiazolyl(4-Me) | H | H |
| 13 | (C₂H₅)₂CHCONH-thiazolyl(4-Me) | H | H |
| 14 | CF₃CONH-thiazolyl(4-Me) | H | H |
| 15 | C₂F₅CONH-thiazolyl(4-Me) | H | H |
| 16 | C₃F₇CONH-thiazolyl(4-Me) | H | H |
| 17 | ClH₂CCONH-thiazolyl(4-Me) | H | H |
| 18 | Cl₂HCCONH-thiazolyl(4-Me) | H | H |
| 19 | Cl₃CCONH-thiazolyl(4-Me) | H | H |
| 20 | (CH₃)₂(Br)CCONH-thiazolyl(4-Me) | H | H |
| 21 | Cl(F)₂CCONH-thiazolyl(4-Me) | H | H |
| 22 | CH₃OCONH-thiazolyl(4-Me) | H | H |
| 23 | C₂H₅OCONH-thiazolyl(4-Me) | H | H |
| 24 | (CH₃)₂CHOCONH-thiazolyl(4-Me) | H | H |
| 25 | (CH₃)₃COCONH-thiazolyl(4-Me) | H | H |

TABLE 9

Het B—C(=N—O—C(R¹)H-Het C)—C₆H₄—Xn

Het B:

(a) 4-methyl-5-methyl-1,2,3-thiadiazole (b) 3-methyl-4-methyl-1,2,5-thiadiazole (c) 3-methyl-4-methyl-1,2,5-oxadiazole

| No | Het C | R¹ | Xn |
|---|---|---|---|
| 1 | (C₂H₅)₂CHCH₂OCONH-thiazolyl(4-Me) | H | H |
| 2 | CH₃NH-thiazolyl(4-Me) | H | H |
| 3 | C₂H₅NH-thiazolyl(4-Me) | H | H |
| 4 | (C₃H₇)₂CHNH-thiazolyl(4-Me) | H | H |

TABLE 9-continued

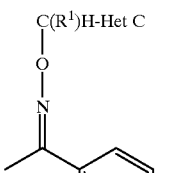

| No | Het C | R¹ | Xn |
|----|-------|-----|-----|
| 5  | (CH₃)₃CNH-thiazole-4-Me | H | H |
| 6  | (Ph)₃CNH-thiazole-4-Me | H | H |
| 7  | (CH₃)₂CHCO(CH₃)N-thiazole-4-Me | H | H |
| 8  | (CH₃)₂N-thiazole-4-Me | H | H |
| 9  | CH₃-thiazole-4-Me | H | H |
| 10 | C₂H₅-thiazole-4-Me | H | H |
| 11 | C₃H₇-thiazole-4-Me | H | H |
| 12 | (CH₃)₂CH-thiazole-4-Me | H | H |
| 13 | (CH₃)₃C-thiazole-4-Me | H | H |
| 14 | CF₃-thiazole-4-Me | H | H |
| 15 | Cl-thiazole-4-Me | H | H |
| 16 | Br-thiazole-4-Me | H | H |
| 17 | CH₃O-thiazole-4-Me | H | H |
| 18 | C₂H₅O-thiazole-4-Me | H | H |
| 19 | C₃H₇O-thiazole-4-Me | H | H |
| 20 | (CH₃)₂CHO-thiazole-4-Me | H | H |
| 21 | (CH₃)₂CHCH₂O-thiazole-4-Me | H | H |
| 22 | F₂HCO-thiazole-4-Me | H | H |

TABLE 9-continued

Structure: C(R¹)H-Het C — O — N = C(Het B)(phenyl-Xn)

Het B:
(a) 4-methyl-5-methyl-1,2,3-thiadiazole
(b) 3-methyl-4-methyl-1,2,5-thiadiazole
(c) 3-methyl-4-methyl-1,2,5-oxadiazole

| No | Het C | R¹ | Xn |
|---|---|---|---|
| 23 | CH₃S-(4-methylthiazol-2-yl) | H | H |
| 24 | C₂H₅S-(4-methylthiazol-2-yl) | H | H |
| 25 | C₃H₇S-(4-methylthiazol-2-yl) | H | H |
| 26 | (CH₃)₂CHS-(4-methylthiazol-2-yl) | H | H |

TABLE 10

Structure: C(R¹)H-Het C — O — N = C(Het B)(phenyl-Xn)

Het B:
(a) 4-methyl-5-methyl-1,2,3-thiadiazole
(b) 3-methyl-4-methyl-1,2,5-thiadiazole
(c) 3-methyl-4-methyl-1,2,5-oxadiazole

| No | Het C | R¹ | Xn |
|---|---|---|---|
| 1 | (CH₃)₂CH₂CH₂S-(4-methylthiazol-2-yl) | H | H |
| 2 | F₂HCS-(4-methylthiazol-2-yl) | H | H |
| 3 | CH₃S(O)₂-(4-methylthiazol-2-yl) | H | H |
| 4 | (CH₃)₂CHS(O)₂-(4-methylthiazol-2-yl) | H | H |
| 5 | F₂HCS(O)-(4-methylthiazol-2-yl) | H | H |
| 6 | F₂HCS(O)₂-(4-methylthiazol-2-yl) | H | H |
| 7 | (CH₃)₂CHSCH₂-(4-methylthiazol-2-yl) | H | H |
| 8 | C₂H₅O₂C-(2-methylthiazol-4-yl) | H | H |
| 9 | CH₃NHOC-(2-methylthiazol-4-yl) | H | H |
| 10 | CH₃CH₂NHOC-(2-methylthiazol-4-yl) | H | H |
| 11 | (CH₃)₂CHNHOC-(2-methylthiazol-4-yl) | H | H |

TABLE 10-continued

Het B—C(=N—O—C(R¹)H-Het C)—C₆H₄—Xn

Het B:
(a) 4-methyl-5-methyl-1,2,3-thiadiazole
(b) 4-methyl-3-methyl-1,2,5-thiadiazole
(c) 4-methyl-3-methyl-1,2,5-oxadiazole

| No | Het C | R¹ | Xn |
|---|---|---|---|
| 12 | (CH₃)₃CNHOC-thiazole-2-methyl | H | H |
| 13 | (CH₃)₂NOC-thiazole-2-methyl | H | H |
| 14 | MeS-imidazole(N-Me)-4-methyl | H | H |
| 15 | MeSO₂-imidazole(N-Me)-4-methyl | H | H |
| 16 | imidazole(N-SO₂N(CH₃)₂)-4-methyl | H | H |
| 17 | MeSO₂-imidazole(N-SO₂N(CH₃)₂)-4-methyl | H | H |
| 18 | NC-imidazole(N-SO₂N(CH₃)₂)-4-methyl | H | H |
| 19 | triazole(N-CH₃)-methyl | H | H |
| 20 | triazole(N-CPh₃)-methyl | H | H |
| 21 | triazole(N-CH₂OMe)-methyl | H | H |

TABLE 11

Het B—C(=N—O—C(R¹)H-Het C)—C₆H₄—Xn

Het B:
(a) 4-methyl-5-methyl-1,2,3-thiadiazole
(b) 4-methyl-3-methyl-1,2,5-thiadiazole
(c) 4-methyl-3-methyl-1,2,5-oxadiazole

| No | Het C | R¹ | Xn |
|---|---|---|---|
| 1 | H₂N-1,3,4-thiadiazole-methyl | H | H |
| 2 | HCONH-1,3,4-thiadiazole-methyl | H | H |
| 3 | CH₃CONH-1,3,4-thiadiazole-methyl | H | H |
| 4 | C₂H₅CONH-1,3,4-thiadiazole-methyl | H | H |

TABLE 11-continued

Het B—C(=N—O—C(R¹)H-Het C)—C₆H₄—Xn

Het B:

(a) 4-methyl-5-Me-1,2,3-thiadiazole
(b) 4-methyl-5-Me-1,2,5-thiadiazole
(c) 4-methyl-5-Me-1,2,5-oxadiazole

| No | Het C | R¹ | Xn |
|---|---|---|---|
| 5 | C₃H₇CONH-[1,3,4-thiadiazole-methyl] | H | H |
| 6 | C₄H₉CONH-[1,3,4-thiadiazole-methyl] | H | H |
| 7 | (CH₃)₂CHCONH-[1,3,4-thiadiazole-methyl] | H | H |
| 8 | (CH₃)₂CHCH₂CONH-[1,3,4-thiadiazole-methyl] | H | H |
| 9 | (CH₃)₃CCONH-[1,3,4-thiadiazole-methyl] | H | H |
| 10 | cyclo-C₆H₁₁CH₂CONH-[1,3,4-thiadiazole-methyl] | H | H |
| 11 | CF₃CONH-[1,3,4-thiadiazole-methyl] | H | H |
| 12 | C₆H₅CONH-[1,3,4-thiadiazole-methyl] | H | H |
| 13 | CH₃OCONH-[1,3,4-thiadiazole-methyl] | H | H |
| 14 | (Ph)₃CNH-[1,3,4-thiadiazole-methyl] | H | H |

TABLE 12

Het B—C(=N—O—C(R¹)H-Het C)—C₆H₄—Xn

Het B:

(a) 4-methyl-5-Y-1,2,3-thiadiazole
(b) 4-methyl-3-Y-1,2,5-thiadiazole
(c) 4-methyl-3-Y-1,2,5-oxadiazole

| No | Het C | R¹ | Xn | Y |
|---|---|---|---|---|
| 1 | 4-methylthiazole | C₂H₅ | 3-Cl | CH₃ |
| 2 | 2-methylthiazole | C₃H₇ | 4-Cl | CH₃ |
| 3 | (CH₃)₂CHCONH-4-methylthiazole | C₄H₉ | 4-F | CH₃ |
| 4 | 4-methylthiazole | C₂H₅ | H | CH₃ |
| 5 | 2-methylthiazole | C₃H₇ | H | CH₃ |
| 6 | (CH₃)₂CHCONH-4-methylthiazole | C₄H₉ | H | CH₃ |
| 7 | 4-methylthiazole | H | H | C₂H₅ |
| 8 | 2-methylthiazole | H | H | C₂H₅ |
| 9 | (CH₃)₂CHCONH-4-methylthiazole | H | H | C₂H₅ |
| 10 | 4-methylthiazole | H | 3-Cl | C₃H₇ |
| 11 | 2-methylthiazole | H | 4-Cl | C₄H₉ |
| 12 | (CH₃)₂CHCONH-4-methylthiazole | H | 4-F | C₄H₉ |

TABLE 12-continued
| No | Het C | R¹ | Xn | Y |
|---|---|---|---|---|
| 13 | (4-methylthiazole) | H | H | $CH(CH_3)_2$ |
| 14 | (2-methylthiazole) | H | H | $CH(CH_3)_2$ |
| 15 | (CH₃)₂CHCONH-(4-methylthiazol-2-yl) | H | H | $CH(CH_3)_2$ |
TABLE 13
| No | Xn |
|---|---|
| 1 | 2-Cl |
| 2 | 3-Cl |
| 3 | 4-Cl |
| 4 | 2,3-(Cl)₂ |
| 5 | 2,4-(Cl)₂ |
| 6 | 2,5-(Cl)₂ |
| 7 | 2,6-(Cl)₂ |
| 8 | 3,4-(Cl)₂ |
| 9 | 3,5-(Cl)₂ |
| 10 | 2,4,6-(Cl)₃ |
| 11 | 2-F |
| 12 | 3-F |
| 13 | 4-F |
TABLE 13-continued
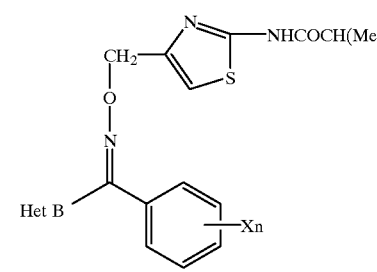
| No | Xn |
|---|---|
| 14 | 2,3-(F)₂ |
| 15 | 2,4-(F)₂ |
| 16 | 2,5-(F)₂ |
| 17 | 2,6-(F)₂ |
| 18 | 3,4-(F)₂ |
| 19 | 3,5-(F)₂ |
| 20 | 2,4,6-(F)₃ |
| 21 | 2-CH₃ |
| 22 | 3-CH₃ |
| 23 | 4-CH₃ |
| 24 | 2,3-(CH₃)₂ |
| 25 | 2,4-(CH₃)₂ |
| 26 | 2,5-(CH₃)₂ |
| 27 | 2,6-(CH₃)₂ |
| 28 | 3,5-(CH₃)₂ |
| 29 | 3-Cl, 5-CH₃ |
| 30 | 3-F, 5-CH₃ |
| 31 | 3-F, 5-Cl |
| 32 | 2-CF₃ |
| 33 | 3-CF₃ |
| 34 | 4-CF₃ |
| 35 | 2-CN |
| 36 | 3-CN |
| 37 | 4-CN |
| 38 | 2-SMe |
| 39 | 3-SMe |
| 40 | 4-SMe |
| 41 | 2-SO₂Me |
| 42 | 3-SO₂Me |
| 43 | 4-SO₂Me |
| 44 | 2-Br |
| 45 | 3-Br |
| 46 | 4-Br |
| 47 | 2-OH |
| 48 | 3-OH |
| 49 | 4-OH |
| 50 | 2-OMe |

TABLE 13-continued
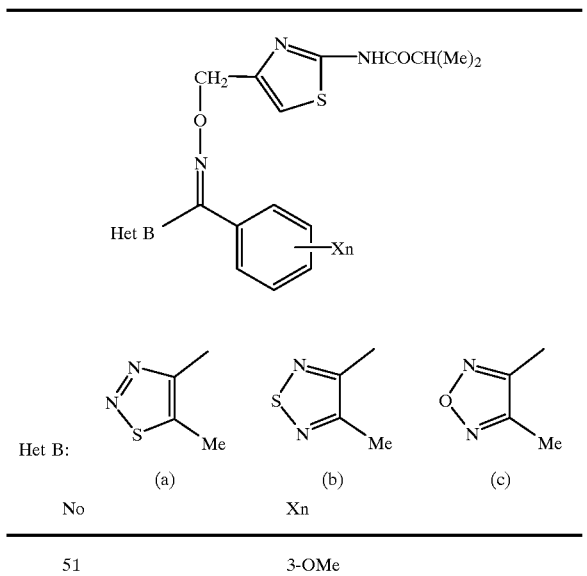
| Het B: | (a) | (b) | (c) |
| No | Xn |
|---|---|
| 51 | 3-OMe |
| 52 | 4-OMe |
TABLE 14
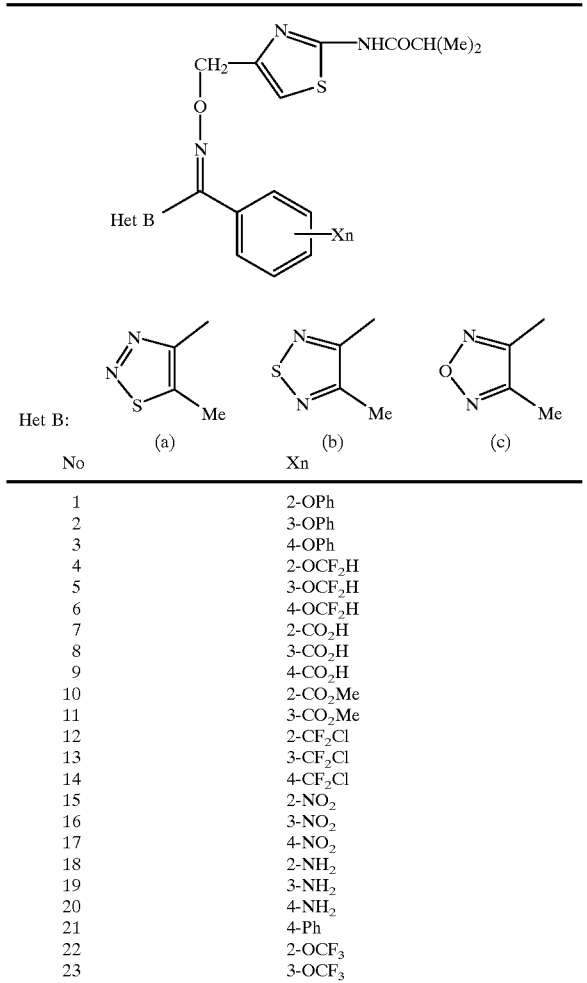
| Het B: | (a) | (b) | (c) |
| No | Xn |
|---|---|
| 1 | 2-OPh |
| 2 | 3-OPh |
| 3 | 4-OPh |
| 4 | 2-OCF$_2$H |
| 5 | 3-OCF$_2$H |
| 6 | 4-OCF$_2$H |
| 7 | 2-CO$_2$H |
| 8 | 3-CO$_2$H |
| 9 | 4-CO$_2$H |
| 10 | 2-CO$_2$Me |
| 11 | 3-CO$_2$Me |
| 12 | 2-CF$_2$Cl |
| 13 | 3-CF$_2$Cl |
| 14 | 4-CF$_2$Cl |
| 15 | 2-NO$_2$ |
| 16 | 3-NO$_2$ |
| 17 | 4-NO$_2$ |
| 18 | 2-NH$_2$ |
| 19 | 3-NH$_2$ |
| 20 | 4-NH$_2$ |
| 21 | 4-Ph |
| 22 | 2-OCF$_3$ |
| 23 | 3-OCF$_3$ |
TABLE 14-continued
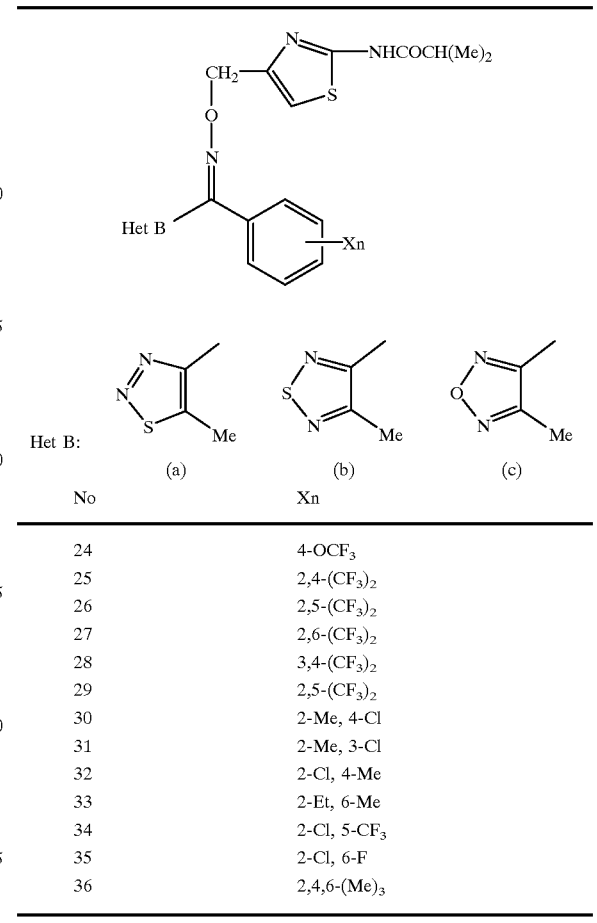
| Het B: | (a) | (b) | (c) |
| No | Xn |
|---|---|
| 24 | 4-OCF$_3$ |
| 25 | 2,4-(CF$_3$)$_2$ |
| 26 | 2,5-(CF$_3$)$_2$ |
| 27 | 2,6-(CF$_3$)$_2$ |
| 28 | 3,4-(CF$_3$)$_2$ |
| 29 | 2,5-(CF$_3$)$_2$ |
| 30 | 2-Me, 4-Cl |
| 31 | 2-Me, 3-Cl |
| 32 | 2-Cl, 4-Me |
| 33 | 2-Et, 6-Me |
| 34 | 2-Cl, 5-CF$_3$ |
| 35 | 2-Cl, 6-F |
| 36 | 2,4,6-(Me)$_3$ |
TABLE 15
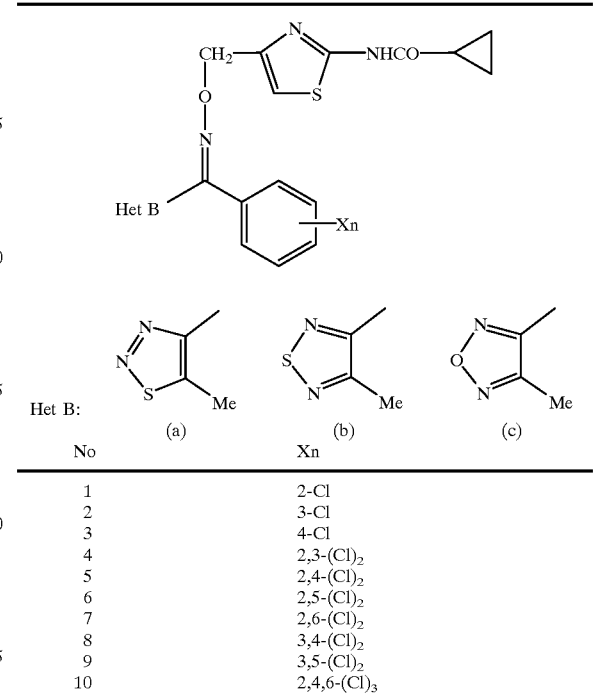
| Het B: | (a) | (b) | (c) |
| No | Xn |
|---|---|
| 1 | 2-Cl |
| 2 | 3-Cl |
| 3 | 4-Cl |
| 4 | 2,3-(Cl)$_2$ |
| 5 | 2,4-(Cl)$_2$ |
| 6 | 2,5-(Cl)$_2$ |
| 7 | 2,6-(Cl)$_2$ |
| 8 | 3,4-(Cl)$_2$ |
| 9 | 3,5-(Cl)$_2$ |
| 10 | 2,4,6-(Cl)$_3$ |

TABLE 15-continued

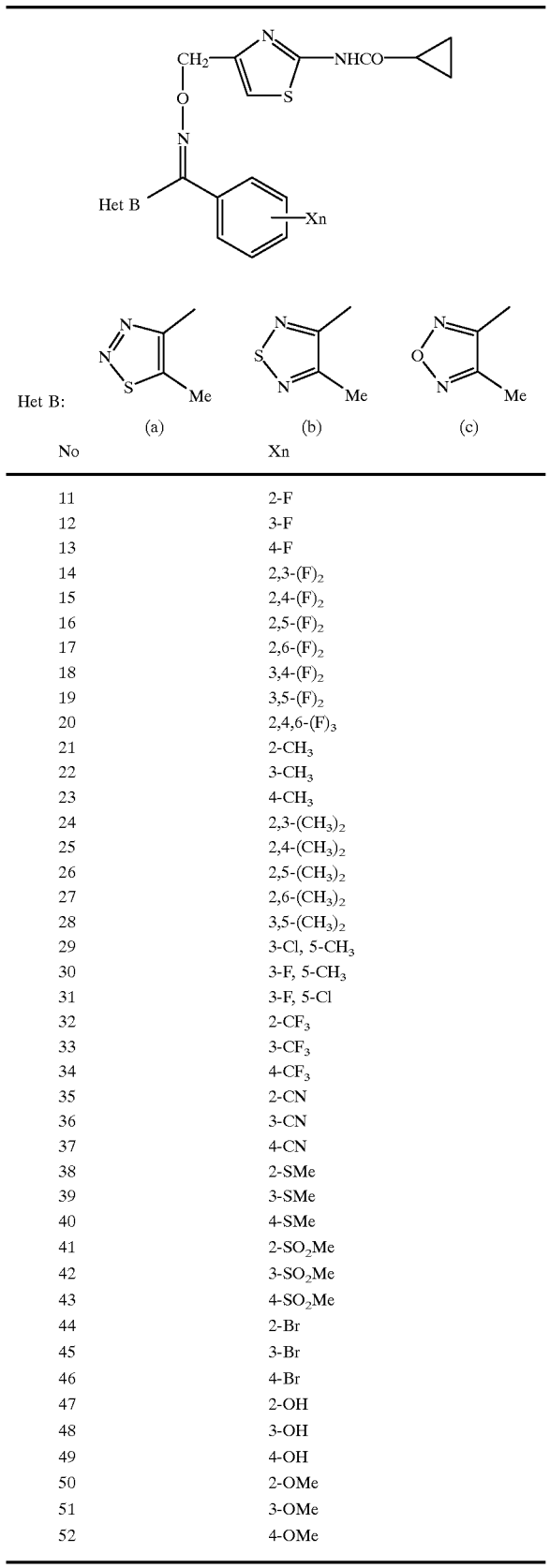

| No | Xn |
|---|---|
| 11 | 2-F |
| 12 | 3-F |
| 13 | 4-F |
| 14 | 2,3-(F)$_2$ |
| 15 | 2,4-(F)$_2$ |
| 16 | 2,5-(F)$_2$ |
| 17 | 2,6-(F)$_2$ |
| 18 | 3,4-(F)$_2$ |
| 19 | 3,5-(F)$_2$ |
| 20 | 2,4,6-(F)$_3$ |
| 21 | 2-CH$_3$ |
| 22 | 3-CH$_3$ |
| 23 | 4-CH$_3$ |
| 24 | 2,3-(CH$_3$)$_2$ |
| 25 | 2,4-(CH$_3$)$_2$ |
| 26 | 2,5-(CH$_3$)$_2$ |
| 27 | 2,6-(CH$_3$)$_2$ |
| 28 | 3,5-(CH$_3$)$_2$ |
| 29 | 3-Cl, 5-CH$_3$ |
| 30 | 3-F, 5-CH$_3$ |
| 31 | 3-F, 5-Cl |
| 32 | 2-CF$_3$ |
| 33 | 3-CF$_3$ |
| 34 | 4-CF$_3$ |
| 35 | 2-CN |
| 36 | 3-CN |
| 37 | 4-CN |
| 38 | 2-SMe |
| 39 | 3-SMe |
| 40 | 4-SMe |
| 41 | 2-SO$_2$Me |
| 42 | 3-SO$_2$Me |
| 43 | 4-SO$_2$Me |
| 44 | 2-Br |
| 45 | 3-Br |
| 46 | 4-Br |
| 47 | 2-OH |
| 48 | 3-OH |
| 49 | 4-OH |
| 50 | 2-OMe |
| 51 | 3-OMe |
| 52 | 4-OMe |

TABLE 16

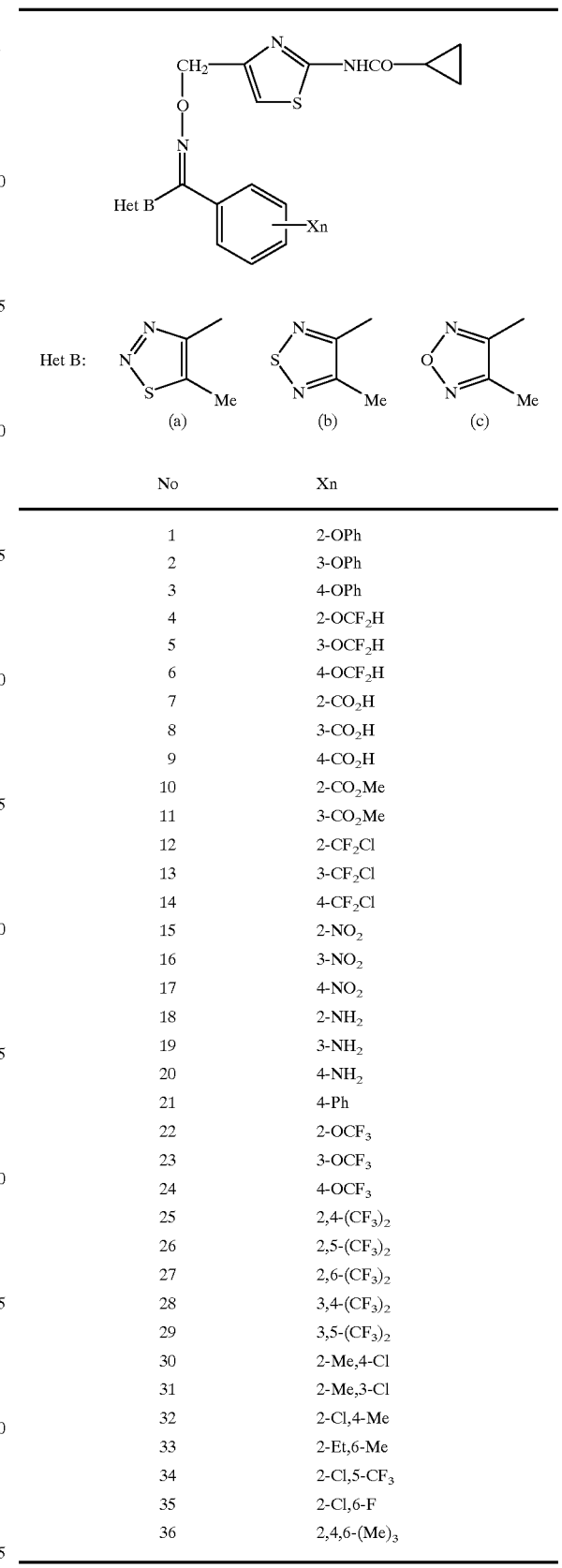

| No | Xn |
|---|---|
| 1 | 2-OPh |
| 2 | 3-OPh |
| 3 | 4-OPh |
| 4 | 2-OCF$_2$H |
| 5 | 3-OCF$_2$H |
| 6 | 4-OCF$_2$H |
| 7 | 2-CO$_2$H |
| 8 | 3-CO$_2$H |
| 9 | 4-CO$_2$H |
| 10 | 2-CO$_2$Me |
| 11 | 3-CO$_2$Me |
| 12 | 2-CF$_2$Cl |
| 13 | 3-CF$_2$Cl |
| 14 | 4-CF$_2$Cl |
| 15 | 2-NO$_2$ |
| 16 | 3-NO$_2$ |
| 17 | 4-NO$_2$ |
| 18 | 2-NH$_2$ |
| 19 | 3-NH$_2$ |
| 20 | 4-NH$_2$ |
| 21 | 4-Ph |
| 22 | 2-OCF$_3$ |
| 23 | 3-OCF$_3$ |
| 24 | 4-OCF$_3$ |
| 25 | 2,4-(CF$_3$)$_2$ |
| 26 | 2,5-(CF$_3$)$_2$ |
| 27 | 2,6-(CF$_3$)$_2$ |
| 28 | 3,4-(CF$_3$)$_2$ |
| 29 | 3,5-(CF$_3$)$_2$ |
| 30 | 2-Me,4-Cl |
| 31 | 2-Me,3-Cl |
| 32 | 2-Cl,4-Me |
| 33 | 2-Et,6-Me |
| 34 | 2-Cl,5-CF$_3$ |
| 35 | 2-Cl,6-F |
| 36 | 2,4,6-(Me)$_3$ |

TABLE 17

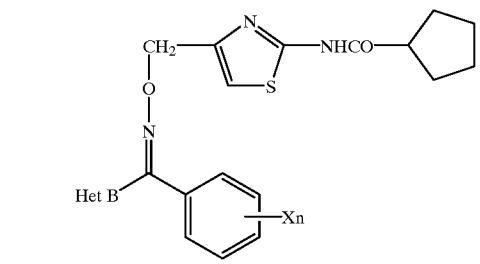

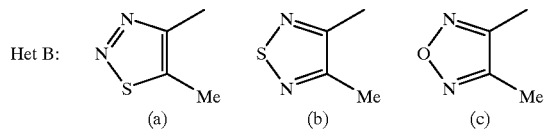

| No | Xn |
|---|---|
| 1 | 2-Cl |
| 2 | 3-Cl |
| 3 | 4-Cl |
| 4 | 2,3-(Cl)$_2$ |
| 5 | 2,4-(Cl)$_2$ |
| 6 | 2,5-(Cl)$_2$ |
| 7 | 2,6-(Cl)$_2$ |
| 8 | 3,4-(Cl)$_2$ |
| 9 | 3,5-(Cl)$_2$ |
| 10 | 2,4,6-(Cl)$_3$ |
| 11 | 2-F |
| 12 | 3-F |
| 13 | 4-F |
| 14 | 2,3-(F)$_2$ |
| 15 | 2,4-(F)$_2$ |
| 16 | 2,5-(F)$_2$ |
| 17 | 2,6-(F)$_2$ |
| 18 | 3,4-(F)$_2$ |
| 19 | 3,5-(F)$_2$ |
| 20 | 2,4,6-(F)$_3$ |
| 21 | 2-CH$_3$ |
| 22 | 3-CH$_3$ |
| 23 | 4-CH$_3$ |
| 24 | 2,3-(CH$_3$)$_2$ |
| 25 | 2,4-(CH$_3$)$_2$ |
| 26 | 2,5-(CH$_3$)$_2$ |
| 27 | 2,6-(CH$_3$)$_2$ |
| 28 | 3,5-(CH$_3$)$_2$ |
| 29 | 3-Cl,5-CH$_3$ |
| 30 | 3-F,5-CH$_3$ |
| 31 | 3-F,5-Cl |
| 32 | 2-CF$_3$ |
| 33 | 3-CF$_3$ |
| 34 | 4-CF$_3$ |
| 35 | 2-CN |
| 36 | 3-CN |
| 37 | 4-CN |
| 38 | 2-SMe |
| 39 | 3-SMe |
| 40 | 4-SMe |
| 41 | 2-SO$_2$Me |
| 42 | 3-SO$_2$Me |
| 43 | 4-SO$_2$Me |
| 44 | 2-Br |
| 45 | 3-Br |
| 46 | 4-Br |
| 47 | 2-OH |
| 48 | 3-OH |
| 49 | 4-OH |

TABLE 17-continued

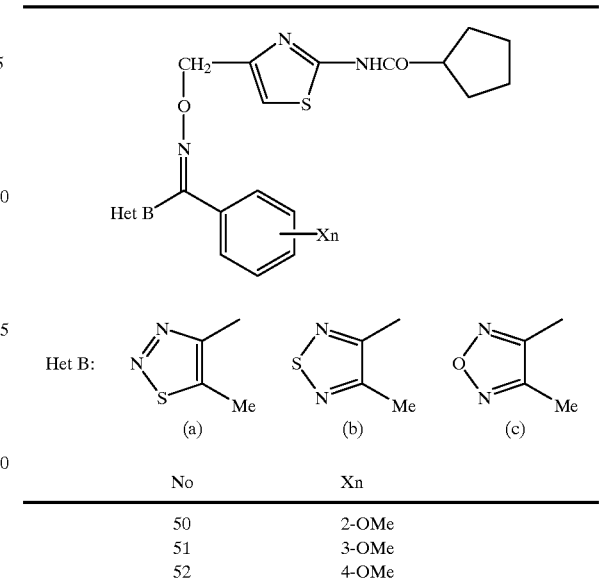

| No | Xn |
|---|---|
| 50 | 2-OMe |
| 51 | 3-OMe |
| 52 | 4-OMe |

TABLE 18

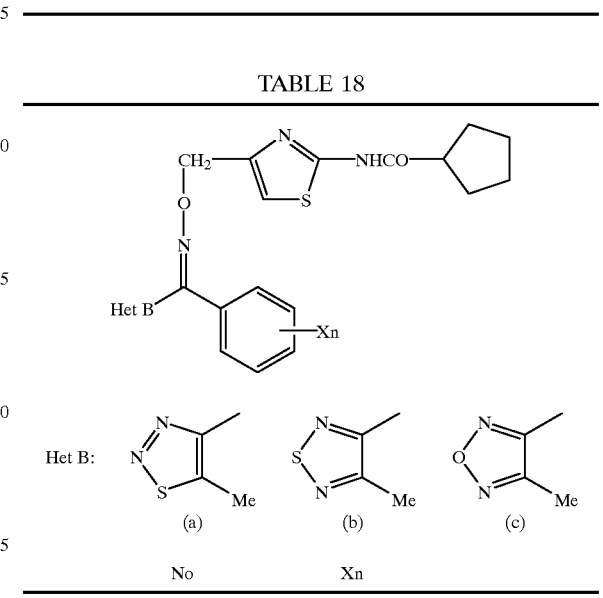

| No | Xn |
|---|---|
| 1 | 2-OPh |
| 2 | 3-OPh |
| 3 | 4-OPh |
| 4 | 2-OCF$_2$H |
| 5 | 3-OCF$_2$H |
| 6 | 4-OCF$_2$H |
| 7 | 2-CO$_2$H |
| 8 | 3-CO$_2$H |
| 9 | 4-CO$_2$H |
| 10 | 2-CO$_2$Me |
| 11 | 3-CO$_2$Me |
| 12 | 2-CF$_2$Cl |
| 13 | 3-CF$_2$Cl |
| 14 | 4-CF$_2$Cl |
| 15 | 2-NO$_2$ |
| 16 | 3-NO$_2$ |
| 17 | 4-NO$_2$ |
| 18 | 2-NH$_2$ |
| 19 | 3-NH$_2$ |
| 20 | 4-NH$_2$ |
| 21 | 4-Ph |
| 22 | 2-OCF$_3$ |
| 23 | 3-OCF$_3$ |
| 24 | 4-OCF$_3$ |

TABLE 18-continued
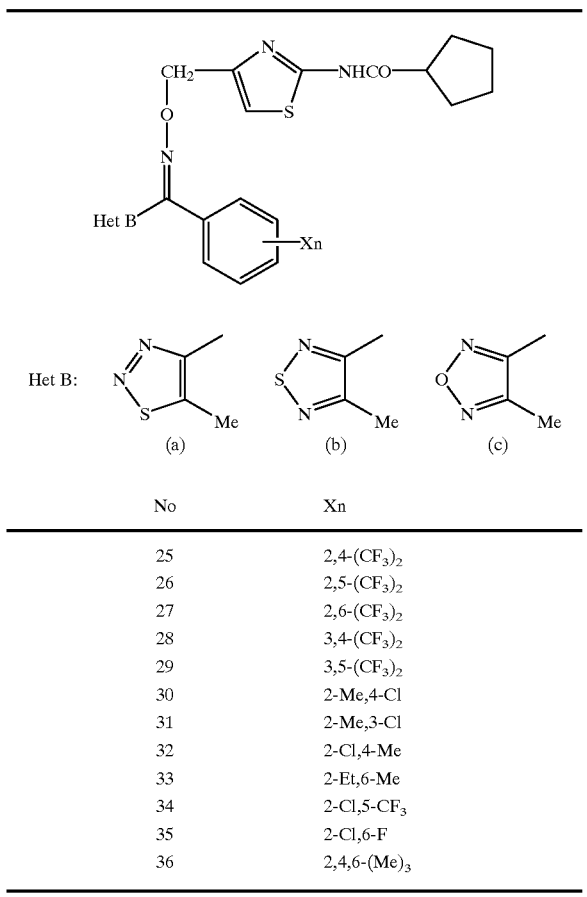
| No | Xn |
|---|---|
| 25 | 2,4-(CF₃)₂ |
| 26 | 2,5-(CF₃)₂ |
| 27 | 2,6-(CF₃)₂ |
| 28 | 3,4-(CF₃)₂ |
| 29 | 3,5-(CF₃)₂ |
| 30 | 2-Me,4-Cl |
| 31 | 2-Me,3-Cl |
| 32 | 2-Cl,4-Me |
| 33 | 2-Et,6-Me |
| 34 | 2-Cl,5-CF₃ |
| 35 | 2-Cl,6-F |
| 36 | 2,4,6-(Me)₃ |
TABLE 19
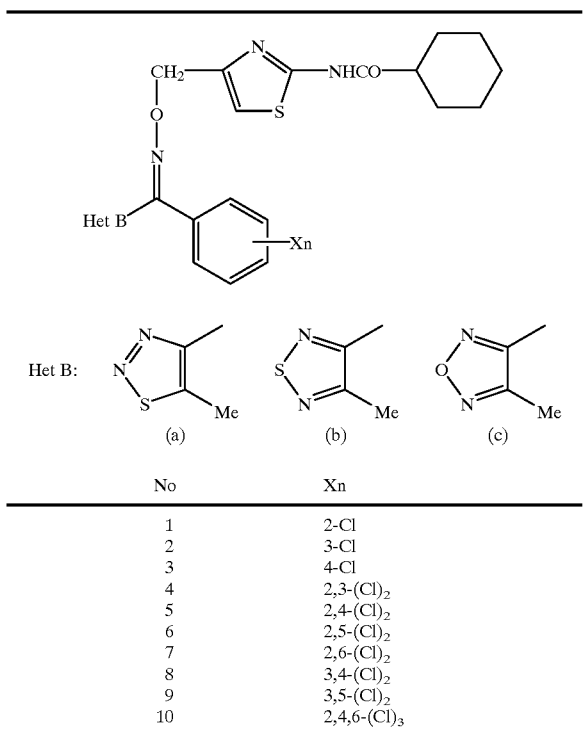
| No | Xn |
|---|---|
| 1 | 2-Cl |
| 2 | 3-Cl |
| 3 | 4-Cl |
| 4 | 2,3-(Cl)₂ |
| 5 | 2,4-(Cl)₂ |
| 6 | 2,5-(Cl)₂ |
| 7 | 2,6-(Cl)₂ |
| 8 | 3,4-(Cl)₂ |
| 9 | 3,5-(Cl)₂ |
| 10 | 2,4,6-(Cl)₃ |
TABLE 19-continued
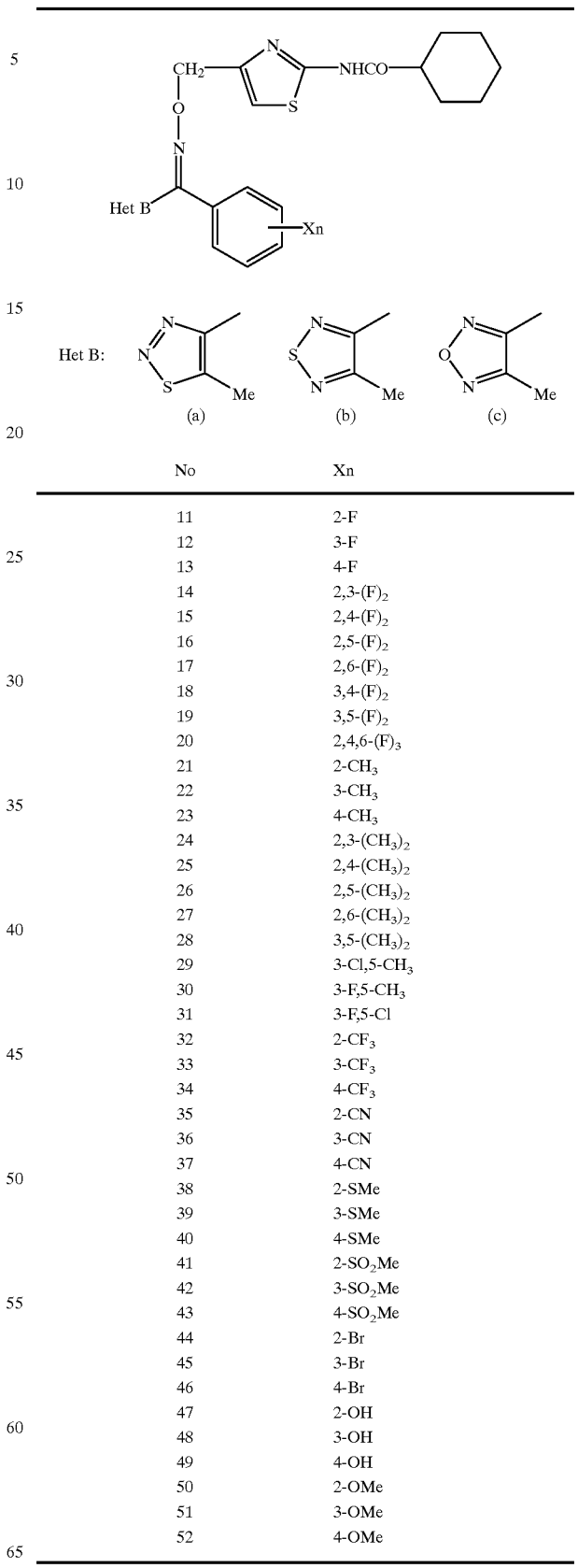
| No | Xn |
|---|---|
| 11 | 2-F |
| 12 | 3-F |
| 13 | 4-F |
| 14 | 2,3-(F)₂ |
| 15 | 2,4-(F)₂ |
| 16 | 2,5-(F)₂ |
| 17 | 2,6-(F)₂ |
| 18 | 3,4-(F)₂ |
| 19 | 3,5-(F)₂ |
| 20 | 2,4,6-(F)₃ |
| 21 | 2-CH₃ |
| 22 | 3-CH₃ |
| 23 | 4-CH₃ |
| 24 | 2,3-(CH₃)₂ |
| 25 | 2,4-(CH₃)₂ |
| 26 | 2,5-(CH₃)₂ |
| 27 | 2,6-(CH₃)₂ |
| 28 | 3,5-(CH₃)₂ |
| 29 | 3-Cl,5-CH₃ |
| 30 | 3-F,5-CH₃ |
| 31 | 3-F,5-Cl |
| 32 | 2-CF₃ |
| 33 | 3-CF₃ |
| 34 | 4-CF₃ |
| 35 | 2-CN |
| 36 | 3-CN |
| 37 | 4-CN |
| 38 | 2-SMe |
| 39 | 3-SMe |
| 40 | 4-SMe |
| 41 | 2-SO₂Me |
| 42 | 3-SO₂Me |
| 43 | 4-SO₂Me |
| 44 | 2-Br |
| 45 | 3-Br |
| 46 | 4-Br |
| 47 | 2-OH |
| 48 | 3-OH |
| 49 | 4-OH |
| 50 | 2-OMe |
| 51 | 3-OMe |
| 52 | 4-OMe |

TABLE 20

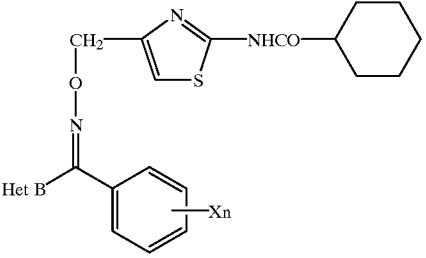

Het B:

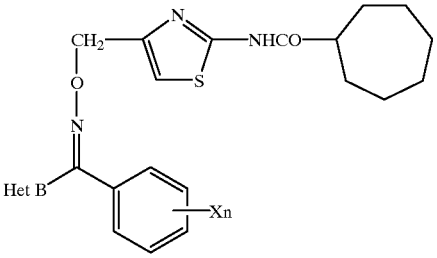

| No | Xn |
|---|---|
| 1 | 2-OPh |
| 2 | 3-OPh |
| 3 | 4-OPh |
| 4 | 2-OCF$_2$H |
| 5 | 3-OCF$_2$H |
| 6 | 4-OCF$_2$H |
| 7 | 2-CO$_2$H |
| 8 | 3-CO$_2$H |
| 9 | 4-CO$_2$H |
| 10 | 2-CO$_2$Me |
| 11 | 3-CO$_2$Me |
| 12 | 2-CF$_2$Cl |
| 13 | 3-CF$_2$Cl |
| 14 | 4-CF$_2$Cl |
| 15 | 2-NO$_2$ |
| 16 | 3-NO$_2$ |
| 17 | 4-NO$_2$ |
| 18 | 2-NH$_2$ |
| 19 | 3-NH$_2$ |
| 20 | 4-NH$_2$ |
| 21 | 4-Ph |
| 22 | 2-OCF$_3$ |
| 23 | 3-OCF$_3$ |
| 24 | 4-OCF$_3$ |
| 25 | 2,4-(CF$_3$)$_2$ |
| 26 | 2,5-(CF$_3$)$_2$ |
| 27 | 2,6-(CF$_3$)$_2$ |
| 28 | 3,4-(CF$_3$)$_2$ |
| 29 | 3,5-(CF$_3$)$_2$ |
| 30 | 2-Me,4-Cl |
| 31 | 2-Me,3-Cl |
| 32 | 2-Cl,4-Me |
| 33 | 2-Et,6-Me |
| 34 | 2-Cl,5-CF$_3$ |
| 35 | 2-Cl,6-F |
| 36 | 2,4,6-(Me)$_3$ |

TABLE 21

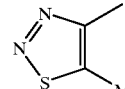

Het B:

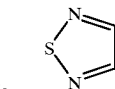

| No | Xn |
|---|---|
| 1 | 2-Cl |
| 2 | 3-Cl |
| 3 | 4-Cl |
| 4 | 2,3-(Cl)$_2$ |
| 5 | 2,4-(Cl)$_2$ |
| 6 | 2,5-(Cl)$_2$ |
| 7 | 2,6-(Cl)$_2$ |
| 8 | 3,4-(Cl)$_2$ |
| 9 | 3,5-(Cl)$_2$ |
| 10 | 2,4,6-(Cl)$_3$ |
| 11 | 2-F |
| 12 | 3-F |
| 13 | 4-F |
| 14 | 2,3-(F)$_2$ |
| 15 | 2,4-(F)$_2$ |
| 16 | 2,5-(F)$_2$ |
| 17 | 2,6-(F)$_2$ |
| 18 | 3,4-(F)$_2$ |
| 19 | 3,5-(F)$_2$ |
| 20 | 2,4,6-(F)$_3$ |
| 21 | 2-CH$_3$ |
| 22 | 3-CH$_3$ |
| 23 | 4-CH$_3$ |
| 24 | 2,3-(CH$_3$)$_2$ |
| 25 | 2,4-(CH$_3$)$_2$ |
| 26 | 2,5-(CH$_3$)$_2$ |
| 27 | 2,6-(CH$_3$)$_2$ |
| 28 | 3,5-(CH$_3$)$_2$ |
| 29 | 3-Cl,5-CH$_3$ |
| 30 | 3-F,5-CH$_3$ |
| 31 | 3-F,5-Cl |
| 32 | 2-CF$_3$ |
| 33 | 3-CF$_3$ |
| 34 | 4-CF$_3$ |
| 35 | 2-CN |
| 36 | 3-CN |
| 37 | 4-CN |
| 38 | 2-SMe |
| 39 | 3-SMe |
| 40 | 4-SMe |
| 41 | 2-SO$_2$Me |
| 42 | 3-SO$_2$Me |
| 43 | 4-SO$_2$Me |
| 44 | 2-Br |
| 45 | 3-Br |
| 46 | 4-Br |
| 47 | 2-OH |
| 48 | 3-OH |
| 49 | 4-OH |
| 50 | 2-OMe |
| 51 | 3-OMe |
| 52 | 4-OMe |

TABLE 22

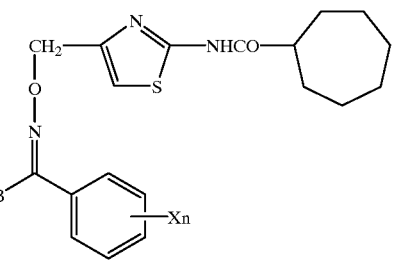

Het B:
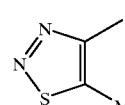

| No | Xn |
|---|---|
| 1 | 2-OPh |
| 2 | 3-OPh |
| 3 | 4-OPh |
| 4 | 2-OCF$_2$H |
| 5 | 3-OCF$_2$H |
| 6 | 4-OCF$_2$H |
| 7 | 2-CO$_2$H |
| 8 | 3-CO$_2$H |
| 9 | 4-CO$_2$H |
| 10 | 2-CO$_2$Me |
| 11 | 3-CO$_2$Me |
| 12 | 2-CF$_2$Cl |
| 13 | 3-CF$_2$Cl |
| 14 | 4-CF$_2$Cl |
| 15 | 2-NO$_2$ |
| 16 | 3-NO$_2$ |
| 17 | 4-NO$_2$ |
| 18 | 2-NH$_2$ |
| 19 | 3-NH$_2$ |
| 20 | 4-NH$_2$ |
| 21 | 4-Ph |
| 22 | 2-OCF$_3$ |
| 23 | 3-OCF$_3$ |
| 24 | 4-OCF$_3$ |
| 25 | 2,4-(CF$_3$)$_2$ |
| 26 | 2,5-(CF$_3$)$_2$ |
| 27 | 2,6-(CF$_3$)$_2$ |
| 28 | 3,4-(CF$_3$)$_2$ |
| 29 | 3,5-(CF$_3$)$_2$ |
| 30 | 2-Me,4-Cl |
| 31 | 2-Me,3-Cl |
| 32 | 2-Cl,4-Me |
| 33 | 2-Et,6-Me |
| 34 | 2-Cl,5-CF$_3$ |
| 35 | 2-Cl,6-F |
| 36 | 2,4,6-(Me)$_3$ |

TABLE 23

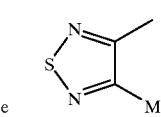

Het B:
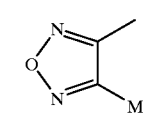

| No | Xn |
|---|---|
| 1 | 2-Cl |
| 2 | 3-Cl |
| 3 | 4-Cl |
| 4 | 2,3-(Cl)$_2$ |
| 5 | 2,4-(Cl)$_2$ |
| 6 | 2,5-(Cl)$_2$ |
| 7 | 2,6-(Cl)$_2$ |
| 8 | 3,4-(Cl)$_2$ |
| 9 | 3,5-(Cl)$_2$ |
| 10 | 2,4,6-(Cl)$_3$ |
| 11 | 2-F |
| 12 | 3-F |
| 13 | 4-F |
| 14 | 2,3-(F)$_2$ |
| 15 | 2,4-(F)$_2$ |
| 16 | 2,5-(F)$_2$ |
| 17 | 2,6-(F)$_2$ |
| 18 | 3,4-(F)$_2$ |
| 19 | 3,5-(F)$_2$ |
| 20 | 2,4,6-(F)$_3$ |
| 21 | 2-CH$_3$ |
| 22 | 3-CH$_3$ |
| 23 | 4-CH$_3$ |
| 24 | 2,3-(CH$_3$)$_2$ |
| 25 | 2,4-(CH$_3$)$_2$ |
| 26 | 2,5-(CH$_3$)$_2$ |
| 27 | 2,6-(CH$_3$)$_2$ |
| 28 | 3,5-(CH$_3$)$_2$ |
| 29 | 3-Cl,5-CH$_3$ |
| 30 | 3-F,5-CH$_3$ |
| 31 | 3-F,5-Cl |
| 32 | 2-CF$_3$ |
| 33 | 3-CF$_3$ |
| 34 | 4-CF$_3$ |
| 35 | 2-CN |
| 36 | 3-CN |
| 37 | 4-CN |
| 38 | 2-SMe |
| 39 | 3-SMe |
| 40 | 4-SMe |
| 41 | 2-SO$_2$Me |
| 42 | 3-SO$_2$Me |
| 43 | 4-SO$_2$Me |
| 44 | 2-Br |
| 45 | 3-Br |
| 46 | 4-Br |
| 47 | 2-OH |
| 48 | 3-OH |
| 49 | 4-OH |
| 50 | 2-OMe |
| 51 | 3-OMe |
| 52 | 4-OMe |

TABLE 24

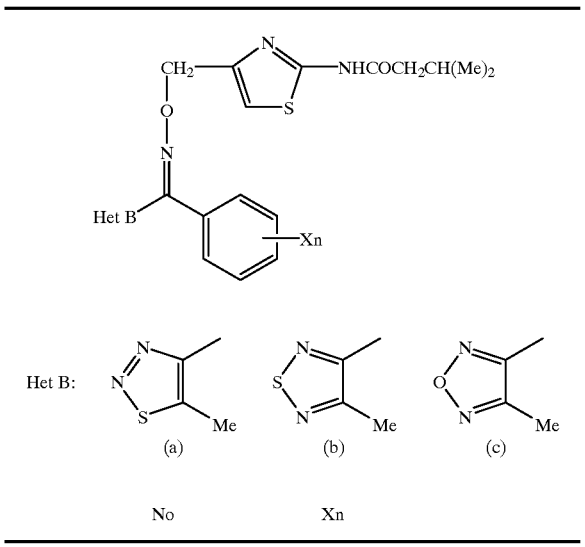

| No | Xn |
|---|---|
| 1 | 2-OPh |
| 2 | 3-OPh |
| 3 | 4-OPh |
| 4 | 2-OCF$_2$H |
| 5 | 3-OCF$_2$H |
| 6 | 4-OCF$_2$H |
| 7 | 2-CO$_2$H |
| 8 | 3-CO$_2$H |
| 9 | 4-CO$_2$H |
| 10 | 2-CO$_2$Me |
| 11 | 3-CO$_2$Me |
| 12 | 2-CF$_2$Cl |
| 13 | 3-CF$_2$Cl |
| 14 | 4-CF$_2$Cl |
| 15 | 2-NO$_2$ |
| 16 | 3-NO$_2$ |
| 17 | 4-NO$_2$ |
| 18 | 2-NH$_2$ |
| 19 | 3-NH$_2$ |
| 20 | 4-NH$_2$ |
| 21 | 4-Ph |
| 22 | 2-OCF$_3$ |
| 23 | 3-OCF$_3$ |
| 24 | 4-OCF$_3$ |
| 25 | 2,4-(CF$_3$)$_2$ |
| 26 | 2,5-(CF$_3$)$_2$ |
| 27 | 2,6-(CF$_3$)$_2$ |
| 28 | 3,4-(CF$_3$)$_2$ |
| 29 | 3,5-(CF$_3$)$_2$ |
| 30 | 2-Me,4-Cl |
| 31 | 2-Me,3-Cl |
| 32 | 2-Cl,4-Me |
| 33 | 2-Et,6-Me |
| 34 | 2-Cl,5-CF$_3$ |
| 35 | 2-Cl,6-F |
| 36 | 2,4,6-(Me)$_3$ |

TABLE 25

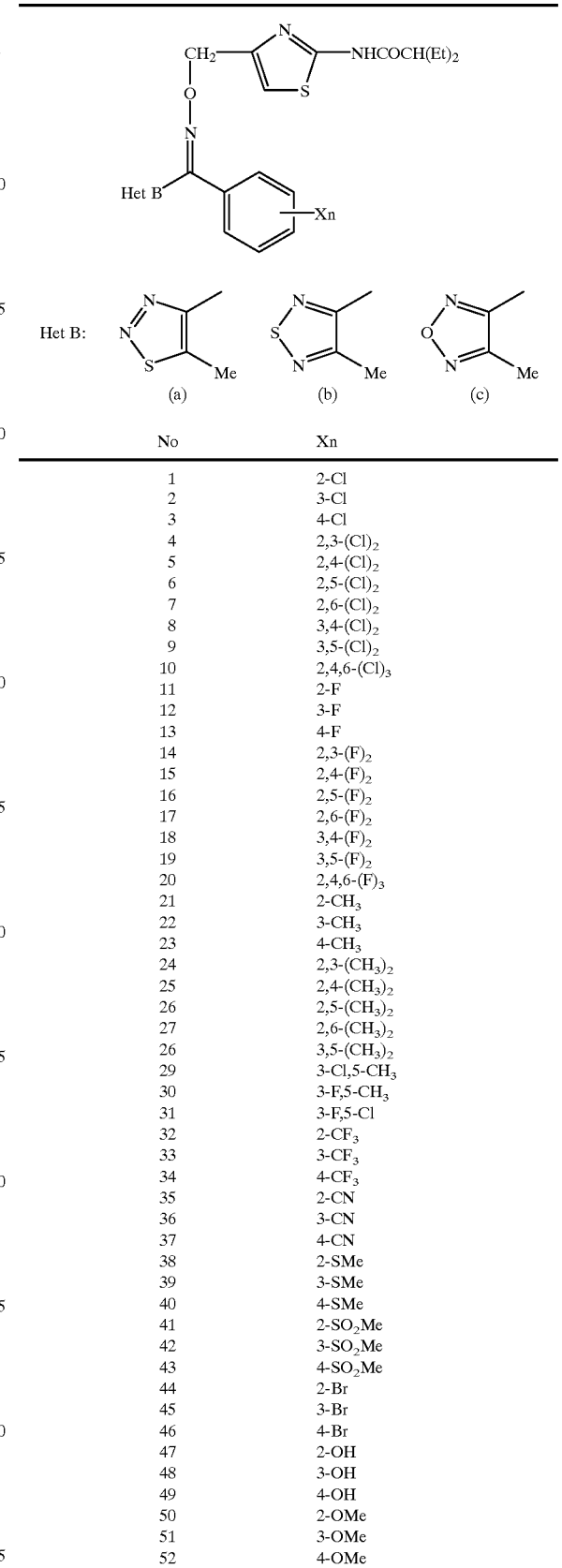

| No | Xn |
|---|---|
| 1 | 2-Cl |
| 2 | 3-Cl |
| 3 | 4-Cl |
| 4 | 2,3-(Cl)$_2$ |
| 5 | 2,4-(Cl)$_2$ |
| 6 | 2,5-(Cl)$_2$ |
| 7 | 2,6-(Cl)$_2$ |
| 8 | 3,4-(Cl)$_2$ |
| 9 | 3,5-(Cl)$_2$ |
| 10 | 2,4,6-(Cl)$_3$ |
| 11 | 2-F |
| 12 | 3-F |
| 13 | 4-F |
| 14 | 2,3-(F)$_2$ |
| 15 | 2,4-(F)$_2$ |
| 16 | 2,5-(F)$_2$ |
| 17 | 2,6-(F)$_2$ |
| 18 | 3,4-(F)$_2$ |
| 19 | 3,5-(F)$_2$ |
| 20 | 2,4,6-(F)$_3$ |
| 21 | 2-CH$_3$ |
| 22 | 3-CH$_3$ |
| 23 | 4-CH$_3$ |
| 24 | 2,3-(CH$_3$)$_2$ |
| 25 | 2,4-(CH$_3$)$_2$ |
| 26 | 2,5-(CH$_3$)$_2$ |
| 27 | 2,6-(CH$_3$)$_2$ |
| 26 | 3,5-(CH$_3$)$_2$ |
| 29 | 3-Cl,5-CH$_3$ |
| 30 | 3-F,5-CH$_3$ |
| 31 | 3-F,5-Cl |
| 32 | 2-CF$_3$ |
| 33 | 3-CF$_3$ |
| 34 | 4-CF$_3$ |
| 35 | 2-CN |
| 36 | 3-CN |
| 37 | 4-CN |
| 38 | 2-SMe |
| 39 | 3-SMe |
| 40 | 4-SMe |
| 41 | 2-SO$_2$Me |
| 42 | 3-SO$_2$Me |
| 43 | 4-SO$_2$Me |
| 44 | 2-Br |
| 45 | 3-Br |
| 46 | 4-Br |
| 47 | 2-OH |
| 48 | 3-OH |
| 49 | 4-OH |
| 50 | 2-OMe |
| 51 | 3-OMe |
| 52 | 4-OMe |

TABLE 26

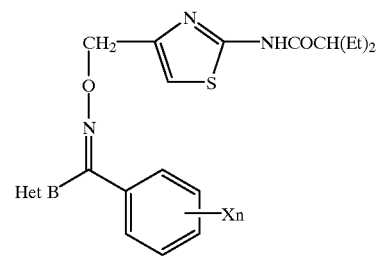

Het B:
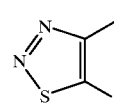
(a)    (b)    (c)

| No | Xn |
|---|---|
| 1 | 2-OPh |
| 2 | 3-OPh |
| 3 | 4-OPh |
| 4 | 2-OCF$_2$H |
| 5 | 3-OCF$_2$H |
| 6 | 4-OCF$_2$H |
| 7 | 2-CO$_2$H |
| 8 | 3-CO$_2$H |
| 9 | 4-CO$_2$H |
| 10 | 2-CO$_2$Me |
| 11 | 3-CO$_2$Me |
| 12 | 2-CF$_2$Cl |
| 13 | 3-CF$_2$Cl |
| 14 | 4-CF$_2$Cl |
| 15 | 2-NO$_2$ |
| 16 | 3-NO$_2$ |
| 17 | 4-NO$_2$ |
| 18 | 2-NH$_2$ |
| 19 | 3-NH$_2$ |
| 20 | 4-NH$_2$ |
| 21 | 4-Ph |
| 22 | 2-OCF$_3$ |
| 23 | 3-OCF$_3$ |
| 24 | 4-OCF$_3$ |
| 25 | 2,4-(CF$_3$)$_2$ |
| 26 | 2,5-(CF$_3$)$_2$ |
| 27 | 2,6-(CF$_3$)$_2$ |
| 28 | 3,4-(CF$_3$)$_2$ |
| 29 | 3,5-(CF$_3$)$_2$ |
| 30 | 2-Me,4-Cl |
| 31 | 2-Me,3-Cl |
| 32 | 2-Cl,4-Me |
| 33 | 2-Et,6-Me |
| 34 | 2-Cl,5-CF$_3$ |
| 35 | 2-Cl,6-F |
| 36 | 2,4,6-(Me)$_3$ |

TABLE 27

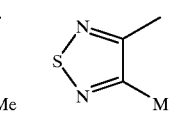

Het B:
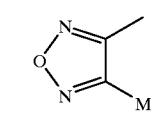
(a)    (b)    (c)

| No | Xn |
|---|---|
| 1 | 2-Cl |
| 2 | 3-Cl |
| 3 | 4-Cl |
| 4 | 2,3-(Cl)$_2$ |
| 5 | 2,4-(Cl)$_2$ |
| 6 | 2,5-(Cl)$_2$ |
| 7 | 2,6-(Cl)$_2$ |
| 8 | 3,4-(Cl)$_2$ |
| 9 | 3,5-(Cl)$_2$ |
| 10 | 2,4,6-(Cl)$_3$ |
| 11 | 2-F |
| 12 | 3-F |
| 13 | 4-F |
| 14 | 2,3-(F)$_2$ |
| 15 | 2,4-(F)$_2$ |
| 16 | 2,5-(F)$_2$ |
| 17 | 2,6-(F)$_2$ |
| 18 | 3,4-(F)$_2$ |
| 19 | 3,5-(F)$_2$ |
| 20 | 2,4,6-(F)$_3$ |
| 21 | 2-CH$_3$ |
| 22 | 3-CH$_3$ |
| 23 | 4-CH$_3$ |
| 24 | 2,3-(CH$_3$)$_2$ |
| 25 | 2,4-(CH$_3$)$_2$ |
| 26 | 2,5-(CH$_3$)$_2$ |
| 27 | 2,6-(CH$_3$)$_2$ |
| 28 | 3,5-(CH$_3$)$_2$ |
| 29 | 3-Cl,5-CH$_3$ |
| 30 | 3-F,5-CH$_3$ |
| 31 | 3-F,5-Cl |
| 32 | 2-CF$_3$ |
| 33 | 3-CF$_3$ |
| 34 | 4-CF$_3$ |
| 35 | 2-CN |
| 36 | 3-CN |
| 37 | 4-CN |
| 38 | 2-SMe |
| 39 | 3-SMe |
| 40 | 4-SMe |
| 41 | 2-SO$_2$Me |
| 42 | 3-SO$_2$Me |
| 43 | 4-SO$_2$Me |
| 44 | 2-Br |
| 45 | 3-Br |
| 46 | 4-Br |
| 47 | 2-OH |
| 48 | 3-OH |
| 49 | 4-OH |
| 50 | 2-OMe |
| 51 | 3-OMe |
| 52 | 4-OMe |

TABLE 28

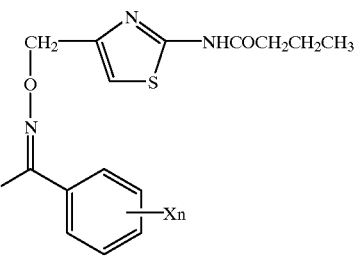

Het B: 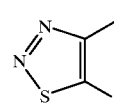

| No | Xn |
|---|---|
| 1 | 2-OPh |
| 2 | 3-OPh |
| 3 | 4-OPh |
| 4 | 2-OCF$_2$H |
| 5 | 3-OCF$_2$H |
| 6 | 4-OCF$_2$H |
| 7 | 2-CO$_2$H |
| 8 | 3-CO$_2$H |
| 9 | 4-CO$_2$H |
| 10 | 2-CO$_2$Me |
| 11 | 3-CO$_2$Me |
| 12 | 2-CF$_2$Cl |
| 13 | 3-CF$_2$Cl |
| 14 | 4-CF$_2$Cl |
| 15 | 2-NO$_2$ |
| 16 | 3-NO$_2$ |
| 17 | 4-NO$_2$ |
| 18 | 2-NH$_2$ |
| 19 | 3-NH$_2$ |
| 20 | 4-NH$_2$ |
| 21 | 4-Ph |
| 22 | 2-OCF$_3$ |
| 23 | 3-OCF$_3$ |
| 24 | 4-OCF$_3$ |
| 25 | 2,4-(CF$_3$)$_2$ |
| 26 | 2,5-(CF$_3$)$_2$ |
| 27 | 2,6-(CF$_3$)$_2$ |
| 28 | 3,4-(CF$_3$)$_2$ |
| 29 | 3,5-(CF$_3$)$_2$ |
| 30 | 2-Me,4-Cl |
| 31 | 2-Me,3-Cl |
| 32 | 2-Cl,4-Me |
| 33 | 2-Et,6-Me |
| 34 | 2-Cl,5-CF$_3$ |
| 35 | 2-Cl,6-F |
| 36 | 2,4,6-(Me)$_3$ |

TABLE 29

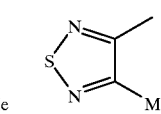

Het B: 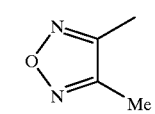

| No | Xn |
|---|---|
| 1 | 2-Cl |
| 2 | 3-Cl |
| 3 | 4-Cl |
| 4 | 2,3-(Cl)$_2$ |
| 5 | 2,4-(Cl)$_2$ |
| 6 | 2,5-(Cl)$_2$ |
| 7 | 2,6-(Cl)$_2$ |
| 8 | 3,4-(Cl)$_2$ |
| 9 | 3,5-(Cl)$_2$ |
| 10 | 2,4,6-(Cl)$_3$ |
| 11 | 2-F |
| 12 | 3-F |
| 13 | 4-F |
| 14 | 2,3-(F)$_2$ |
| 15 | 2,4-(F)$_2$ |
| 16 | 2,5-(F)$_2$ |
| 17 | 2,6-(F)$_2$ |
| 18 | 3,4-(F)$_2$ |
| 19 | 3,4-(F)$_2$ |
| 20 | 2,4,6-(F)$_3$ |
| 21 | 2-CH$_3$ |
| 22 | 3-CH$_3$ |
| 23 | 4-CH$_3$ |
| 24 | 2,3-(CH$_3$)$_2$ |
| 25 | 2,4-(CH$_3$)$_2$ |
| 26 | 2,5-(CH$_3$)$_2$ |
| 27 | 2,6-(CH$_3$)$_2$ |
| 28 | 3,5-(CH$_3$)$_2$ |
| 29 | 3-Cl,5-CH$_3$ |
| 30 | 3-F,5-CH$_3$ |
| 31 | 3-F,5-Cl |
| 32 | 2-CF$_3$ |
| 33 | 3-CF$_3$ |
| 34 | 4-CF$_3$ |
| 35 | 2-CN |
| 36 | 3-CN |
| 37 | 4-CN |
| 38 | 2-SMe |
| 39 | 3-SMe |
| 40 | 4-SMe |
| 41 | 2-SO$_2$Me |
| 42 | 3-SO$_2$Me |
| 43 | 4-SO$_2$Me |
| 44 | 2-Br |
| 45 | 3-Br |
| 46 | 4-Br |
| 47 | 2-OH |
| 48 | 3-OH |
| 49 | 4-OH |
| 50 | 2-OMe |
| 51 | 3-OMe |
| 52 | 4-OMe |

TABLE 30

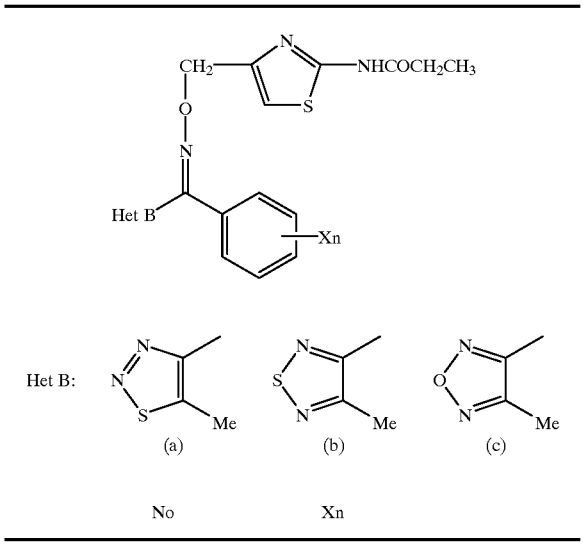

Het B: (a), (b), (c)

| No | Xn |
|----|----|
| 1  | 2-OPh |
| 2  | 3-OPh |
| 3  | 4-OPh |
| 4  | 2-OCF$_2$H |
| 5  | 3-OCF$_2$H |
| 6  | 4-OCF$_2$H |
| 7  | 2-CO$_2$H |
| 8  | 3-CO$_2$H |
| 9  | 4-CO$_2$H |
| 10 | 2-CO$_2$Me |
| 11 | 3-CO$_2$Me |
| 12 | 2-CF$_2$Cl |
| 13 | 3-CF$_2$Cl |
| 14 | 4-CF$_2$Cl |
| 15 | 2-NO$_2$ |
| 16 | 3-NO$_2$ |
| 17 | 4-NO$_2$ |
| 18 | 2-NH$_2$ |
| 19 | 3-NH$_2$ |
| 20 | 4-NH$_2$ |
| 21 | 4-Ph |
| 22 | 2-OCF$_3$ |
| 23 | 3-OCF$_3$ |
| 24 | 4-OCF$_3$ |
| 25 | 2,4-(CF$_3$)$_2$ |
| 26 | 2,5-(CF$_3$)$_2$ |
| 27 | 2,6-(CF$_3$)$_2$ |
| 28 | 3,4-(CF$_3$)$_2$ |
| 29 | 3,5-(CF$_3$)$_2$ |
| 30 | 2-Me,4-Cl |
| 31 | 2-Me,3-Cl |
| 32 | 2-Cl,4-Me |
| 33 | 2-Et,6-Me |
| 34 | 2-Cl,5-CF$_3$ |
| 35 | 2-Cl,6-F |
| 36 | 2,4,6-(Me)$_3$ |

TABLE 31

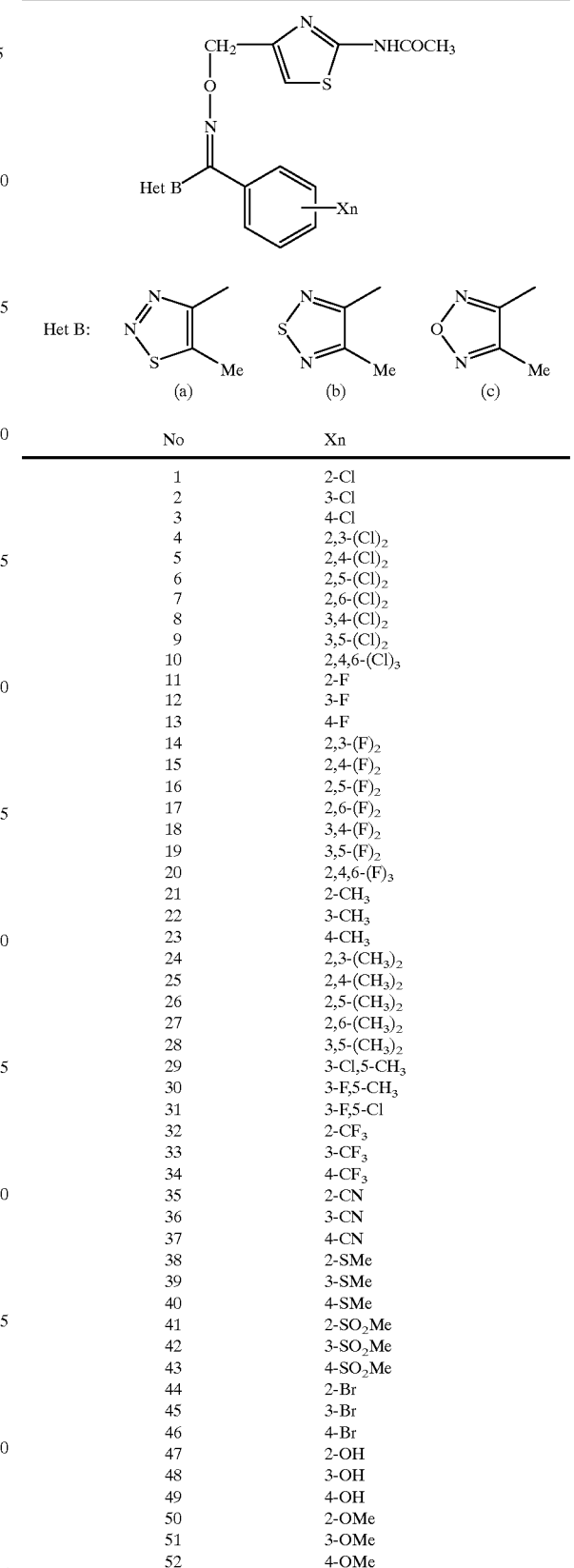

Het B: (a), (b), (c)

| No | Xn |
|----|----|
| 1  | 2-Cl |
| 2  | 3-Cl |
| 3  | 4-Cl |
| 4  | 2,3-(Cl)$_2$ |
| 5  | 2,4-(Cl)$_2$ |
| 6  | 2,5-(Cl)$_2$ |
| 7  | 2,6-(Cl)$_2$ |
| 8  | 3,4-(Cl)$_2$ |
| 9  | 3,5-(Cl)$_2$ |
| 10 | 2,4,6-(Cl)$_3$ |
| 11 | 2-F |
| 12 | 3-F |
| 13 | 4-F |
| 14 | 2,3-(F)$_2$ |
| 15 | 2,4-(F)$_2$ |
| 16 | 2,5-(F)$_2$ |
| 17 | 2,6-(F)$_2$ |
| 18 | 3,4-(F)$_2$ |
| 19 | 3,5-(F)$_2$ |
| 20 | 2,4,6-(F)$_3$ |
| 21 | 2-CH$_3$ |
| 22 | 3-CH$_3$ |
| 23 | 4-CH$_3$ |
| 24 | 2,3-(CH$_3$)$_2$ |
| 25 | 2,4-(CH$_3$)$_2$ |
| 26 | 2,5-(CH$_3$)$_2$ |
| 27 | 2,6-(CH$_3$)$_2$ |
| 28 | 3,5-(CH$_3$)$_2$ |
| 29 | 3-Cl,5-CH$_3$ |
| 30 | 3-F,5-CH$_3$ |
| 31 | 3-F,5-Cl |
| 32 | 2-CF$_3$ |
| 33 | 3-CF$_3$ |
| 34 | 4-CF$_3$ |
| 35 | 2-CN |
| 36 | 3-CN |
| 37 | 4-CN |
| 38 | 2-SMe |
| 39 | 3-SMe |
| 40 | 4-SMe |
| 41 | 2-SO$_2$Me |
| 42 | 3-SO$_2$Me |
| 43 | 4-SO$_2$Me |
| 44 | 2-Br |
| 45 | 3-Br |
| 46 | 4-Br |
| 47 | 2-OH |
| 48 | 3-OH |
| 49 | 4-OH |
| 50 | 2-OMe |
| 51 | 3-OMe |
| 52 | 4-OMe |

TABLE 32

Structure: CH₂ group connected to thiazole (with NHCOCH₃), linked via O-N=C to HetB and phenyl-Xn Het B:
(a) 4-methyl-1,2,3-thiadiazol-5-yl (S,N,N arrangement with Me)
(b) 3-methyl-1,2,5-thiadiazol-4-yl
(c) 3-methyl-1,2,5-oxadiazol-4-yl

| No | Xn |
| --- | --- |
| 1 | 2-OPh |
| 2 | 3-OPh |
| 3 | 4-OPh |
| 4 | 2-OCF₂H |
| 5 | 3-OCF₂H |
| 6 | 4-OCF₂H |
| 7 | 2-CO₂H |
| 8 | 3-CO₂H |
| 9 | 4-CO₂H |
| 10 | 2-CO₂Me |
| 11 | 3-CO₂Me |
| 12 | 2-CF₂Cl |
| 13 | 3-CF₂Cl |
| 14 | 4-CF₂Cl |
| 15 | 2-NO₂ |
| 16 | 3-NO₂ |
| 17 | 4-NO₂ |
| 18 | 2-NH₂ |
| 19 | 3-NH₂ |
| 20 | 4-NH₂ |
| 21 | 4-Ph |
| 22 | 2-OCF₃ |
| 23 | 3-OCF₃ |
| 24 | 4-OCF₃ |
| 25 | 2,4-(CF₃)₂ |
| 26 | 2,5-(CF₃)₂ |
| 27 | 2,6-(CF₃)₂ |
| 28 | 3,4-(CF₃)₂ |
| 29 | 3,5-(CF₃)₂ |
| 30 | 2-Me, 4-Cl |
| 31 | 2-Me, 3-Cl |
| 32 | 2-Cl, 4-Me |
| 33 | 2-Et, 6-Me |
| 34 | 2-Cl, 5-CF₃ |
| 35 | 2-Cl, 6-F |
| 36 | 2,4,6-(Me)₃ |

TABLE 33

Structure: CH₂ group connected to thiazole (with NHCHO), linked via O-N=C to HetB and phenyl-Xn Het B:
(a) 4-methyl-1,2,3-thiadiazol-5-yl-Me
(b) 3-methyl-1,2,5-thiadiazol-4-yl-Me
(c) 3-methyl-1,2,5-oxadiazol-4-yl-Me

| No | Xn |
| --- | --- |
| 1 | 2-Cl |
| 2 | 3-Cl |
| 3 | 4-Cl |
| 4 | 2,3-(Cl)₂ |
| 5 | 2,4-(Cl)₂ |
| 6 | 2,5-(Cl)₂ |
| 7 | 2,6-(Cl)₂ |
| 8 | 3,4-(Cl)₂ |
| 9 | 3,5-(Cl)₂ |
| 10 | 2,4,6-(Cl)₃ |
| 11 | 2-F |
| 12 | 3-F |
| 13 | 4-F |
| 14 | 2,3-(F)₂ |
| 15 | 2,4-(F)₂ |
| 16 | 2,5-(F)₂ |
| 17 | 2,6-(F)₂ |
| 18 | 3,4-(F)₂ |
| 19 | 3,5-(F)₂ |
| 20 | 2,4,6-(F)₃ |
| 21 | 2-CH₃ |
| 22 | 3-CH₃ |
| 23 | 4-CH₃ |
| 24 | 2,3-(CH₃)₂ |
| 25 | 2,4-(CH₃)₂ |
| 26 | 2,5-(CH₃)₂ |
| 27 | 2,6-(CH₃)₂ |
| 28 | 3,5-(CH₃)₂ |
| 29 | 3-Cl, 5-CH₃ |
| 30 | 3-F, 5-CH₃ |
| 31 | 3-F, 5-Cl |
| 32 | 2-CF₃ |
| 33 | 3-CF₃ |
| 34 | 4-CF₃ |
| 35 | 2-CN |
| 36 | 3-CN |
| 37 | 4-CN |
| 38 | 2-SMe |
| 39 | 3-SMe |
| 40 | 4-SMe |
| 41 | 2-SO₂Me |
| 42 | 3-SO₂Me |
| 43 | 4-SO₂Me |
| 44 | 2-Br |
| 45 | 3-Br |
| 46 | 4-Br |
| 47 | 2-OH |
| 48 | 3-OH |
| 49 | 4-OH |
| 50 | 2-OMe |
| 51 | 3-OMe |
| 52 | 4-OMe |

TABLE 34

Structure: Het B-C(=N-O-CH2-[thiazole-2-NHCHO])-phenyl-Xn

Het B:
(a) 4-methyl-1,2,3-thiadiazol-5-yl (Me at 5-position)
(b) 4-methyl-1,2,5-thiadiazol-3-yl
(c) 4-methyl-1,2,5-oxadiazol-3-yl

| No | Xn |
|---|---|
| 1 | 2-OPh |
| 2 | 3-OPh |
| 3 | 4-OPh |
| 4 | 2-OCF$_2$H |
| 5 | 3-OCF$_2$H |
| 6 | 4-OCF$_2$H |
| 7 | 2-CO$_2$H |
| 8 | 3-CO$_2$H |
| 9 | 4-CO$_2$H |
| 10 | 2-CO$_2$Me |
| 11 | 3-CO$_2$Me |
| 12 | 2-CF$_2$Cl |
| 13 | 3-CF$_2$Cl |
| 14 | 4-CF$_2$Cl |
| 15 | 2-NO$_2$ |
| 16 | 3-NO$_2$ |
| 17 | 4-NO$_2$ |
| 18 | 2-NH$_2$ |
| 19 | 3-NH$_2$ |
| 20 | 4-NH$_2$ |
| 21 | 4-Ph |
| 22 | 2-OCF$_3$ |
| 23 | 3-OCF$_3$ |
| 24 | 4-OCF$_3$ |
| 25 | 2,4-(CF$_3$)$_2$ |
| 26 | 2,5-(CF$_3$)$_2$ |
| 27 | 2,6-(CF$_3$)$_2$ |
| 28 | 3,4-(CF$_3$)$_2$ |
| 29 | 3,5-(CF$_3$)$_2$ |
| 30 | 2-Me, 4-Cl |
| 31 | 2-Me, 3-Cl |
| 32 | 2-Cl, 4-Me |
| 33 | 2-Et, 6-Me |
| 34 | 2-Cl, 5-CF$_3$ |
| 35 | 2-Cl, 6-F |
| 36 | 2,4,6-(Me)$_3$ |

TABLE 35

Structure: Het B-C(=N-O-CH2-[thiazole-2-NH2])-phenyl-Xn

Het B:
(a) 4-methyl-1,2,3-thiadiazol-5-yl (Me at 5-position)
(b) 4-methyl-1,2,5-thiadiazol-3-yl
(c) 4-methyl-1,2,5-oxadiazol-3-yl

| No | Xn |
|---|---|
| 1 | 2-Cl |
| 2 | 3-Cl |
| 3 | 4-Cl |
| 4 | 2,3-(Cl)$_2$ |
| 5 | 2,4-(Cl)$_2$ |
| 6 | 2,5-(Cl)$_2$ |
| 7 | 2,6-(Cl)$_2$ |
| 8 | 3,4-(Cl)$_2$ |
| 9 | 3,5-(Cl)$_2$ |
| 10 | 2,4,6-(Cl)$_3$ |
| 11 | 2-F |
| 12 | 3-F |
| 13 | 4-F |
| 14 | 2,3-(F)$_2$ |
| 15 | 2,4-(F)$_2$ |
| 16 | 2,5-(F)$_2$ |
| 17 | 2,6-(F)$_2$ |
| 18 | 3,4-(F)$_2$ |
| 19 | 3,5-(F)$_2$ |
| 20 | 2,4,6-(F)$_3$ |
| 21 | 2-CH$_3$ |
| 22 | 3-CH$_3$ |
| 23 | 4-CH$_3$ |
| 24 | 2,3-(CH$_3$)$_2$ |
| 25 | 2,4-(CH$_3$)$_2$ |
| 26 | 2,5-(CH$_3$)$_2$ |
| 27 | 2,6-(CH$_3$)$_2$ |
| 28 | 3,5-(CH$_3$)$_2$ |
| 29 | 3-Cl, 5-CH$_3$ |
| 30 | 3-F, 5-CH$_3$ |
| 31 | 3-F, 5-Cl |
| 32 | 2-CF$_3$ |
| 33 | 3-CF$_3$ |
| 34 | 4-CF$_3$ |
| 35 | 2-CN |
| 36 | 3-CN |
| 37 | 4-CN |
| 38 | 2-SMe |
| 39 | 3-SMe |
| 40 | 4-SMe |
| 41 | 2-SO$_2$Me |
| 42 | 3-SO$_2$Me |
| 43 | 4-SO$_2$Me |
| 44 | 2-Br |
| 45 | 3-Br |
| 46 | 4-Br |
| 47 | 2-OH |
| 48 | 3-OH |
| 49 | 4-OH |
| 50 | 2-OMe |
| 51 | 3-OMe |
| 52 | 4-OMe |

TABLE 36

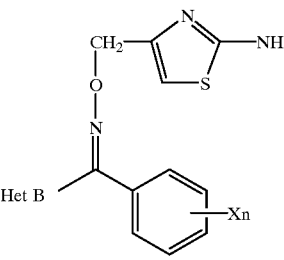

No | Xn
--- | ---
1 | 2-OPh
2 | 3-OPh
3 | 4-OPh
4 | 2-OCF$_2$H
5 | 3-OCF$_2$H
6 | 4-OCF$_2$H
7 | 2-CO$_2$H
8 | 3-CO$_2$H
9 | 4-CO$_2$H
10 | 2-CO$_2$Me
11 | 3-CO$_2$Me
12 | 2-CF$_2$Cl
13 | 3-CF$_2$Cl
14 | 4-CF$_2$Cl
15 | 2-NO$_2$
16 | 3-NO$_2$
17 | 4-NO$_2$
18 | 2-NH$_2$
19 | 3-NH$_2$
20 | 4-NH$_2$
21 | 4-Ph
22 | 2-OCF$_3$
23 | 3-OCF$_3$
24 | 4-OCF$_3$
25 | 2,4-(CF$_3$)$_2$
26 | 2,5-(CF$_3$)$_2$
27 | 2,6-(CF$_3$)$_2$
28 | 3,4-(CF$_3$)$_2$
29 | 3,5-(CF$_3$)$_2$
30 | 2-Me, 4-Cl
31 | 2-Me, 3-Cl
32 | 2-Cl, 4-Me
33 | 2-Et, 6-Me
34 | 2-Cl, 5-CF$_3$
35 | 2-Cl, 6-F
36 | 2,4,6-(Me)$_3$

TABLE 37

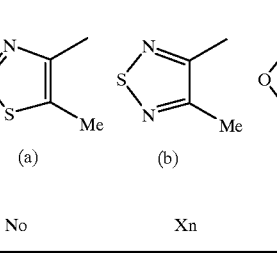

No | Xn
--- | ---
1 | 2-Cl
2 | 3-Cl
3 | 4-Cl
4 | 2,3-(Cl)$_2$
5 | 2,4-(Cl)$_2$
6 | 2,5-(Cl)$_2$
7 | 2,6-(Cl)$_2$
8 | 3,4-(Cl)$_2$
9 | 3,5-(Cl)$_2$
10 | 2,4,6-(Cl)$_3$
11 | 2-F
12 | 3-F
13 | 4-F
14 | 2,3-(F)$_2$
15 | 2,4-(F)$_2$
16 | 2,5-(F)$_2$
17 | 2,6-(F)$_2$
18 | 3,4-(F)$_2$
19 | 3,5-(F)$_2$
20 | 2,4,6-(F)$_3$
21 | 2-CH$_3$
22 | 3-CH$_3$
23 | 4-CH$_3$
24 | 2,3-(CH$_3$)$_2$
25 | 2,4-(CH$_3$)$_2$
26 | 2,5-(CH$_3$)$_2$
27 | 2,6-(CH$_3$)$_2$
28 | 3,5-(CH$_3$)$_2$
29 | 3-Cl, 5-CH$_3$
30 | 3-F, 5-CH$_3$
31 | 3-F, 5-Cl
32 | 2-CF$_3$
33 | 3-CF$_3$
34 | 4-CF$_3$
35 | 2-CN
36 | 3-CN
37 | 4-CN
38 | 2-SMe
39 | 3-SMe
40 | 4-SMe
41 | 2-SO$_2$Me
42 | 3-SO$_2$Me
43 | 4-SO$_2$Me
44 | 2-Br
45 | 3-Br
46 | 4-Br
47 | 2-OH
48 | 3-OH
49 | 4-OH
50 | 2-OMe
51 | 3-OMe
52 | 4-OMe

TABLE 38

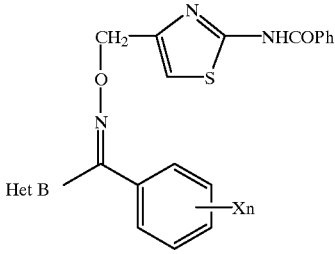

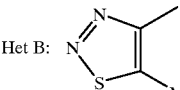

| No | Xn |
|---|---|
| 1 | 2-OPh |
| 2 | 3-OPh |
| 3 | 4-OPh |
| 4 | 2-OCF$_2$H |
| 5 | 3-OCF$_2$H |
| 6 | 4-OCF$_2$H |
| 7 | 2-CO$_2$H |
| 8 | 3-CO$_2$H |
| 9 | 4-CO$_2$H |
| 10 | 2-CO$_2$Me |
| 11 | 3-CO$_2$Me |
| 12 | 2-CF$_2$Cl |
| 13 | 3-CF$_2$Cl |
| 14 | 4-CF$_2$Cl |
| 15 | 2-NO$_2$ |
| 16 | 3-NO$_2$ |
| 17 | 4-NO$_2$ |
| 18 | 2-NH$_2$ |
| 19 | 3-NH$_2$ |
| 20 | 4-NH$_2$ |
| 21 | 4-Ph |
| 22 | 2-OCF$_3$ |
| 23 | 3-OCF$_3$ |
| 24 | 4-OCF$_3$ |
| 25 | 2,4-(CF$_3$)$_2$ |
| 26 | 2,5-(CF$_3$)$_2$ |
| 27 | 2,6-(CF$_3$)$_2$ |
| 28 | 3,4-(CF$_3$)$_2$ |
| 29 | 3,5-(CF$_3$)$_2$ |
| 30 | 2-Me, 4-Cl |
| 31 | 2-Me, 3-Cl |
| 32 | 2-Cl, 4-Me |
| 33 | 2-Et, 6-Me |
| 34 | 2-Cl, 5-CF$_3$ |
| 35 | 2-Cl, 6-F |
| 36 | 2,4,6-(Me)$_3$ |

TABLE 39

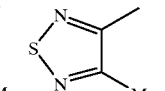

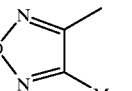

| No | Xn |
|---|---|
| 1 | 2-Cl |
| 2 | 3-Cl |
| 3 | 4-Cl |
| 4 | 2,3-(Cl)$_2$ |
| 5 | 2,4-(Cl)$_2$ |
| 6 | 2,5-(Cl)$_2$ |
| 7 | 2,6-(Cl)$_2$ |
| 8 | 3,4-(Cl)$_2$ |
| 9 | 3,5-(Cl)$_2$ |
| 10 | 2,4,6-(Cl)$_3$ |
| 11 | 2-F |
| 12 | 3-F |
| 13 | 4-F |
| 14 | 2,3-(F)$_2$ |
| 15 | 2,4-(F)$_2$ |
| 16 | 2,5-(F)$_2$ |
| 17 | 2,6-(F)$_2$ |
| 18 | 3,4-(F)$_2$ |
| 19 | 3,5-(F)$_2$ |
| 20 | 2,4,6-(F)$_3$ |
| 21 | 2-CH$_3$ |
| 22 | 3-CH$_3$ |
| 23 | 4-CH$_3$ |
| 24 | 2,3-(CH$_3$)$_2$ |
| 25 | 2,4-(CH$_3$)$_2$ |
| 26 | 2,5-(CH$_3$)$_2$ |
| 27 | 2,6-(CH$_3$)$_2$ |
| 28 | 3,5-(CH$_3$)$_2$ |
| 29 | 3-Cl, 5-CH$_3$ |
| 30 | 3-F, 5-CH$_3$ |
| 31 | 3-F, 5-Cl |
| 32 | 2-CF$_3$ |
| 33 | 3-CF$_3$ |
| 34 | 4-CF$_3$ |
| 35 | 2-CN |
| 36 | 3-CN |
| 37 | 4-CN |
| 38 | 2-SMe |
| 39 | 3-SMe |
| 40 | 4-SMe |
| 41 | 2-SO$_2$Me |
| 42 | 3-SO$_2$Me |
| 43 | 4-SO$_2$Me |
| 44 | 2-Br |
| 45 | 3-Br |
| 46 | 4-Br |
| 47 | 2-OH |
| 48 | 3-OH |
| 49 | 4-OH |
| 50 | 2-OMe |
| 51 | 3-OMe |
| 52 | 4-OMe |

TABLE 40

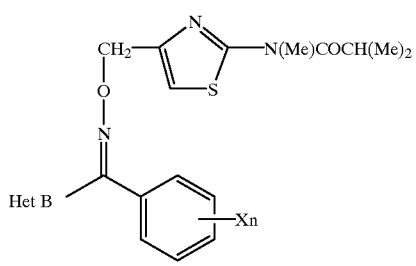

| No | Xn |
|---|---|
| 1 | 2-OPh |
| 2 | 3-OPh |
| 3 | 4-OPh |
| 4 | 2-OCF$_2$H |
| 5 | 3-OCF$_2$H |
| 6 | 4-OCF$_2$H |
| 7 | 2-CO$_2$H |
| 8 | 3-CO$_2$H |
| 9 | 4-CO$_2$H |
| 10 | 2-CO$_2$Me |
| 11 | 3-CO$_2$Me |
| 12 | 2-CF$_2$Cl |
| 13 | 3-CF$_2$Cl |
| 14 | 4-CF$_2$Cl |
| 15 | 2-NO$_2$ |
| 16 | 3-NO$_2$ |
| 17 | 4-NO$_2$ |
| 18 | 2-NH$_2$ |
| 19 | 3-NH$_2$ |
| 20 | 4-NH$_2$ |
| 21 | 4-Ph |
| 22 | 2-OCF$_3$ |
| 23 | 3-OCF$_3$ |
| 24 | 4-OCF$_3$ |
| 25 | 2,4-(CF$_3$)$_2$ |
| 26 | 2,5-(CF$_3$)$_2$ |
| 27 | 2,6-(CF$_3$)$_2$ |
| 28 | 3,4-(CF$_3$)$_2$ |
| 29 | 3,5-(CF$_3$)$_2$ |
| 30 | 2-Me, 4-Cl |
| 31 | 2-Me, 3-Cl |
| 32 | 2-Cl, 4-Me |
| 33 | 2-Et, 6-Me |
| 34 | 2-Cl, 5-CF$_3$ |
| 35 | 2-Cl, 6-F |
| 36 | 2,4,6-(Me)$_3$ |

TABLE 41

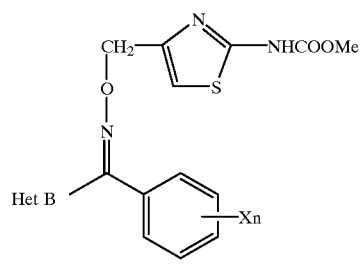

| No | Xn |
|---|---|
| 1 | 2-Cl |
| 2 | 3-Cl |
| 3 | 4-Cl |
| 4 | 2,3-(Cl)$_2$ |
| 5 | 2,4-(Cl)$_2$ |
| 6 | 2,5-(Cl)$_2$ |
| 7 | 2,6-(Cl)$_2$ |
| 8 | 3,4-(Cl)$_2$ |
| 9 | 3,5-(Cl)$_2$ |
| 10 | 2,4,6-(Cl)$_3$ |
| 11 | 2-F |
| 12 | 3-F |
| 13 | 4-F |
| 14 | 2,3-(F)$_2$ |
| 15 | 2,4-(F)$_2$ |
| 16 | 2,5-(F)$_2$ |
| 17 | 2,6-(F)$_2$ |
| 18 | 3,4-(F)$_2$ |
| 19 | 3,5-(F)$_2$ |
| 20 | 2,4,6-(F)$_3$ |
| 21 | 2-CH$_3$ |
| 22 | 3-CH$_3$ |
| 23 | 4-CH$_3$ |
| 24 | 2,3-(CH$_3$)$_2$ |
| 25 | 2,4-(CH$_3$)$_2$ |
| 26 | 2,5-(CH$_3$)$_2$ |
| 27 | 2,6-(CH$_3$)$_2$ |
| 28 | 3,5-(CH$_3$)$_2$ |
| 29 | 3-Cl, 5-CH$_3$ |
| 30 | 3-F, 5-CH$_3$ |
| 31 | 3-F, 5-Cl |
| 32 | 2-CF$_3$ |
| 33 | 3-CF$_3$ |
| 34 | 4-CF$_3$ |
| 35 | 2-CN |
| 36 | 3-CN |
| 37 | 4-CN |
| 38 | 2-SMe |
| 39 | 3-SMe |
| 40 | 4-SMe |
| 41 | 2-SO$_2$Me |
| 42 | 3-SO$_2$Me |
| 43 | 4-SO$_2$Me |
| 44 | 2-Br |
| 45 | 3-Br |
| 46 | 4-Br |
| 47 | 2-OH |
| 48 | 3-OH |
| 49 | 4-OH |
| 50 | 2-OMe |
| 51 | 3-OMe |
| 52 | 4-OMe |

TABLE 42

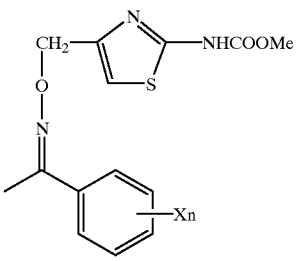

| No | Xn |
|---|---|
| 1 | 2-OPh |
| 2 | 3-OPh |
| 3 | 4-OPh |
| 4 | 2-OCF₂H |
| 5 | 3-OCF₂H |
| 6 | 4-OCF₂H |
| 7 | 2-CO₂H |
| 8 | 3-CO₂H |
| 9 | 4-CO₂H |
| 10 | 2-CO₂Me |
| 11 | 3-CO₂Me |
| 12 | 2-CF₂Cl |
| 13 | 3-CF₂Cl |
| 14 | 4-CF₂Cl |
| 15 | 2-NO₂ |
| 16 | 3-NO₂ |
| 17 | 4-NO₂ |
| 18 | 2-NH₂ |
| 19 | 3-NH₂ |
| 20 | 4-NH₂ |
| 21 | 4-Ph |
| 22 | 2-OCF₃ |
| 23 | 3-OCF₃ |
| 24 | 4-OCF₃ |
| 25 | 2,4-(CF₃)₂ |
| 26 | 2,5-(CF₃)₂ |
| 27 | 2,6-(CF₃)₂ |
| 28 | 3,4-(CF₃)₂ |
| 29 | 3,5-(CF₃)₂ |
| 30 | 2-Me, 4-Cl |
| 31 | 2-Me, 3-Cl |
| 32 | 2-Cl, 4-Me |
| 33 | 2-Et, 6-Me |
| 34 | 2-Cl, 5-CF₃ |
| 35 | 2-Cl, 6-F |
| 36 | 2,4,6-(Me)₃ |

TABLE 43

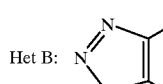

| No | Xn |
|---|---|
| 1 | 2-Cl |
| 2 | 3-Cl |
| 3 | 4-Cl |
| 4 | 2,3-(Cl)₂ |
| 5 | 2,4-(Cl)₂ |
| 6 | 2,5-(Cl)₂ |
| 7 | 2,6-(Cl)₂ |
| 8 | 3,4-(Cl)₂ |
| 9 | 3,5-(Cl)₂ |
| 10 | 2,4,6-(Cl)₃ |
| 11 | 2-F |
| 12 | 3-F |
| 13 | 4-F |
| 14 | 2,3-(F)₂ |
| 15 | 2,4-(F)₂ |
| 16 | 2,5-(F)₂ |
| 17 | 2,6-(F)₂ |
| 18 | 3,4-(F)₂ |
| 19 | 3,5-(F)₂ |
| 20 | 2,4,6-(F)₃ |
| 21 | 2-CH₃ |
| 22 | 3-CH₃ |
| 23 | 4-CH₃ |
| 24 | 2,3-(CH₃)₂ |
| 25 | 2,4-(CH₃)₂ |
| 26 | 2,5-(CH₃)₂ |
| 27 | 2,6-(CH₃)₂ |
| 28 | 3,5-(CH₃)₂ |
| 29 | 3-Cl, 5-CH₃ |
| 30 | 3-F, 5-CH₃ |
| 31 | 3-F, 5-Cl |
| 32 | 2-CF₃ |
| 33 | 3-CF₃ |
| 34 | 4-CF₃ |
| 35 | 2-CN |
| 36 | 3-CN |
| 37 | 4-CN |
| 38 | 2-SMe |
| 39 | 3-SMe |
| 40 | 4-SMe |
| 41 | 2-SO₂Me |
| 42 | 3-SO₂Me |
| 43 | 4-SO₂Me |
| 44 | 2-Br |
| 45 | 3-Br |
| 46 | 4-Br |
| 47 | 2-OH |
| 48 | 3-OH |
| 49 | 4-OH |
| 50 | 2-OMe |
| 51 | 3-OMe |
| 52 | 4-OMe |

TABLE 44

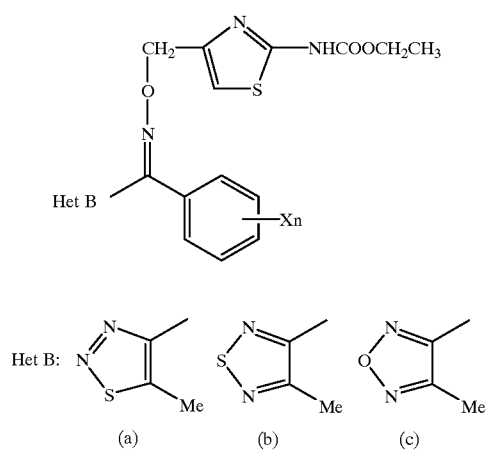

| No | Xn |
|---|---|
| 1 | 2-OPh |
| 2 | 3-OPh |
| 3 | 4-OPh |
| 4 | 2-OCF$_2$H |
| 5 | 3-OCF$_2$H |
| 6 | 4-OCF$_2$H |
| 7 | 2-CO$_2$H |
| 8 | 3-CO$_2$H |
| 9 | 4-CO$_2$H |
| 10 | 2-CO$_2$Me |
| 11 | 3-CO$_2$Me |
| 12 | 2-CF$_2$Cl |
| 13 | 3-CF$_2$Cl |
| 14 | 4-CF$_2$Cl |
| 15 | 2-NO$_2$ |
| 16 | 3-NO$_2$ |
| 17 | 4-NO$_2$ |
| 18 | 2-NH$_2$ |
| 19 | 3-NH$_2$ |
| 20 | 4-NH$_2$ |
| 21 | 4-Ph |
| 22 | 2-OCF$_3$ |
| 23 | 3-OCF$_3$ |
| 24 | 4-OCF$_3$ |
| 25 | 2,4-(CF$_3$)$_2$ |
| 26 | 2,5-(CF$_3$)$_2$ |
| 27 | 2,6-(CF$_3$)$_2$ |
| 28 | 3,4-(CF$_3$)$_2$ |
| 29 | 3,5-(CF$_3$)$_2$ |
| 30 | 2-Me, 4-Cl |
| 31 | 2-Me, 3-Cl |
| 32 | 2-Cl, 4-Me |
| 33 | 2-Et, 6-Me |
| 34 | 2-Cl, 5-CF$_3$ |
| 35 | 2-Cl, 6-F |
| 36 | 2,4,6-(Me)$_3$ |

TABLE 45

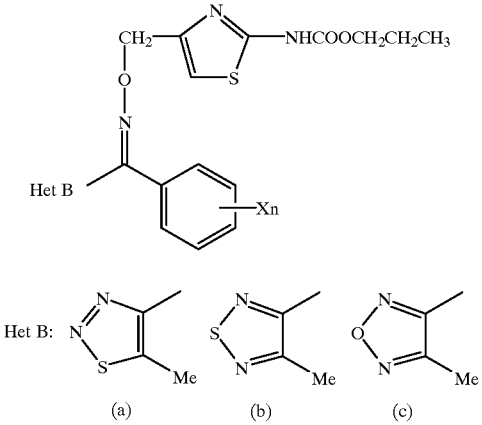

| No | Xn |
|---|---|
| 1 | 2-Cl |
| 2 | 3-Cl |
| 3 | 4-Cl |
| 4 | 2,3-(Cl)$_2$ |
| 5 | 2,4-(Cl)$_2$ |
| 6 | 2,5-(Cl)$_2$ |
| 7 | 2,6-(Cl)$_2$ |
| 8 | 3,4-(Cl)$_2$ |
| 9 | 3,5-(Cl)$_2$ |
| 10 | 2,4,6-(Cl)$_3$ |
| 11 | 2-F |
| 12 | 3-F |
| 13 | 4-F |
| 14 | 2,3-(F)$_2$ |
| 15 | 2,4-(F)$_2$ |
| 16 | 2,5-(F)$_2$ |
| 17 | 2,6-(F)$_2$ |
| 18 | 3,4-(F)$_2$ |
| 19 | 3,5-(F)$_2$ |
| 20 | 2,4,6-(F)$_3$ |
| 21 | 2-CH$_3$ |
| 22 | 3-CH$_3$ |
| 23 | 4-CH$_3$ |
| 24 | 2,3-(CH$_3$)$_2$ |
| 25 | 2,4-(CH$_3$)$_2$ |
| 26 | 2,5-(CH$_3$)$_2$ |
| 27 | 2,6-(CH$_3$)$_2$ |
| 28 | 3,5-(CH$_3$)$_2$ |
| 29 | 3-Cl, 5-CH$_3$ |
| 30 | 3-F, 5-CH$_3$ |
| 31 | 3-F, 5-Cl |
| 32 | 2-CF$_3$ |
| 33 | 3-CF$_3$ |
| 34 | 4-CF$_3$ |
| 35 | 2-CN |
| 36 | 3-CN |
| 37 | 4-CN |
| 38 | 2-SMe |
| 39 | 3-SMe |
| 40 | 4-SMe |
| 41 | 2-SO$_2$Me |
| 42 | 3-SO$_2$Me |
| 43 | 4-SO$_2$Me |
| 44 | 2-Br |
| 45 | 3-Br |
| 46 | 4-Br |
| 47 | 2-OH |
| 48 | 3-OH |
| 49 | 4-OH |
| 50 | 2-OMe |
| 51 | 3-OMe |
| 52 | 4-OMe |

TABLE 46

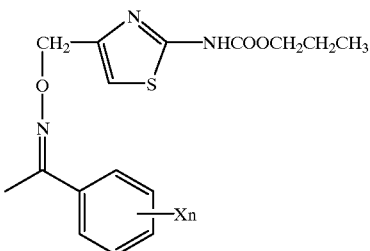

| No | Xn |
|---|---|
| 1 | 2-OPh |
| 2 | 3-OPh |
| 3 | 4-OPh |
| 4 | 2-OCF$_2$H |
| 5 | 3-OCF$_2$H |
| 6 | 4-OCF$_2$H |
| 7 | 2-CO$_2$H |
| 8 | 3-CO$_2$H |
| 9 | 4-CO$_2$H |
| 10 | 2-CO$_2$Me |
| 11 | 3-CO$_2$Me |
| 12 | 2-CF$_2$Cl |
| 13 | 3-CF$_2$Cl |
| 14 | 4-CF$_2$Cl |
| 15 | 2-NO$_2$ |
| 16 | 3-NO$_2$ |
| 17 | 4-NO$_2$ |
| 18 | 2-NH$_2$ |
| 19 | 3-NH$_2$ |
| 20 | 4-NH$_2$ |
| 21 | 4-Ph |
| 22 | 2-OCF$_3$ |
| 23 | 3-OCF$_3$ |
| 24 | 4-OCF$_3$ |
| 25 | 2,4-(CF$_3$)$_2$ |
| 26 | 2,5-(CF$_3$)$_2$ |
| 27 | 2,6-(CF$_3$)$_2$ |
| 28 | 3,4-(CF$_3$)$_2$ |
| 29 | 3,5-(CF$_3$)$_2$ |
| 30 | 2-Me, 4-Cl |
| 31 | 2-Me, 3-Cl |
| 32 | 2-Cl, 4-Me |
| 33 | 2-Et, 6-Me |
| 34 | 2-Cl, 5-CF$_3$ |
| 35 | 2-Cl, 6-F |
| 36 | 2,4,6-(Me)$_3$ |

TABLE 47

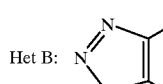

| No | Xn |
|---|---|
| 1 | 2-Cl |
| 2 | 3-Cl |
| 3 | 4-Cl |
| 4 | 2,3-(Cl)$_2$ |
| 5 | 2,4-(Cl)$_2$ |
| 6 | 2,5-(Cl)$_2$ |
| 7 | 2,6-(Cl)$_2$ |
| 8 | 3,4-(Cl)$_2$ |
| 9 | 3,5-(Cl)$_2$ |
| 10 | 2,4,6-(Cl)$_3$ |
| 11 | 2-F |
| 12 | 3-F |
| 13 | 4-F |
| 14 | 2,3-(F)$_2$ |
| 15 | 2,4-(F)$_2$ |
| 16 | 2,5-(F)$_2$ |
| 17 | 2,6-(F)$_2$ |
| 18 | 3,4-(F)$_2$ |
| 19 | 3,5-(F)$_2$ |
| 20 | 2,4,6-(F)$_3$ |
| 21 | 2-CH$_3$ |
| 22 | 3-CH$_3$ |
| 23 | 4-CH$_3$ |
| 24 | 2,3-(CH$_3$)$_2$ |
| 25 | 2,4-(CH$_3$)$_2$ |
| 26 | 2,5-(CH$_3$)$_2$ |
| 27 | 2,6-(CH$_3$)$_2$ |
| 28 | 3,5-(CH$_3$)$_2$ |
| 29 | 3-Cl, 5-CH$_3$ |
| 30 | 3-F, 5-CH$_3$ |
| 31 | 3-F, 5-Cl |
| 32 | 2-CF$_3$ |
| 33 | 3-CF$_3$ |
| 34 | 4-CF$_3$ |
| 35 | 2-CN |
| 36 | 3-CN |
| 37 | 4-CN |
| 38 | 2-SMe |
| 39 | 3-SMe |
| 40 | 4-SMe |
| 41 | 2-SO$_2$Me |
| 42 | 3-SO$_2$Me |
| 43 | 4-SO$_2$Me |
| 44 | 2-Br |
| 45 | 3-Br |
| 46 | 4-Br |
| 47 | 2-OH |
| 48 | 3-OH |
| 49 | 4-OH |
| 50 | 2-OMe |
| 51 | 3-OMe |
| 52 | 4-OMe |

TABLE 48

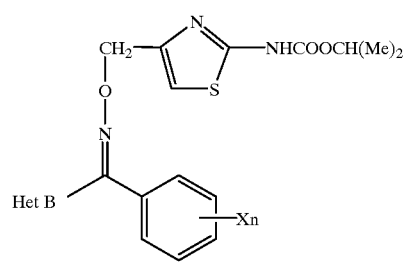

| No | Xn |
|---|---|
| 1 | 2-OPh |
| 2 | 3-OPh |
| 3 | 4-OPh |
| 4 | 2-OCF$_2$H |
| 5 | 3-OCF$_2$H |
| 6 | 4-OCF$_2$H |
| 7 | 2-CO$_2$H |
| 8 | 3-CO$_2$H |
| 9 | 4-CO$_2$H |
| 10 | 2-CO$_2$Me |
| 11 | 3-CO$_2$Me |
| 12 | 2-CF$_2$Cl |
| 13 | 3-CF$_2$Cl |
| 14 | 4-CF$_2$Cl |
| 15 | 2-NO$_2$ |
| 16 | 3-NO$_2$ |
| 17 | 4-NO$_2$ |
| 18 | 2-NH$_2$ |
| 19 | 3-NH$_2$ |
| 20 | 4-NH$_2$ |
| 21 | 4-Ph |
| 22 | 2-OCF$_3$ |
| 23 | 3-OCF$_3$ |
| 24 | 4-OCF$_3$ |
| 25 | 2,4-(CF$_3$)$_2$ |
| 26 | 2,5-(CF$_3$)$_2$ |
| 27 | 2,6-(CF$_3$)$_2$ |
| 28 | 3,4-(CF$_3$)$_2$ |
| 29 | 3,5-(CF$_3$)$_2$ |
| 30 | 2-Me, 4-Cl |
| 31 | 2-Me, 3-Cl |
| 32 | 2-Cl, 4-Me |
| 33 | 2-Et, 6-Me |
| 34 | 2-Cl, 5-CF$_3$ |
| 35 | 2-Cl, 6-F |
| 36 | 2,4,6-(Me)$_3$ |

TABLE 49

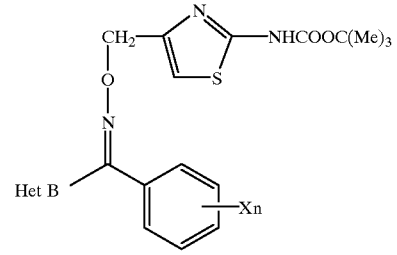

| No | Xn |
|---|---|
| 1 | 2-Cl |
| 2 | 3-Cl |
| 3 | 4-Cl |
| 4 | 2,3-(Cl)$_2$ |
| 5 | 2,4-(Cl)$_2$ |
| 6 | 2,5-(Cl)$_2$ |
| 7 | 2,6-(Cl)$_2$ |
| 8 | 3,4-(Cl)$_2$ |
| 9 | 3,5-(Cl)$_2$ |
| 10 | 2,4,6-(Cl)$_3$ |
| 11 | 2-F |
| 12 | 3-F |
| 13 | 4-F |
| 14 | 2,3-(F)$_2$ |
| 15 | 2,4-(F)$_2$ |
| 16 | 2,5-(F)$_2$ |
| 17 | 2,6-(F)$_2$ |
| 18 | 3,4-(F)$_2$ |
| 19 | 3,5-(F)$_2$ |
| 20 | 2,4,6-(F)$_3$ |
| 21 | 2-CH$_3$ |
| 22 | 3-CH$_3$ |
| 23 | 4-CH$_3$ |
| 24 | 2,3-(CH$_3$)$_2$ |
| 25 | 2,4-(CH$_3$)$_2$ |
| 26 | 2,5-(CH$_3$)$_2$ |
| 27 | 2,6-(CH$_3$)$_2$ |
| 28 | 3,5-(CH$_3$)$_2$ |
| 29 | 3-Cl, 5-CH$_3$ |
| 30 | 3-F, 5-CH$_3$ |
| 31 | 3-F, 5-Cl |
| 32 | 2-CF$_3$ |
| 33 | 3-CF$_3$ |
| 34 | 4-CF$_3$ |
| 35 | 2-CN |
| 36 | 3-CN |
| 37 | 4-CN |
| 38 | 2-SMe |
| 39 | 3-SMe |
| 40 | 4-SMe |
| 41 | 2-SO$_2$Me |
| 42 | 3-SO$_2$Me |
| 43 | 4-SO$_2$Me |
| 44 | 2-Br |
| 45 | 3-Br |
| 46 | 4-Br |
| 47 | 2-OH |
| 48 | 3-OH |
| 49 | 4-OH |
| 50 | 2-OMe |
| 51 | 3-OMe |
| 52 | 4-OMe |

TABLE 50

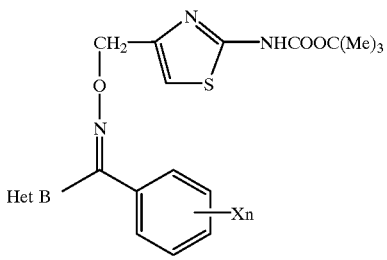

| No | Xn |
|---|---|
| 1 | 2-OPh |
| 2 | 3-OPh |
| 3 | 4-OPh |
| 4 | 2-OCF$_2$H |
| 5 | 3-OCF$_2$H |
| 6 | 4-OCF$_2$H |
| 7 | 2-CO$_2$H |
| 8 | 3-CO$_2$H |
| 9 | 4-CO$_2$H |
| 10 | 2-CO$_2$Me |
| 11 | 3-CO$_2$Me |
| 12 | 2-CF$_2$Cl |
| 13 | 3-CF$_2$Cl |
| 14 | 4-CF$_2$Cl |
| 15 | 2-NO$_2$ |
| 16 | 3-NO$_2$ |
| 17 | 4-NO$_2$ |
| 18 | 2-NH$_2$ |
| 19 | 3-NH$_2$ |
| 20 | 4-NH$_2$ |
| 21 | 4-Ph |
| 22 | 2-OCF$_3$ |
| 23 | 3-OCF$_3$ |
| 24 | 4-OCF$_3$ |
| 25 | 2,4-(CF$_3$)$_2$ |
| 26 | 2,5-(CF$_3$)$_2$ |
| 27 | 2,6-(CF$_3$)$_2$ |
| 28 | 3,4-(CF$_3$)$_2$ |
| 29 | 3,5-(CF$_3$)$_2$ |
| 30 | 2-Me, 4-Cl |
| 31 | 2-Me, 3-Cl |
| 32 | 2-Cl, 4-Me |
| 33 | 2-Et, 6-Me |
| 34 | 2-Cl, 5-CF$_3$ |
| 35 | 2-Cl, 6-F |
| 36 | 2,4,6-(Me)$_3$ |

TABLE 51

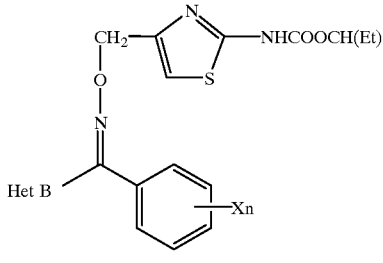

| No | Xn |
|---|---|
| 1 | 2-Cl |
| 2 | 3-Cl |
| 3 | 4-Cl |
| 4 | 2,3-(Cl)$_2$ |
| 5 | 2,4-(Cl)$_2$ |
| 6 | 2,5-(Cl)$_2$ |
| 7 | 2,6-(Cl)$_2$ |
| 8 | 3,4-(Cl)$_2$ |
| 9 | 3,5-(Cl)$_2$ |
| 10 | 2,4,6-(Cl)$_3$ |
| 11 | 2-F |
| 12 | 3-F |
| 13 | 4-F |
| 14 | 2,3-(F)$_2$ |
| 15 | 2,4-(F)$_2$ |
| 16 | 2,5-(F)$_2$ |
| 17 | 2,6-(F)$_2$ |
| 18 | 3,4-(F)$_2$ |
| 19 | 3,5-(F)$_2$ |
| 20 | 2,4,6-(F)$_3$ |
| 21 | 2-CH$_3$ |
| 22 | 3-CH$_3$ |
| 23 | 4-CH$_3$ |
| 24 | 2,3-(CH$_3$)$_2$ |
| 25 | 2,4-(CH$_3$)$_2$ |
| 26 | 2,5-(CH$_3$)$_2$ |
| 27 | 2,6-(CH$_3$)$_2$ |
| 28 | 3,5-(CH$_3$)$_2$ |
| 29 | 3-Cl, 5-CH$_3$ |
| 30 | 3-F, 5-CH$_3$ |
| 31 | 3-F, 5-Cl |
| 32 | 2-CF$_3$ |
| 33 | 3-CF$_3$ |
| 34 | 4-CF$_3$ |
| 35 | 2-CN |
| 36 | 3-CN |
| 37 | 4-CN |
| 38 | 2-SMe |
| 39 | 3-SMe |
| 40 | 4-SMe |
| 41 | 2-SO$_2$Me |
| 42 | 3-SO$_2$Me |
| 43 | 4-SO$_2$Me |
| 44 | 2-Br |
| 45 | 3-Br |
| 46 | 4-Br |
| 47 | 2-OH |
| 48 | 3-OH |
| 49 | 4-OH |
| 50 | 2-OMe |
| 51 | 3-OMe |
| 52 | 4-OMe |

TABLE 52

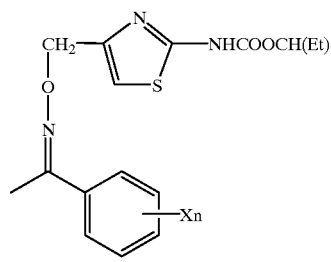

| No | Xn |
|---|---|
| 1 | 2-OPh |
| 2 | 3-OPh |
| 3 | 4-OPh |
| 4 | 2-OCF$_2$H |
| 5 | 3-OCF$_2$H |
| 6 | 4-OCF$_2$H |
| 7 | 2-CO$_2$H |
| 8 | 3-CO$_2$H |
| 9 | 4-CO$_2$H |
| 10 | 2-CO$_2$Me |
| 11 | 3-CO$_2$Me |
| 12 | 2-CF$_2$Cl |
| 13 | 3-CF$_2$Cl |
| 14 | 4-CF$_2$Cl |
| 15 | 2-NO$_2$ |
| 16 | 3-NO$_2$ |
| 17 | 4-NO$_2$ |
| 18 | 2-NH$_2$ |
| 19 | 3-NH$_2$ |
| 20 | 4-NH$_2$ |
| 21 | 4-Ph |
| 22 | 2-OCF$_3$ |
| 23 | 3-OCF$_3$ |
| 24 | 4-OCF$_3$ |
| 25 | 2,4-(CF$_3$)$_2$ |
| 26 | 2,5-(CF$_3$)$_2$ |
| 27 | 2,6-(CF$_3$)$_2$ |
| 28 | 3,4-(CF$_3$)$_2$ |
| 29 | 3,5-(CF$_3$)$_2$ |
| 30 | 2-Me, 4-Cl |
| 31 | 2-Me, 3-Cl |
| 32 | 2-Cl, 4-Me |
| 33 | 2-Et, 6-Me |
| 34 | 2-Cl, 5-CF$_3$ |
| 35 | 2-Cl, 6-F |
| 36 | 2,4,6-(Me)$_3$ |

TABLE 53

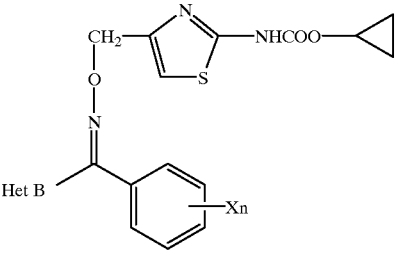

| No | Xn |
|---|---|
| 1 | 2-Cl |
| 2 | 3-Cl |
| 3 | 4-Cl |
| 4 | 2,3-(Cl)$_2$ |
| 5 | 2,4-(Cl)$_2$ |
| 6 | 2,5-(Cl)$_2$ |
| 7 | 2,6-(Cl)$_2$ |
| 8 | 3,4-(Cl)$_2$ |
| 9 | 3,5-(Cl)$_2$ |
| 10 | 2,4,6-(Cl)$_3$ |
| 11 | 2-F |
| 12 | 3-F |
| 13 | 4-F |
| 14 | 2,3-(F)$_2$ |
| 15 | 2,4-(F)$_2$ |
| 16 | 2,5-(F)$_2$ |
| 17 | 2,6-(F)$_2$ |
| 18 | 3,4-(F)$_2$ |
| 19 | 3,5-(F)$_2$ |
| 20 | 2,4,6-(F)$_3$ |
| 21 | 2-CH$_3$ |
| 22 | 3-CH$_3$ |
| 23 | 4-CH$_3$ |
| 24 | 2,3-(CH$_3$)$_2$ |
| 25 | 2,4-(CH$_3$)$_2$ |
| 26 | 2,5-(CH$_3$)$_2$ |
| 27 | 2,6-(CH$_3$)$_2$ |
| 28 | 3,5-(CH$_3$)$_2$ |
| 29 | 3-Cl, 5-CH$_3$ |
| 30 | 3-F, 5-CH$_3$ |
| 31 | 3-F, 5-Cl |
| 32 | 2-CF$_3$ |
| 33 | 3-CF$_3$ |
| 34 | 4-CF$_3$ |
| 35 | 2-CN |
| 36 | 3-CN |
| 37 | 4-CN |
| 38 | 2-SMe |
| 39 | 3-SMe |
| 40 | 4-SMe |
| 41 | 2-SO$_2$Me |
| 42 | 3-SO$_2$Me |
| 43 | 4-SO$_2$Me |
| 44 | 2-Br |
| 45 | 3-Br |
| 46 | 4-Br |
| 47 | 2-OH |
| 48 | 3-OH |
| 49 | 4-OH |
| 50 | 2-OMe |
| 51 | 3-OMe |
| 52 | 4-OMe |

TABLE 54

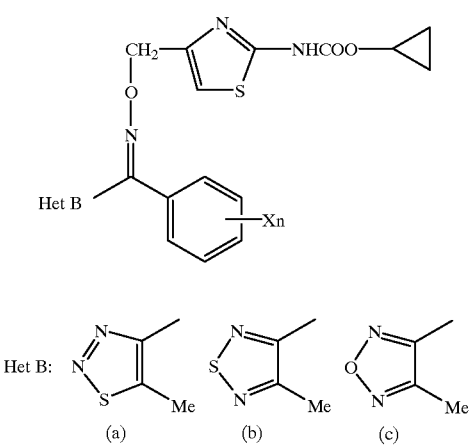

| No | Xn |
| --- | --- |
| 1 | 2-OPh |
| 2 | 3-OPh |
| 3 | 4-OPh |
| 4 | 2-OCF$_2$H |
| 5 | 3-OCF$_2$H |
| 6 | 4-OCF$_2$H |
| 7 | 2-CO$_2$H |
| 8 | 3-CO$_2$H |
| 9 | 4-CO$_2$H |
| 10 | 2-CO$_2$Me |
| 11 | 3-CO$_2$Me |
| 12 | 2-CF$_2$Cl |
| 13 | 3-CF$_2$Cl |
| 14 | 4-CF$_2$Cl |
| 15 | 2-NO$_2$ |
| 16 | 3-NO$_2$ |
| 17 | 4-NO$_2$ |
| 18 | 2-NH$_2$ |
| 19 | 3-NH$_2$ |
| 20 | 4-NH$_2$ |
| 21 | 4-Ph |
| 22 | 2-OCF$_3$ |
| 23 | 3-OCF$_3$ |
| 24 | 4-OCF$_3$ |
| 25 | 2,4-(CF$_3$)$_2$ |
| 26 | 2,5-(CF$_3$)$_2$ |
| 27 | 2,6-(CF$_3$)$_2$ |
| 28 | 3,4-(CF$_3$)$_2$ |
| 29 | 3,5-(CF$_3$)$_2$ |
| 30 | 2-Me, 4-Cl |
| 31 | 2-Me, 3-Cl |
| 32 | 2-Cl, 4-Me |
| 33 | 2-Et, 6-Me |
| 34 | 2-Cl, 5-CF$_3$ |
| 35 | 2-Cl, 6-F |
| 36 | 2,4,6-(Me)$_3$ |

TABLE 55

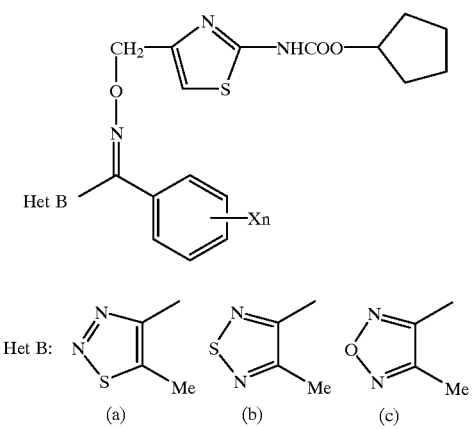

| No | Xn |
| --- | --- |
| 1 | 2-Cl |
| 2 | 3-Cl |
| 3 | 4-Cl |
| 4 | 2,3-(Cl)$_2$ |
| 5 | 2,4-(Cl)$_2$ |
| 6 | 2,5-(Cl)$_2$ |
| 7 | 2,6-(Cl)$_2$ |
| 8 | 3,4-(Cl)$_2$ |
| 9 | 3,5-(Cl)$_2$ |
| 10 | 2,4,6-(Cl)$_3$ |
| 11 | 2-F |
| 12 | 3-F |
| 13 | 4-F |
| 14 | 2,3-(F)$_2$ |
| 15 | 2,4-(F)$_2$ |
| 16 | 2,5-(F)$_2$ |
| 17 | 2,6-(F)$_2$ |
| 18 | 3,4-(F)$_2$ |
| 19 | 3,5-(F)$_2$ |
| 20 | 2,4,6-(F)$_3$ |
| 21 | 2-CH$_3$ |
| 22 | 3-CH$_3$ |
| 23 | 4-CH$_3$ |
| 24 | 2,3-(CH$_3$)$_2$ |
| 25 | 2,4-(CH$_3$)$_2$ |
| 26 | 2,5-(CH$_3$)$_2$ |
| 27 | 2,6-(CH$_3$)$_2$ |
| 28 | 3,5-(CH$_3$)$_2$ |
| 29 | 3-Cl, 5-CH$_3$ |
| 30 | 3-F, 5-CH$_3$ |
| 31 | 3-F, 5-Cl |
| 32 | 2-CF$_3$ |
| 33 | 3-CF$_3$ |
| 34 | 4-CF$_3$ |
| 35 | 2-CN |
| 36 | 3-CN |
| 37 | 4-CN |
| 38 | 2-SMe |
| 39 | 3-SMe |
| 40 | 4-SMe |
| 41 | 2-SO$_2$Me |
| 42 | 3-SO$_2$Me |
| 43 | 4-SO$_2$Me |
| 44 | 2-Br |
| 45 | 3-Br |
| 46 | 4-Br |
| 47 | 2-OH |
| 48 | 3-OH |
| 49 | 4-OH |
| 50 | 2-OMe |
| 51 | 3-OMe |
| 52 | 4-OMe |

TABLE 56

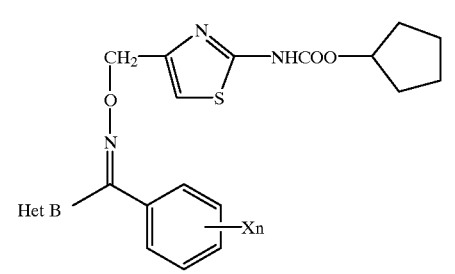

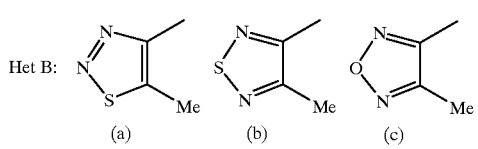

| No | Xn |
|---|---|
| 1 | 2-OPh |
| 2 | 3-OPh |
| 3 | 4-OPh |
| 4 | 2-OCF$_2$H |
| 5 | 3-OCF$_2$H |
| 6 | 4-OCF$_2$H |
| 7 | 2-CO$_2$H |
| 8 | 3-CO$_2$H |
| 9 | 4-CO$_2$H |
| 10 | 2-CO$_2$Me |
| 11 | 3-CO$_2$Me |
| 12 | 2-CF$_2$Cl |
| 13 | 3-CF$_2$Cl |
| 14 | 4-CF$_2$Cl |
| 15 | 2-NO$_2$ |
| 16 | 3-NO$_2$ |
| 17 | 4-NO$_2$ |
| 18 | 2-NH$_2$ |
| 19 | 3-NH$_2$ |
| 20 | 4-NH$_2$ |
| 21 | 4-Ph |
| 22 | 2-OCF$_3$ |
| 23 | 3-OCF$_3$ |
| 24 | 4-OCF$_3$ |
| 25 | 2,4-(CF$_3$)$_2$ |
| 26 | 2,5-(CF$_3$)$_2$ |
| 27 | 2,6-(CF$_3$)$_2$ |
| 28 | 3,4-(CF$_3$)$_2$ |
| 29 | 3,5-(CF$_3$)$_2$ |
| 30 | 2-Me, 4-Cl |
| 31 | 2-Me, 3-Cl |
| 32 | 2-Cl, 4-Me |
| 33 | 2-Et, 6-Me |
| 34 | 2-Cl, 5-CF$_3$ |
| 35 | 2-Cl, 6-F |
| 36 | 2,4,6-(Me)$_3$ |

TABLE 57

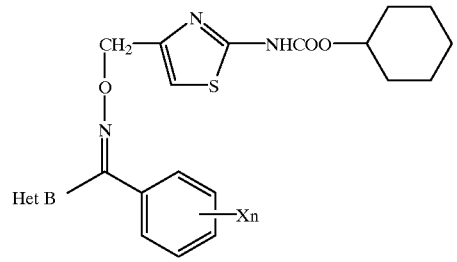

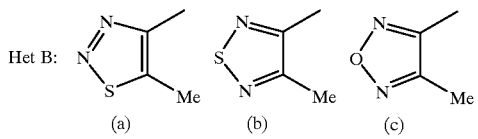

| No | Xn |
|---|---|
| 1 | 2-Cl |
| 2 | 3-Cl |
| 3 | 4-Cl |
| 4 | 2,3-(Cl)$_2$ |
| 5 | 2,4-(Cl)$_2$ |
| 6 | 2,5-(Cl)$_2$ |
| 7 | 2,6-(Cl)$_2$ |
| 8 | 3,4-(Cl)$_2$ |
| 9 | 3,5-(Cl)$_2$ |
| 10 | 2,4,6-(Cl)$_3$ |
| 11 | 2-F |
| 12 | 3-F |
| 13 | 4-F |
| 14 | 2,3-(F)$_2$ |
| 15 | 2,4-(F)$_2$ |
| 16 | 2,5-(F)$_2$ |
| 17 | 2,6-(F)$_2$ |
| 18 | 3,4-(F)$_2$ |
| 19 | 3,5-(F)$_2$ |
| 20 | 2,4,6-(F)$_3$ |
| 21 | 2-CH$_3$ |
| 22 | 3-CH$_3$ |
| 23 | 4-CH$_3$ |
| 24 | 2,3-(CH$_3$)$_2$ |
| 25 | 2,4-(CH$_3$)$_2$ |
| 26 | 2,5-(CH$_3$)$_2$ |
| 27 | 2,6-(CH$_3$)$_2$ |
| 28 | 3,5-(CH$_3$)$_2$ |
| 29 | 3-Cl, 5-CH$_3$ |
| 30 | 3-F, 5-CH$_3$ |
| 31 | 3-F, 5-Cl |
| 32 | 2-CF$_3$ |
| 33 | 3-CF$_3$ |
| 34 | 4-CF$_3$ |
| 35 | 2-CN |
| 36 | 3-CN |
| 37 | 4-CN |
| 38 | 2-SMe |
| 39 | 3-SMe |
| 40 | 4-SMe |
| 41 | 2-SO$_2$Me |
| 42 | 3-SO$_2$Me |
| 43 | 4-SO$_2$Me |
| 44 | 2-Br |
| 45 | 3-Br |
| 46 | 4-Br |
| 47 | 2-OH |
| 48 | 3-OH |
| 49 | 4-OH |
| 50 | 2-OMe |
| 51 | 3-OMe |
| 52 | 4-OMe |

TABLE 58

Structure: Het B−C(=N−O−CH2−[thiazole-4-yl]−2−NHCOO−cyclohexyl)−C6H4−Xn

Het B:
(a) 4-methyl-5-methyl-1,2,3-thiadiazole
(b) 4-methyl-1,2,5-thiadiazole with Me
(c) 4-methyl-1,2,5-oxadiazole with Me

| No | Xn |
| --- | --- |
| 1 | 2-OPh |
| 2 | 3-OPh |
| 3 | 4-OPh |
| 4 | 2-OCF$_2$H |
| 5 | 3-OCF$_2$H |
| 6 | 4-OCF$_2$H |
| 7 | 2-CO$_2$H |
| 8 | 3-CO$_2$H |
| 9 | 4-CO$_2$H |
| 10 | 2-CO$_2$Me |
| 11 | 3-CO$_2$Me |
| 12 | 2-CF$_2$Cl |
| 13 | 3-CF$_2$Cl |
| 14 | 4-CF$_2$Cl |
| 15 | 2-NO$_2$ |
| 16 | 3-NO$_2$ |
| 17 | 4-NO$_2$ |
| 18 | 2-NH$_2$ |
| 19 | 3-NH$_2$ |
| 20 | 4-NH$_2$ |
| 21 | 4-Ph |
| 22 | 2-OCF$_3$ |
| 23 | 3-OCF$_3$ |
| 24 | 4-OCF$_3$ |
| 25 | 2,4-(CF$_3$)$_2$ |
| 26 | 2,5-(CF$_3$)$_2$ |
| 27 | 2,6-(CF$_3$)$_2$ |
| 28 | 3,4-(CF$_3$)$_2$ |
| 29 | 3,5-(CF$_3$)$_2$ |
| 30 | 2-Me, 4-Cl |
| 31 | 2-Me, 3-Cl |
| 32 | 2-Cl, 4-Me |
| 33 | 2-Et, 6-Me |
| 34 | 2-Cl, 5-CF$_3$ |
| 35 | 2-Cl, 6-F |
| 36 | 2,4,6-(Me)$_3$ |

TABLE 59

Structure: Het B−C(=N−O−CH2−[thiazole-4-yl]−2−NHCOOPh)−C6H4−Xn

Het B:
(a) 4-methyl-5-methyl-1,2,3-thiadiazole
(b) 4-methyl-1,2,5-thiadiazole with Me
(c) 4-methyl-1,2,5-oxadiazole with Me

| No | Xn |
| --- | --- |
| 1 | 2-Cl |
| 2 | 3-Cl |
| 3 | 4-Cl |
| 4 | 2,3-(Cl)$_2$ |
| 5 | 2,4-(Cl)$_2$ |
| 6 | 2,5-(Cl)$_2$ |
| 7 | 2,6-(Cl)$_2$ |
| 8 | 3,4-(Cl)$_2$ |
| 9 | 3,5-(Cl)$_2$ |
| 10 | 2,4,6-(Cl)$_3$ |
| 11 | 2-F |
| 12 | 3-F |
| 13 | 4-F |
| 14 | 2,3-(F)$_2$ |
| 15 | 2,4-(F)$_2$ |
| 16 | 2,5-(F)$_2$ |
| 17 | 2,6-(F)$_2$ |
| 18 | 3,4-(F)$_2$ |
| 19 | 3,5-(F)$_2$ |
| 20 | 2,4,6-(F)$_3$ |
| 21 | 2-CH$_3$ |
| 22 | 3-CH$_3$ |
| 23 | 4-CH$_3$ |
| 24 | 2,3-(CH$_3$)$_2$ |
| 25 | 2,4-(CH$_3$)$_2$ |
| 26 | 2,5-(CH$_3$)$_2$ |
| 27 | 2,6-(CH$_3$)$_2$ |
| 28 | 3,5-(CH$_3$)$_2$ |
| 29 | 3-Cl, 5-CH$_3$ |
| 30 | 3-F, 5-CH$_3$ |
| 31 | 3-F, 5-Cl |
| 32 | 2-CF$_3$ |
| 33 | 3-CF$_3$ |
| 34 | 4-CF$_3$ |
| 35 | 2-CN |
| 36 | 3-CN |
| 37 | 4-CN |
| 38 | 2-SMe |
| 39 | 3-SMe |
| 40 | 4-SMe |
| 41 | 2-SO$_2$Me |
| 42 | 3-SO$_2$Me |
| 43 | 4-SO$_2$Me |
| 44 | 2-Br |
| 45 | 3-Br |
| 46 | 4-Br |
| 47 | 2-OH |
| 48 | 3-OH |
| 49 | 4-OH |
| 50 | 2-OMe |
| 51 | 3-OMe |
| 52 | 4-OMe |

TABLE 60

Structure: Het B–C(=N–O–CH₂–[thiazole-2-NHCOOPh])–[phenyl-Xn]

Het B:
(a) 4-methyl-5-methyl-1,2,3-thiadiazole
(b) 4-methyl-3-methyl-1,2,5-thiadiazole
(c) 4-methyl-3-methyl-1,2,5-oxadiazole

| No | Xn |
|---|---|
| 1 | 2-OPh |
| 2 | 3-OPh |
| 3 | 4-OPh |
| 4 | 2-OCF$_2$H |
| 5 | 3-OCF$_2$H |
| 6 | 4-OCF$_2$H |
| 7 | 2-CO$_2$H |
| 8 | 3-CO$_2$H |
| 9 | 4-CO$_2$H |
| 10 | 2-CO$_2$Me |
| 11 | 3-CO$_2$Me |
| 12 | 2-CF$_2$Cl |
| 13 | 3-CF$_2$Cl |
| 14 | 4-CF$_2$Cl |
| 15 | 2-NO$_2$ |
| 16 | 3-NO$_2$ |
| 17 | 4-NO$_2$ |
| 18 | 2-NH$_2$ |
| 19 | 3-NH$_2$ |
| 20 | 4-NH$_2$ |
| 21 | 4-Ph |
| 22 | 2-OCF$_3$ |
| 23 | 3-OCF$_3$ |
| 24 | 4-OCF$_3$ |
| 25 | 2,4-(CF$_3$)$_2$ |
| 26 | 2,5-(CF$_3$)$_2$ |
| 27 | 2,6-(CF$_3$)$_2$ |
| 28 | 3,4-(CF$_3$)$_2$ |
| 29 | 3,5-(CF$_3$)$_2$ |
| 30 | 2-Me, 4-Cl |
| 31 | 2-Me, 3-Cl |
| 32 | 2-Cl, 4-Me |
| 33 | 2-Et, 6-Me |
| 34 | 2-Cl, 5-CF$_3$ |
| 35 | 2-Cl, 6-F |
| 36 | 2,4,6-(Me)$_3$ |

TABLE 61

Structure: Het B–C(=N–O–C(R¹)H–Het C)–[phenyl-Xn]

Het B:
(a) 4-methyl-5-methyl-1,2,3-thiadiazole
(b) 4-methyl-3-methyl-1,2,5-thiadiazole
(c) 4-methyl-3-methyl-1,2,5-oxadiazole

| No | Het C | R¹ | Xn |
|---|---|---|---|
| 1 | 2-phenyl-4-methylthiazole | H | H |
| 2 | 2-(2-chlorophenyl)-4-methylthiazole | H | H |
| 3 | 2-(4-fluorophenyl)-4-methylthiazole | H | H |
| 4 | 2-(2,4-dichlorophenyl)-4-methylthiazole | H | H |
| 5 | 2-(4-phenylphenyl)-4-methylthiazole | H | H |
| 6 | 2-(4-pyridyl)-4-methylthiazole | H | H |
| 7 | 2-(2-pyridyl)-4-methylthiazole | H | H |
| 8 | 2-(pyrimidinyl)-4-methylthiazole | H | H |
| 9 | 2-(2-furyl)-4-methylthiazole | H | H |

TABLE 61-continued

Het B structures (a, b, c): 
- (a) 4-methyl-1,2,3-thiadiazole with Me at 5
- (b) 4-methyl-1,2,5-thiadiazole with Me
- (c) 4-methyl-1,2,5-oxadiazole with Me

| No | Het C | R¹ | Xn |
|---|---|---|---|
| 10 | 2-(thiophen-2-yl)-4-methylthiazole | H | H |
| 11 | 4-(quinolin-4-yl)-2-(4-methylthiazole) | H | H |
| 12 | 2-(1H-indol-3-yl)-4-methylthiazole | H | H |
| 13 | 2-(benzothiophen-2-yl)-4-methylthiazole | H | H |
| 14 | cyclopropyl-CONH-(4-methylthiazol-2-yl) | H | H |
| 15 | cyclobutyl-CONH-(4-methylthiazol-2-yl) | H | H |
| 16 | cyclopentyl-CONH-(4-methylthiazol-2-yl) | H | H |
| 17 | cyclohexyl-CONH-(4-methylthiazol-2-yl) | H | H |
| 18 | cycloheptyl-CONH-(4-methylthiazol-2-yl) | H | H |
| 19 | phenyl-CONH-(4-methylthiazol-2-yl) | H | H |
| 20 | 4-Cl-phenyl-CONH-(4-methylthiazol-2-yl) | H | H |
| 21 | 3-Cl-phenyl-CONH-(4-methylthiazol-2-yl) | H | H |
| 22 | 2-Cl-phenyl-CONH-(4-methylthiazol-2-yl) | H | H |
| 23 | 2,4-diCl-phenyl-CONH-(4-methylthiazol-2-yl) | H | H |
| 24 | 3,4-diCl-phenyl-CONH-(4-methylthiazol-2-yl) | H | H |
| 25 | 3,5-diCl-phenyl-CONH-(4-methylthiazol-2-yl) | H | H |

TABLE 61-continued
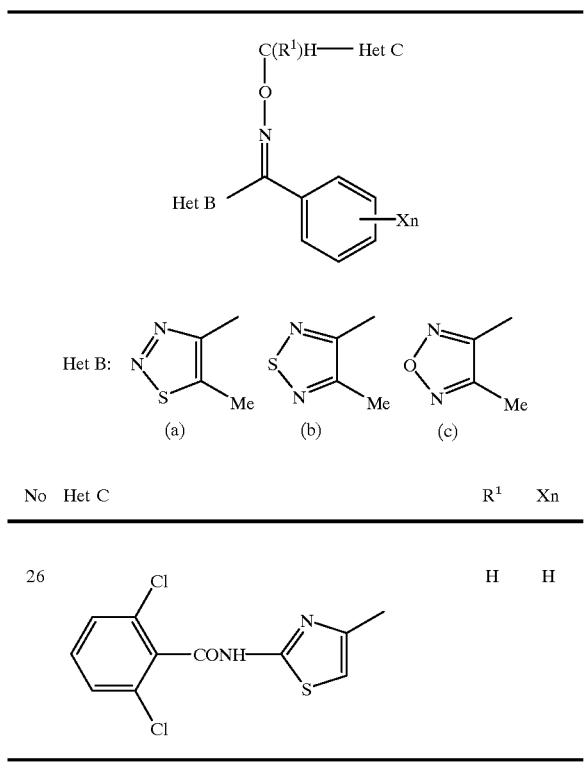
TABLE 62
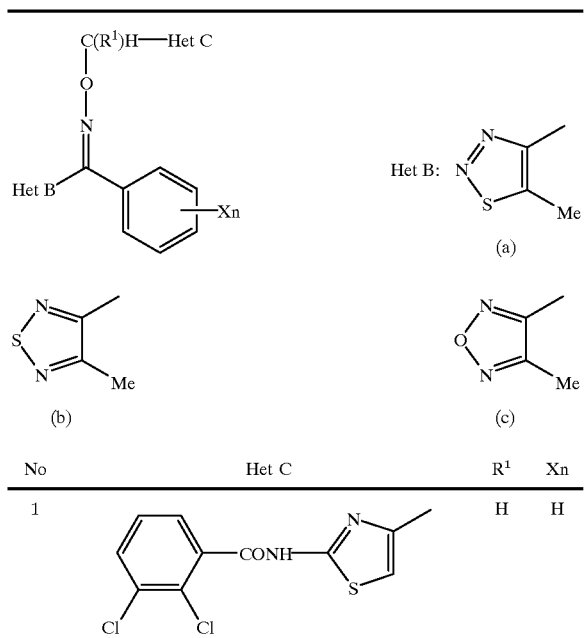
TABLE 62-continued
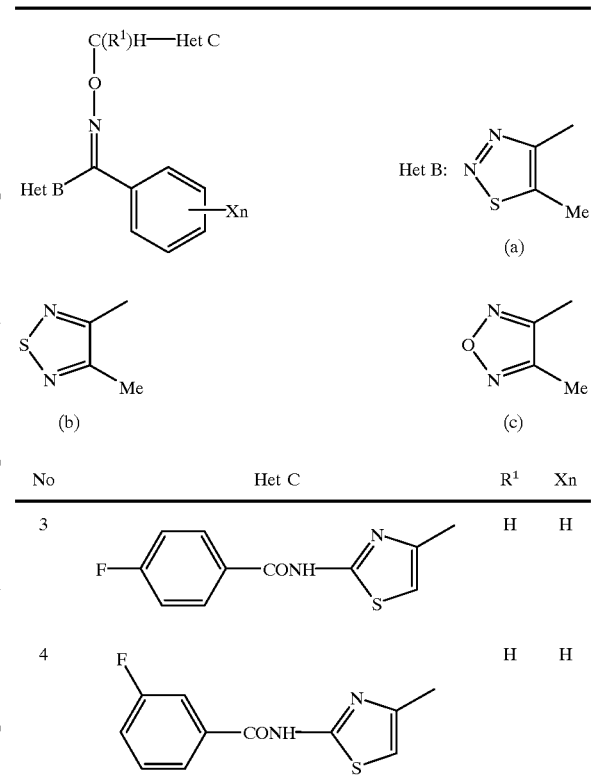
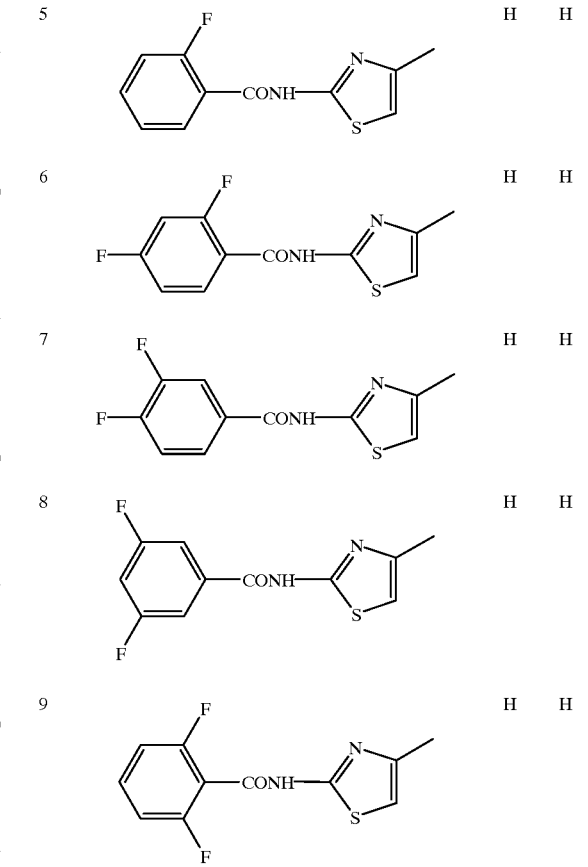

TABLE 62-continued

C(R¹)H—Het C, Het B, with structures (a), (b), (c) as shown.

Het B: (a) 4-methyl-5-methyl-1,2,3-thiadiazole; (b) 3,4-dimethyl-1,2,5-thiadiazole; (c) 3,4-dimethyl-1,2,5-oxadiazole

| No | Het C | R¹ | Xn |
|---|---|---|---|
| 10 | 2,3-difluorophenyl-CONH-(4-methylthiazol-2-yl) | H | H |
| 11 | 4-methylphenyl-CONH-(4-methylthiazol-2-yl) | H | H |
| 12 | 3-methylphenyl-CONH-(4-methylthiazol-2-yl) | H | H |
| 13 | 2-methylphenyl-CONH-(4-methylthiazol-2-yl) | H | H |
| 14 | 2,4-dimethylphenyl-CONH-(4-methylthiazol-2-yl) | H | H |
| 15 | 3,4-dimethylphenyl-CONH-(4-methylthiazol-2-yl) | H | H |
| 16 | 3,5-dimethylphenyl-CONH-(4-methylthiazol-2-yl) | H | H |
| 17 | 2,6-dimethylphenyl-CONH-(4-methylthiazol-2-yl) | H | H |
| 18 | 2,3-dimethylphenyl-CONH-(4-methylthiazol-2-yl) | H | H |
| 19 | 2,4,6-trimethylphenyl-CONH-(4-methylthiazol-2-yl) | H | H |
| 20 | 4-trifluoromethylphenyl-CONH-(4-methylthiazol-2-yl) | H | H |
| 21 | 3-trifluoromethylphenyl-CONH-(4-methylthiazol-2-yl) | H | H |
| 22 | 2-trifluoromethylphenyl-CONH-(4-methylthiazol-2-yl) | H | H |
| 23 | 4-methoxyphenyl-CONH-(4-methylthiazol-2-yl) | H | H |

TABLE 62-continued

Het B: structures (a) 4-methyl-5-methyl-1,2,3-thiadiazole, (b) 4-methyl-1,2,3-thiadiazole, (c) 4-methyl-5-methyl-1,2,5-oxadiazole

| No | Het C | R¹ | Xn |
|----|-------|-----|-----|
| 24 | 2-OCH₃-C₆H₄-CONH-(4-methylthiazol-2-yl) | H | H |
| 25 | 2-SCH₃-C₆H₄-CONH-(4-methylthiazol-2-yl) | H | H |
| 26 | 4-H₂N-C₆H₄-CONH-(4-methylthiazol-2-yl) | H | H |

TABLE 63

Het B: structures (a) 4-methyl-5-methyl-1,2,3-thiadiazole, (b) 4-methyl-1,2,3-thiadiazole, (c) 4-methyl-5-methyl-1,2,5-oxadiazole

| No | Het C | R¹ | Xn |
|----|-------|-----|-----|
| 1 | 4-CH₃CONH-C₆H₄-CONH-(4-methylthiazol-2-yl) | H | H |
| 2 | 4-CF₃O-C₆H₄-CONH-(4-methylthiazol-2-yl) | H | H |
| 3 | 3-CF₃O-C₆H₄-CONH-(4-methylthiazol-2-yl) | H | H |
| 4 | 2-OCF₃-C₆H₄-CONH-(4-methylthiazol-2-yl) | H | H |
| 5 | 4-NC-C₆H₄-CONH-(4-methylthiazol-2-yl) | H | H |
| 6 | 3-NC-C₆H₄-CONH-(4-methylthiazol-2-yl) | H | H |
| 7 | 4-PhO-C₆H₄-CONH-(4-methylthiazol-2-yl) | H | H |
| 8 | 3-PhO-C₆H₄-CONH-(4-methylthiazol-2-yl) | H | H |
| 9 | (naphthalen-1-yl)-CONH-(4-methylthiazol-2-yl) | H | H |

TABLE 63-continued

Het B: (a) 4-methyl-5-methyl-1,2,3-thiadiazole; (b) 3,4-dimethyl-1,2,5-thiadiazole; (c) 3,4-dimethyl-1,2,5-oxadiazole

| No | Het C | R¹ | Xn |
|---|---|---|---|
| 10 | quinoline-8-C(O)NH-(4-methylthiazol-2-yl) | H | H |
| 11 | isoquinoline-1-C(O)NH-(4-methylthiazol-2-yl) | H | H |
| 12 | quinoxaline-2-C(O)NH-(4-methylthiazol-2-yl) | H | H |
| 13 | cinnoline-3-C(O)NH-(4-methylthiazol-2-yl) | H | H |
| 14 | pyridine-4-C(O)NH-(4-methylthiazol-2-yl) | H | H |
| 15 | pyridine-2-C(O)NH-(4-methylthiazol-2-yl) | H | H |
| 16 | pyridazine-3-C(O)NH-(4-methylthiazol-2-yl) | H | H |
| 17 | pyrazine-2-C(O)NH-(4-methylthiazol-2-yl) | H | H |
| 18 | pyrimidine-2-C(O)NH-(4-methylthiazol-2-yl) | H | H |
| 19 | furan-2-C(O)NH-(4-methylthiazol-2-yl) | H | H |
| 20 | thiophene-2-C(O)NH-(4-methylthiazol-2-yl) | H | H |
| 21 | imidazole-4-C(O)NH-(4-methylthiazol-2-yl) | H | H |
| 22 | 1-methylpyrazole-5-C(O)NH-(4-methylthiazol-2-yl) | H | H |
| 23 | oxazole-4-C(O)NH-(4-methylthiazol-2-yl) | H | H |
| 24 | thiazole-4-C(O)NH-(4-methylthiazol-2-yl) | H | H |
| 25 | isoxazole-5-C(O)NH-(4-methylthiazol-2-yl) | H | H |

TABLE 63-continued
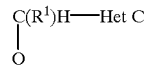
| No | Het C | R¹ | Xn |
|----|-------|----|----|
| 26 |  | H | H |
TABLE 64
| No | Het C | R¹ | Xn |
|----|-------|----|----|
| 1 | 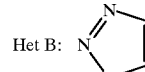 | H | H |
| 2 | 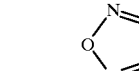 | H | H |
| 3 | 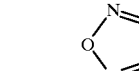 | H | H |
| 4 |  | H | H |
TABLE 64-continued
| No | Het C | R¹ | Xn |
|----|-------|----|----|
| 5 | 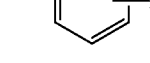 | H | H |
| 6 |  | H | H |
| 7 | 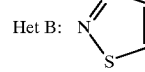 | H | H |
| 8 | 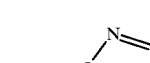 | H | H |
| 9 |  | H | H |
| 10 |  | H | H |
| 11 |  | H | H |
| 12 | 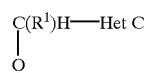 | H | H |

TABLE 64-continued $$\text{Het B}-\underset{\underset{O}{\overset{\parallel}{N}}}{\overset{C(R^1)H-Het\ C}{\phantom{C}}}-\text{Ph}-Xn$$

Het B:

(a) 4-methyl-5-methyl-1,2,3-thiadiazole (b) 3-methyl-4-methyl-1,2,5-thiadiazole (c) 3-methyl-4-methyl-1,2,5-oxadiazole (furazan)

| No | Het C | R¹ | Xn |
|----|-------|-----|-----|
| 13 | benzothiazole-2-CONH—(4-methylthiazol-2-yl) | H | H |
| 14 | PhCH₂CONH—(4-methylthiazol-2-yl) | H | H |
| 15 | PhCH₂CH₂CONH—(4-methylthiazol-2-yl) | H | H |
| 16 | H₂NCH₂CONH—(4-methylthiazol-2-yl) | H | H |
| 17 | H₂NCH(Me)CONH—(4-methylthiazol-2-yl) | H | H |
| 18 | H₂NCH(CH(Me)₂)CONH—(4-methylthiazol-2-yl) | H | H |
| 19 | H₂NCH(CH₂Ph)CONH—(4-methylthiazol-2-yl) | H | H |
| 20 | MeCONHCH₂CONH—(4-methylthiazol-2-yl) | H | H |
| 21 | (Me)₃COCONHCH(Me)CONH—(4-methylthiazol-2-yl) | H | H |
| 22 | (Me)₃COCONHCH(CH(Me)₂)CONH—(4-methylthiazol-2-yl) | H | H |
| 23 | EtC(O)NHCH₂CONH—(4-methylthiazol-2-yl) | H | H |
| 24 | (Me)₂CHC(O)NHCH₂CONH—(4-methylthiazol-2-yl) | H | H |
| 25 | EtC(O)NHCH(Me)CONH—(4-methylthiazol-2-yl) | H | H |
| 26 | (Me)₂CHC(O)NHCH(Me)CONH—(4-methylthiazol-2-yl) | H | H |

TABLE 65
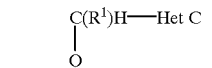
| No | Het C | R¹ | Xn |
|---|---|---|---|
| 1 | 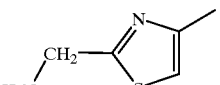 | H | H |
| 2 | 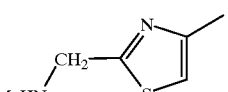 | H | H |
| 3 | 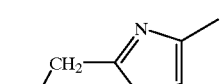 | H | H |
| 4 | 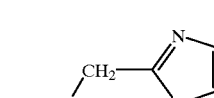 | H | H |
| 5 | 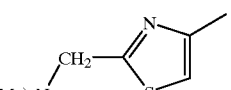 | H | H |
| 6 | 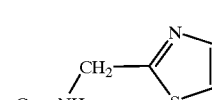 | H | H |
| 7 |  | H | H |
| 8 | 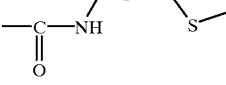 | H | H |
TABLE 65-continued
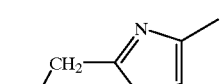
| No | Het C | R¹ | Xn |
|---|---|---|---|
| 9 | 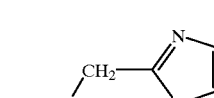 | H | H |
| 10 | 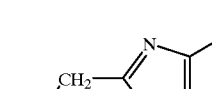 | H | H |
| 11 |  | H | H |
| 12 | 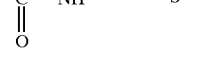 | H | H |
| 13 | 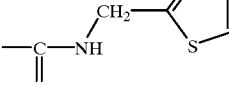 | H | H |
| 14 | 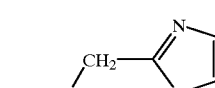 | H | H |
| 15 | 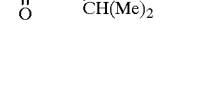 | H | H |

TABLE 66

Het B—C(=N—O—CH₂—Het C)—C₆H₄(Xn)

Het B:

(a) 1,2,3-thiadiazole with Y substituent
(b) 1,2,3-thiadiazole isomer with Y substituent

| No | Het C | Xn | Y |
|---|---|---|---|
| 1 | (CH₃)₂CHCONH-thiazole | H | CF₃ |
| 2 | (CH₃)₂CHCONH-thiazole | 4-Cl | CF₃ |
| 3 | (CH₃)₂CHCONH-thiazole | 3-Cl | CF₃ |
| 4 | (CH₃)₂CHCONH-thiazole | 4-F | CF₃ |
| 5 | (CH₃)₂CHCONH-thiazole | 3-F | CF₃ |
| 6 | (CH₃)₂CHCONH-thiazole | H | Cl |
| 7 | (CH₃)₂CHCONH-thiazole | 4-Cl | Cl |
| 8 | (CH₃)₂CHCONH-thiazole | 3-Cl | Cl |
| 9 | (CH₃)₂CHCONH-thiazole | 4-F | Cl |
| 10 | (CH₃)₂CHCONH-thiazole | 3-F | Cl | wherein, Het A, Het B, Het C, X, Y, n, and R¹ correspond to those defined in the general formulas (1) and (2), and Me represents a methyl group, Et represents an ethyl group, Pr represents a propyl group, Bu represents a butyl group, and Ph represents a phenyl group.

Agricultural chemicals, particularly plant disease control chemicals, which contain the oxime derivatives according to the present invention as active ingredients, are effective for various plant diseases involving bacteria and mold fungi, and are particularly effective for plant diseases caused by mold fungi. The plant diseases caused by mold fungi include a wide range of types of plant diseases caused by Oomycetes and plant diseases caused by *Pyricularia oryzae*.

The agricultural chemicals of the present invention are particularly effective for plant diseases such as downymildew and late-blight or Phytophthora rot of various plants, which include a wide variety of plant diseases caused by Oomycetes such as *Plasmopara viticola, Pseudoperonospora cubensis, Phytophthora melonis, Phytophthora capsici, Phythophthora infestans, Peronospora brassicae, Peronospora destructor, Peronospora spinaciae*, and *Peronospora manshurica*;

and, *Peronospora viciae, Phytophthora nicotianae* var. *nicotianae, Phytophtora infestans, Pseudoperonospora humuli, Phytophthora cinnamomi, Phytophthora capsici, Phytophthora fragariae*, diseases for various farm products by Pythium bacteria, *Pythium aphanidermatum*, and *Pyricularia oryzae*.

The agricultural chemicals of the present invention may be used alone, or, in general, may be used in combinations with known auxiliary substances such as solid and liquid carriers, dispersing agents, diluents, emulsifiers, spreaders, thickners. The agricultural chemicals of the present invention may be used in the forms of wettable powder, solutions, oil solutions, powder, granules, and sol-type forms by formulation.

Examples of the solid and liquid carriers include, for example, talc, clay, bentonite, kaolin, diatomite, montmorillonite, micas, vermiculite, gypsum, calcium carbonate, white carbon, wood powder, starch, alumina, silicate salt, glycol polymer, waxes, water, alcohols (such as methyl alcohol, ethyl alcohol, n-propyl alcohol, isopropyl alcohol, n-butyl alcohol, ethylene glycol, benzyl alcohol), petroleum fractions (such as petroleum ether, kerosene, solvent naphtha), aliphatic and alicyclic hydrocarbons (such as n-hexane, cyclohexane); and aromatic hydrocarbons (such as benzene, toluene, xylene, ethylbenze, chlorobenzene, cumene, and methylnaphthalene), halogenized hydrocarbons (such as chloroform, dichloromethane), ethers (such as isopropyl ether, ethylene oxide, and tetrahydrofuran), ketones (such as acetone, methylethyl ketone, cyclohexane, and mthylisobutyl ketone), esters (such as ethyl acetate, butyl acetate, ethyleneglycol acetate, and amyl acetate), acid amides (such as dimethylforamide, and dimethylacetoanilide), nitriles (such as acetonitrile, prop ionitrile, acrylonitrile), sulfoxides (such as dimethylsulfoxide), alcohol ethers (such as ethyleneglycol monomethylether, and ethyleneglycol monoethylether).

Examples of the auxiliary substances include, for example, non-ionic-type surface active agents (such as polyoxyethylene alkylether, polyoxyethylene alkylester, polyoxyethylene alkylphenylether, polyoxyethylene sorbitanalkylester, and solbitanalkylester), anionic-type surface active agents (such as alkylbenzenesulfonate, alkylsulfosuccinate, polyoxyethylene alkylsulfate, and arylsulfonate), cationic-type surface active agents such as (alkylamines, polyoxyethylene alkylamines, and quarternary ammonium salts), amphoteric surfactants (such as alkylaminoethylglycine and alkyldimethylbetaine), polyvinyl alcohol, hydroxypropyl cellulose, carboxymethyl cellulose, gum arabic, tragacanth gum, xanthan gum, polyvinyl acetate, gelatin, casein, and sodium alginate.

Furthermore, the present agents may be used in combinations with known agricultural chemicals such as agricultural and horticultural fungicide, herbicides, growth regulators of plants, insecticides, acaricides, and with fertilizers. Although the contents of the present chemicals vary depending upon the forms of the chemicals, application methods, and other conditions, the effective content ranges from 0.5 to 95% by weight, and preferably, from 2 to 70% by weight.

Various methods may be applied, including application to foliage (foliage spraying), application to planting soil (soil treatment), application to the water surface of a field (water surface treatment), and application to seeds (seed treatment).

The amount of the present agricultural chemicals varies with the type of plants to which it is applied and the disease in question. When the chemicals are applied to foliage, it is preferable to apply then using a liquid solution at a rate of 50 to 300 liters per 10 are at a concentration of 1 to 10,000 ppm, preferably, 10 to 1,000 ppm as an effective chemical concentration. For application to a water surface or soil, it is preferable to apply 0.1 to 100 g per 10 are. When treating seeds, it is preferable to apply 0.001 to 50 g of the present agricultural chemicals per 1 kg of seed.

Hereinafter, the present invention will be described in more detail referring to following examples in terms of manufacturing methods, formulation examples and test examples. It is to be understood that the present invention is not limited to the following examples.

MANUFACTURING EXAMPLE 1

Hydroxylamine hydrochloride (0.20 g, 2.82 mmol) and triethylamine (0.4 ml, 2.8 mmol) were added to an ethanol solution (20 ml) of (5-methyl-1, 2, 3-thiaziasol-4-yl) phenylmethanone (0.29g, 1.41 mmol) and heated for 48 hours with refluxing. After concentrating the thus reacted solution, ethyl acetate was added to the residue, washed with water, and the residue was dried with magnesium sulfate. The solvent was removed by distillation and the residue was purified by column chromatography and yielded (Z)-(5-methyl-1, 2, 3-thiadiazol-4-yl)phenylmethanone oxime (0.16 g) and (E)-(5-methyl-1, 2, 3-thiadiazol-4-yl) phenyl methanone oxime (0.04 g).

(Z)-(5-methyl-1, 2, 3-thiadiazol-4-yl)phenylmethanone oxime: $^1$H-NMR (CDCl$_3$): δ 2.54 (s. 3H), 7.30~7.50 (m. 5H), 8.30~8.45 (brd. 1H). MS (m/e): 219 (M$^+$);

(E)-(5-mthyl-1, 2, 3-thiadiazol-4-yl)phenylmethanone oxime: $^1$H-NMR (CDCl$_3$): δ 2.54 (s. 3H), 7.35~7.60 (m. 5H), 8.00~8.20 (brd. 1H). MS (m/e): 219 (M$^+$).

MANUFACTURING EXAMPLE 2

(Z)-(5-methyl-1, 2, 3-thiadiazol-4-yl)phenylmethanone oxime (9.31 g, 0.04 mol) was dissolved in acetonitrile (677 ml), hydrochloride of 2-picolylchloride (10.40 g, 0.07 mol) was added and heated for 5 hours with refluxing. After concentrating the thus reacted solution, the residue was extracted by ethyl acetate, and the extracted substance was dried after washing by water. The solvent was removed by distillation, the residue was purified by column chromatography, and yielded (Z)-(5-methyl-1, 2, 3-thiadiazol-4-yl) phenylmethanone O-(2-pyrydyl)-methyl oxime (9.67 g) (Compound No. 1-(a)-1(Z)).

$^1$H-NMR (CDCl$_3$): δ 2.53 (s. 3H), 5.40 (s. 2H), 7.19 (dd., J=4.9 Hz, J=7.6 Hz, 1H), 7.30~7.42 (m. 3H), 7.35 (d. J=7.8 Hz, 1H), 7.44~7.50 (m. 2H), 7.67 (J=7.8 Hz, J=7.6 Hz, 1H), 8.56 (d. J=4.9 Hz, 1H). MS (m/e): 310 (M$^+$).

MANUFACTURING EXAMPLE 3

(E)-(5-mthyl-1, 2, 3-thiadiazol-4-yl) phenylmethanone oxime (0.30 g, 1.4 mmol) was dissolved in acetone (20 ml), potassium carbonate (0.32 g, 2.0 mmol) and hydrochloride of 2-picolylchloride (0.34 g, 2.0 mmol) were added and heated for 3 days with refluxing. After concentrating the thus reacted solution, the residue was extracted with ethylacetate, and after washing with water, the residue was dried with magnesium sulfate. The solvent was removed by distillation, the residue was refined in a column chromatography, and yielded (E)-(5-mthyl-1, 2, 3-thiadiazol-4-yl)phenylmethanone O-(2-pyridyl) methyloxime.

$^1$H-NMR (CDCl$_3$): δ 2.59 (s. 3H), 5.40 (s. 2H), 7.21 (dd., J=4.83 Hz, J=8.70 Hz, 1H), 7.31~7.72 (m. 7H), 8.58 (J=4.88 Hz, 1H). MS (m/e): 310 (M$^+$).

MANUFACTURING EXAMPLE 4

Hydroxylamine hydrochloride (4.48 g, 63.1 mmol) and triethylamine (8.8 ml, 63.1 mmol) were added to an ethanol solution (85 ml) of (3-methyl-1, 2, 5-thiadiazol-4-yl) phenylmethane (3.22 g, 15.7 mmol) and heated for 8 hours with refluxing. After the reacted solution was concentrated, ethyl acetate/water was added to the residue for extraction. The residue was dried with magnesiun sulfate, after the solvent was removed by distillation. The residue was refined by column chromatography and yielded (Z)-(3-methyl-1, 2, 5-y thiadiazol-4-yl) phenylmethanone oxime (2.18 g).

$^1$H-NMR (CDCl$_3$): δ 2.53 (s. 3H), 7.27~7.56 (m. 5H), 8.52~8.78 (brd. 1H). MS (m/e): 219 (M$^+$).

MANUFACTURING EXAMPLE 5

60% sodium hydride (2.41 g, 60.0 mmol) was added to DMF (150 ml) (N,N-Dimethyl-foramide) and cooled by ice, and (Z)-(3-methyl-1, 2, 5-thiadiazol-4-yl) pheylmethaneoxime was then added and stirred for 40 minutes. A DMF (110 ml) solution of 4-chloromethyl-2-iso-propionylaminothiazole (7.76 g, 35.6 mmol) was added dropwise to the thus reacted solution. After the reacted solution was gradually restored to the room temperature, it was stirred for 20 hours. The solvent in the reacted solution was removed under a reduced pressure and ethyl-acetate/water was added to the residue for extraction. The extracted solution was dried with magnesium sulfate after washing by water. The solvent was removed by distillation, and the residue was refined by column chromatography, and yielded (Z)-(3-methyl-1, 2, 5-thiadiazol-4-yl) pheylmethane O-(2-iso-propionylaminothiazol-4-yl) methyloxime.

$^1$H-NMR (CDCl$_3$): δ 1.22 (d. J=6.91 Hz, 6H), 2.41 (s. 3H), 2.47~2.76 (m. 1H), 5.21 (s. 2H), 6.89 (s. 1H) 7.28~7.60 (m. 5H), 9.50~9.90 (brd. 1H). MS (m/e): 401 (M$^+$).

MANUFACTURING EXAMPLE 6

A pyridine (55 ml) solution of hydroxylamine hydrochloride (5.19 g, 73.0 mmol) was added to (3-methyl-1, 2, 5-oxadiazol-4-yl) phenylmethanone (3.43 g, 18.0 mmol) and heated to 70° C. for 21 hours with stirring. After the reacted solution was condensed, the residue was dissolved in ethyl acetate. After washing with diluted hydrochloride and subsequent washing with water, the residue was dried with magnesium carbonate. After removing the solvent and purifying the residue by column chromatography, (Z)-(3-methyl-1, 2, 5-oxadiazol-4-yl) phenylmethanone oxime (2.13 g) and (E)-(3-methyl-1, 2, 5-oxadiazol-4-yl) phenylmethanone oxime (0.79 g) were obtained.

(Z)-(3-methyl-1, 2, 5-oxadiazol-4-yl) phenylmethanone oxime: $^1$H-NMR (CDCl$_3$): δ 2.38 (s. 3H), 7.30~7.62 (m. 2H), 7.89~8.00 (brd. 1H). MS (m/e): 219 (M$^+$). (E)-(3-methyl-1, 2, 5-oxadiazol-4-yl)phenylmethanone oxime:

¹H-NMR (CDCl₃): δ 2.55 (s. 3H), 7.48~7.62 (m. 2H), 7.89~8.00 (brd. 1H). MS (m/e): 219 (M⁺).

MANUFACTURING EXAMPLE 7

60% sodium hydride (0.43 g, 10.6 mmol) was added to DMF (16 ml) and cooled by ice, and a DMF (20ml) solution of (Z)-(3-methyl-1, 2, 5-oxadiazol-4-yl) phenylmethanone oxime (0.94 g, 4.36 mmol) was added to that solution with stirring. A DMF (15 ml) solution of 4-chloromethyl-2-triphenylmethylaminothiazole (2.71 g, 6.94 mmol) was added to the above reacted solution. After the reacted solution was restored to the room temperature, the reacted solution was stirred for four days. The solvent of the solution was then removed under reduced pressure and added to ethyl acetate/water to the residue for extraction. The solvent was removed by distillation, the residue was refined by column chromatography, and yielded (Z)-(3-methyl-1, 2, 5-oxadiazol-4-yl) phenylmethanone O-(2-triphenylmethylaminethiazol-4-yl) methyloxime (0.59 g) (Compound No. 9-(c)-6 (Z)).

¹H-NMR (CDCl₃): δ 2.23 (s. 3H), 5.11 (s. 2H), 6.27 (s. 1H), 6.80~6.97 (brd. 1H), 7.13~7.60 (m. 20H). MS (m/e): 557 (M⁺).

MANUFACTURING EXAMPLE 8

1M hydrochloride (0.6 ml) was added to an acetone (15 ml) solution of (Z)-(3-methyl-1, 2, 5-oxadiazol-4-yl) phenylmethanone O-(2-triphenylmethylaminethiazol-4-yl) methyloxime, and heated for 8 hours with refluxing. The solvent of the reacted solution was removed under reduced pressure, and a solution of ethyl acetate/saturated solution of sodium hydrogencarbonate was added and extracted after the solution was adjusted to pH=7. The extracted solution was washed with water and the residue was dried with magnesium sulfate. The solvent was removed by distillation and the residue was refined by column chromatography and yielded (Z)-(3-methyl-1, 2, 5-oxadiazol-4-yl) phenylmethanone O-(2-aminethiazol-4-yl) methyloxime (0.05 g) (Compound No. 8-(c)-1 (Z)).

¹H-NMR (CDCl₃): δ 2.31 (s. 3H), 4.85~5.10 (brd. 1H), 5.14 (s. 2H), 6.46 (s. 1H), 7.32~7.66 (m. 5H). MS (m/e): 315 (M⁺).

MANUFACTURING EXAMPLE 9

Trifluoroacetic acid anhydride (7 ml) was added to (Z)-(3-methyl-1, 2, 5-oxadiazol-4-yl) phenylmethanone O-(2-aminethiazol-4-yl) methyloxime (0.053 g, 0.168 mmol) and heated for 2 hours with stirring. The reacted solution was concentrated, the residue was refined by column chromatography and yielded (Z)-(3-methyl-1, 2, 5-oxadiazol-4-yl) phenylmethanone O-(2-trifluoroacetylaminethiazol-4-yl) methyloxime (0.063 g) (Compound No. 8-(c)-14 (Z)).

¹H-NMR (CDCl₃): δ 2.26 (s. 3H), 5.26 (s. 2H), 7.07 (s. 1H), 7.28~7.56 (m. 5H), 768~8.10 (brd. 1H). MS (m/e): 411 (M⁺).

Physical and chemical data such as ¹H-NMR spectra and mass spectra of oxime derivatives obtained by the same manufacturing methods as those shown in the above manufacturing examples are summarized in Tables 67 to 81.

TABLE 67

| Compound Table-(a), (b), (c)-No. | E/Z | ¹H-NMR (CDCl₃) δ | MS (m/e, M⁺) |
|---|---|---|---|
| 1-(a)-1 | Z | 2.53 (s, 3H), 5.40 (s, 2H), 7.19 (dd, J = 4.9Hz, J = 7.6Hz, 1H), 7.30–7.42 (m, 3H), 7.35 (d, J = 7.8Hz, 1H) 7.44–7.50 (m, 2H), 7.67 (dd, J = 7.8, 7.6Hz, 1H), 8.56 (d, J = 4.9Hz, 1 H). | 310 |
| 1-(a)-1 | E | 2.59 (s, 3H), 5.40 (s, 2H), 7.21 (dd, J = 4.83, 8.70Hz, 1H), 7.31–7.72 (m, 7H), 8.58 (d, J = 4.88Hz, 1H). | 310 |
| 1-(b)-1 | Z | 2.47 (s, 3H), 5.36 (s, 2H), 7.19 (dd, J = 4.85Hz, J = 7.40Hz, 1H), 7.30–7.50 (m, 6H), 7.67 (t, J = 7.64Hz, 1H), 8.56 (d, J = 4.80Hz, 1H). | 311 (M⁺ + 1) |
| 1-(b)-1 | E | 2.60 (s, 3H), 5.40 (s, 2H), 7.15–7.55 (m, 7H), 7.70 (t, J = 7.60Hz, 1H), 8.59 (d, J = 4.80Hz, 1H). | 311 (M⁺ + 1) |
| 1-(c)-1 | Z | 2.32 (s, 3H), 5.41 (s, 2H), 7.15–7.60 (m, 7H), 7.69 (t, J = 774Hz, 1H), 8.56 (d, J = = 4.81Hz, 1H). | 294 |
| 1-(a)-2 | Z | 2.42 (s, 3H), 5.26 (s, 2H), 7.25–7.50 (m, 6H), 7.70 (d, J = 10.2Hz, 1H), 8.56 (d, J = 4.84Hz, 1H), 8.62 (s, 1H). | 310 |
| 1-(a)-2 | E | 2.56 (s, 3H), 5.27 (s, 2H), 7.28–7.52 (m, 6H), 7.70–7.78 (m, 1H), 8.57 (d, J = 4.82Hz, 1H), 8.65(s, 1H). | 310 |
| 1-(a)-3 | Z | 2.48 (s, 3H), 5.26 (s, 2H), 7.22 (d, J = 5.91Hz, 2H), 7.29–7.50 (m, 5H), 8.58 (d, J = 6.03Hz, 2H). | 310 |
| 1-(a)-3 | E | 2.55 (s, 3H), 5.27 (s, 2H), 7.25 (d, J = 8.00Hz, 2H) 7.30–7.60 (m, 5H), 8.59 (d, J = 8.00Hz, 2H). | 310 |
| 1-(a)-4 | Z | 2.55 (s, 3H)1 5.36 (s, 2H), 7.30–7.54 (m, 6H), 8.71 (d, J = 5.00Hz, 1H), 9.16 (s, 1H). | 311 |
| 1-(a)-5 | Z | 2.52 (s, 3H), 5.41 (s, 2H), 7.30–7.55 (m, 5H), 8.49–8.60 (m, 2H), 8.67 (s, 1H). | 312 (M⁺ + 1) |
| 1-(a)-8 | Z | 2.54 (s, 6H), 5.36 (s, 2H), 7.05 (d, J = 7.56Hz, 1H), 7.12 (d, J = 7.58Hz, 1H), 7.30–7.62 (m, 6H). | 324 |
| 1-(a)-9 | Z | 2.32 (s, 3H), 2.51 (s, 3H), 5.35 (s, 2H), 7.14–7.55 (m, 7H), 8.39 (s, 1H). | 324 |

TABLE 68

| Compound Table-(a), (b), (c)-No. | E/Z | ¹H-NMR (CDCl₃) δ | MS (m/e, M⁺) |
|---|---|---|---|
| 1-(b)-9 | Z | 2.32 (s, 3H), 2.47 (s, 3H), 5.33 (s, 2H) 7.18 (d, J = 7.94Hz1 1H), 7.27–7.56 (m, 6H), 8.39 (s, 1H). | 324 |
| 1-(b)-9 | E | 2.34 (s, 3H), 2.62 (s, 3H), 5.36 (s, 2H), 7.12–7.63 (m, 7H), 8.32–8.49 (m, 1H). | 324 |
| 1-(c)-9 | Z | 2.31 (s, 3H), 2.33 (s, 3H), 5.36 (s, 2H), 7.19 (d, J = 7.90Hz, 1H), 7.30–7.60 (m, 6H), 8.41 (s, 1H). | 308 |
| 1-(c)-9 | E | 2.34 (s, 3H), 2.43 (s, 3H), 5.36 (s, 2H), 7.20 (d, J = 7.90Hz, 1H), 7.39–7.69 (m, 6H), 8.42 (s, 1H). | 308 |
| 1-(a)-10 | Z | 2.49 (s, 3H), 2.54 (s, 3H), 5.23 (s, 2H), 7.03 (d, J = 5.33Hz, 1H), 7.07 (s, 1H), 7.26–7.54 (m, 5H), 8.45 (d, J = 4.79 Hz, 1H). | 324 |
| 1-(a)-12 | Z | 2.54 (s, 3H), 5.35 (s, 2H), 7.18–7.52 (m, 7H), 7.64(t, J = 7.80Hz, 1H). | 344 |
| 1-(a)-16 | Z | 2.55 (s, 3H), 5.31 (s, 2H), 6.83 (dd, J = 2.48Hz, J = 7.81Hz, 1H), 7.22 (dd, J = 1.92Hz, J = 7.46Hz, 1H), 7.30–7.56 (m, 5H), 7.77 (dd, J = 7.62Hz, 7.95Hz, 1H). | 329 (M⁺ + 1) |
| 2-(a)-1 | Z | 2.53 (s, 3H), 5.57 (s, 2H), 7.25–7.40 (m, 3H), 7.41–7.60 (m, 4H), 7.64–7.77 (m, 1H), 7.80 (d, J = 8.30Hz, 1H), 8.07 (d, J = 8.26Hz, 1H), 8.16 (d, J = 8.50Hz, 1H). | 360 |
| 2-(8)-3 | Z | 2.54 (s, 3H), 5.59 (s, 2H), 7.30–7.60 (m, 5H), 7.65–7.92 (m, 2H), 7.98–8.37 (m, 2H), 8.97 (s, 1H). | 361 |
| 2-(a)-4 | Z | 1.59 (d, J = 6.76Hz, 3H), 2.55 (s, 3H), 5.55 (q, J = 6.73Hz, 1H), 7.10–7.50 (m, 7H), 7.65 (t, J = 7.75Hz, 1H), 8.55 (d, J = 4.81Hz, 1H). | 325 (M⁺ + 1) |

TABLE 68-continued

| Compound Table-(a), (b), (c)- No. | E/Z | ¹H-NMR (CDCl₃) δ | MS (m/e, M⁺) |
|---|---|---|---|
| 2-(b)-4 | Z | 1.58 (d, J = 6.78Hz, 3H), 2.51 (s, 3H), 5.52 (q, J = 6.72, 1H), 7.10–7.50 (m, 7H), 7.64 (t, J = 7.71Hz, 1H), 8.50–8.63 (m, 1H). | 324 |

TABLE 69

| Compound Table-(a), (b), (c)- No. | E/Z | ¹H-NMR (CDCl₃) δ | MS (m/e, M⁺) |
|---|---|---|---|
| 2-(a)-7 | Z | 1.29 (t, J = 7.60Hz, 3H), 2.90 (q J = 7.60Hz, 2H), 5.39 (s, 2H), 7.13–7.27 (m, 1H), 7.30–7.54 (m, 6H), 7.67 (t, J = 7.64Hz, 1H), 8.57 (d, J = 4.84Hz, 1H). | 324 |
| 2-(b)-7 | Z | 1.26 (t, J = 7.49Hz, 3H), 2.80 (q, J = 7.49Hz, 2H), 5.36 (s, 2H), 7.10–7.80 (m, 8H), 8.50–8.63 (m, 1H). | 324 |
| 2-(b)-7 | E | 1.27 (t, J = 7.50Hz, 3H), 2.96 (q, J = 7.50Hz, 2H), 5.41 (s, 2H), 7.10–7.80 (m, 8H), 8.50–8.63 (m, 1H). | 324 |
| 2-(c)-7 | Z | 1.22(t, J = 7.55Hz, 3H), 2.70 (, J = 7.55Hz, 2H), 5.40 (s, 2H), 7.13–7.81 (m, 8H), 8.50–8.70 (m, 1H). | 309 (M⁺ + 1) |
| 2-(a)-10 | 1) | 4.14 (s, 2H), 6.45 (s, 1H), 6.65 (t, J = 7.72Hz, 1H), 7.12–7.25 (m, 1H), 7.34 (d, J = 7.85Hz, 1H), 7.45–7.50 (m, 3H), 7.70–7.80 (m, 2H), 8.57 (d, J = 5.16 Hz, 1H). | 296 |
| 3-(b)-1 | 1) | 5.34 (s, 2H), 7.10–7.60 (m, 7H), 7.67 (m, 1H), 8.55 (d, J = 5.41Hz, 1H). | 364 |
| 3-(b)-6 | Z | 5.45 (s, 2H), 7.10–7.25 (m, 1H), 7.31–7.61 (m, 6H), 7.69 (t, J = 7.74Hz, 1H), 8.58 (d, J = 3.98Hz, 1H). | 331 |
| 3-(b)-6 | E | 5.39 (s, 2H), 7.12–7.28 (m, 1H), 7.30–7.60 (m, 6H), 7.62–7.76 (m, 1H). | 331 |
| 3-(a)-7 | 2) | 5.55 (s, 2H), 7.20–7.40 (m, 1H), 7.41 (d, J = 8.70Hz, 2H), 7.40–7.60 (m, 1H), 7.73 (d, J = 8.70Hz, 2H), 7.64–7.82 (m, 1H), 8.61 (d, J = 4.61Hz, 1H). | 352 |
| 4-(a)-1 | E | 2.67 (s, 3H), 5.38 (s, 2H), 7.15–7.3 (m, 1H), 7.3–7.55 (m, 5H), 7.6–7.8 (m, 1H), 8.5–8.65 (m, 1H). | 344 |
| 4-(a)-2 | Z | 2.53 (s, 3H), 5.40 (s, 2H), 7.20 (m, 1H), 7.25–7.45 (m, 4H), 7.51 (m, 1H), 7.69 (ddd, J = 1.8, 1.8, 7.7 Hz, 1H), 8.56 (m, 1H). | 344 |

¹Stereochemistry is unidentified.

TABLE 70

| Compound Table-(a), (b), (c)- No. | E/Z | ¹H-NMR (CDCl₃) δ | MS (m/e, M⁺) |
|---|---|---|---|
| 4-(a)-2 | E | 2.61 (s, 3H), 5.40 (s, 2H), 7.22 (m, 1H), 7.34 (d, J = 7.7 Hz, 1H), 7.4 (m, 3H), 7.55 (m, 1H), 7.71 (ddd, J = 1.8, 1.8, 7.7 Hz, 1H), 8.59 (m, 1H). | 344 |
| 4-(a)-3 | Z | 2.52 (s, 3H), 5.39 (s, 2H), 7.21 (dd, J = 4.7, 7.7 Hz, 1H), 7.26–7.36 (m, 3H), 7.42 (ddd, J = 2.2, 2.2, 8.7 Hz, 2H), 7.67 (ddd, J = 1.8, 7.7, 7.7 Hz, 1H), 8.56 (d, J = 4.7 Hz, 1H). | 344 |
| 4-(a)-3 | E | 2.61 (s, 3H), 5.40 (s, 2H), 7.22 (dd, J = 4.8, 7.7 Hz, 1H), 7.33 (d, J = 7.7 Hz, 1H), 7.43 (ddd, J = 2.0, 2.0, 8.8 Hz, 2H), 7.52 (ddd, J = 2.0, 2.0, 8.8 Hz, 2H), 7.70 (ddd, J = 1.8, 7.7, 7.7 Hz, 1H), 8.59 (m, 1H). | 344 |
| 4-(b)-3 | Z | 2.47 (s, 3H), 5.36 (s, 2H), 7.15–7.5 (m, 6H), 7.67 (m, 1H), 8.58 (m, 1H). | 343 (M⁺ − 1) |
| 4-(a)-12 | Z | 2.53 (s, 3H), 5.40 (s, 2H), 7.01–7.40 (m, 6H), 7.62–7.72 (m, 1H), 8.55 8.59 (m, 1H). | 328 |

TABLE 70-continued

| Compound Table-(a), (b), (c)- No. | E/Z | ¹H-NMR (CDCl₃) δ | MS (m/e, M⁺) |
|---|---|---|---|
| 4-(a)-12 | E | 2.61 (s, 3H), 5.40 (s, 2H), 7.09 7.50 (m, 6H), 7.66–7.75 (m, 1H), 8.58–8.81 (m, 1H). | 328 |
| 4-(a)-13 | Z | 2.53 (s, 3H), 5.38 (s, 2H), 7.03 (dd, J = 8.7, 8.7 Hz, 2H), 7.20 (dd, J = 4.8, 7.8 Hz, 1H), 7.31 (d, J = 7.8 Hz, 1H), 7.46 (dd, J = 5.4, 8.7 Hz, 2H), 7.87(ddd, J = 1.7, 7.8, 7.8 Hz, 1H), 8.57 (d, J = 4.8 Hz, 1H). | 328 |
| 4-(a)-13 | E | 2.60 (s, 3H), 5.40 (s, 2H), 7.14 (dd, J = 8.8, 8.8 Hz, 2H), 7.21 (m, 1H), 7.35(d, J = 7.8 Hz, 1H), 7.59 (dd, J = 5.4, 8.8 Hz, 2H), 7.70 (ddd, J = 1.7, 7.8, 7.8 Hz, 1H), 8.59 (d, J = 4.8 Hz, 1H). | 328 |
| 4-(b)-13 | Z | 2.48 (s, 3H), 5.36 (s, 2H), 7.03 (t, J = 8.64Hz, 2H, 7.10–7.32 (m, 2H), 7.36–7.60 (m, 2H), 7.67 (t, J = 7.66Hz, 1H), 8.57 (d, J = 4.86Hz, 1H). | 329 (M⁺ + 1) |

TABLE 71

| Compound Table-(a), (b), (c)- No. | E/Z | ¹H-NMR (CDCl₃) δ | MS (m/e, M⁺) |
|---|---|---|---|
| 4-(b)-13 | E | 2.61 (s, 3H), 5.40 (s, 2H), 7.00–7.75 (m, 7H), 8.50–8.60(m, 1H). | 329 (M⁺ + 1) |
| 4-(b)-15 | Z | 2.56 (s, 3H), 5.38 (s, 2H), 6.77 (m, 1H), 6.93 (ddd, J = 2.5. 8.9, 8.9 Hz, 1H), 7.23 (m, 1H), 7.28 (d, J = 8.7 Hz, 2H), 7.6–7.8 (m, 2H), 8.59 (d, J = 4.9 Hz, 1H). | 347 (M⁺ + 1) |
| 4-(a)-19 | Z | 2.54 (s, 3H), 5.40 (s, 2H), 6.78–6.90 (m, 1H), 6.92–7.08 (m, 2H), 7.16–7.34 (m, 2H), 7.62–7.75 (m, 1H), 8.52–8.62 (m, 1H). | 346 |
| 4-(a)-19 | E | 2.62 (s, 3H), 5.40 (s, 2H), 6.78–7.38 (m, 5H), 7.63–7.78 (m, 1H), 8.53–8.62 (m, 1H). | 346 |
| 4-(a)-22 | Z | 2.33 (s, 3H), 2.52 (s, 3H), 5.40 (s, 2H), 7.17–7.41 (m, 6H), 7.61–7.77 (m, 1H), 8.52–8.62 (m, 1H). | 324 |
| 4-(b)-23 | Z | 2.35 (s, 3H), 2.47 (s, 3H), 5.35 (s, 2H), 6.90–7.48 (m, 6H), 7.66 (t, J = 7.67Hz, 1H), 8.56 (d, J = 4.73Hz, 1H). | 324 |
| 4-(b)-23 | E | 2.41 (s, 3H), 2.59 (s, 3H), 5.40 (s, 2H), 6.90–7.75 (m, 7H), 8.50–8.75 (m, 1H). | 324 |
| 4-(a)-33 | Z | 2.55 (s, 3H), 5.43 (s, 2H), 7.22 (dd, J = 4.7, 7.0 Hz, 1H), 7.32 (d, J = 7.8 Hz, 1H), 7.47 (t, J = 7.8 Hz, 1H), 7.58–7.78 (m, 3H), 7.81 (s, 1H), 8.58 (d, J = 4.7 Hz, 1H). | 378 |
| 4-(b)-50 | Z | 2.60 (s, 3H), 3.47 (s, 3H), 5.37 (s, 2H), 6.82 (d, J = 8.3 Hz, 1H), 6.95–7.5 (m), 7.55–7.75 (m), 8.57 (m, 1H). | 340 |
| 4-(a)-52 | Z | 2.52 (s, 3H), 3.81 (s, 3H), 5.37 (s, 2H), 6.86 (d, J = 8.9 Hz, 2H), 7.19 (dd, J = 4.7, 7.3 Hz, 1H), 7.32 (d, J = 7.8 Hz, 1H), 7.40 (d, J = 8.9 Hz, 2H), 7.67 (ddd, J = 1.8, 7.3, 7.8 Hz, 1H), 8.55 (d, J = 4.7 Hz, 1H). | 340 |

TABLE 72

| Compound Table-(a), (b), (c)- No. | E/Z | ¹H-NMR (CDCl₃) δ | MS (m/e, M⁺) |
|---|---|---|---|
| 4-(a)-52 | E | 2.57 (s, 3H), 3.85 (s, 3H), 5.41 (s, 2H), 6.96 (d, J = 8.8 Hz, 2H), 7.21 (dd, J = 4.8, 7.3 Hz, 1H), 7.39 (d, J = 7.8 Hz, 1H), 7.58 (d, J = 8.8 Hz, 2H), 7.69 (ddd, J = 1.7, 7.3, 7.8 Hz, 1H), 8.59 (d, J = 4.8 Hz, 1H). | 340 |
| 4-(b)-52 | Z | 2.41 (s, 3H), 3.82 (s, 3H), 5.34 (s, 2H), 6.85 (d, J = 8.90Hz, 2H), 7.16–7.35 (m, 2H), 7.36 (d, J = 8.90Hz, 2H), 7.67 (t, J = 7.50Hz, 1H), 8.50–8.60 (m, 1H). | 340 |

TABLE 72-continued

| Compound Table-(a), (b), (c)- No. | E/Z | ¹H-NMR (CDCl₃) δ | MS (m/e, M⁺) |
|---|---|---|---|
| 4-(b)-52 | E | 2.57 (s, 3H), 3.86 (s, 3H), 5.41 (s, 2H), 7.00 (d, J = 9.00Hz, 2H), 7.16–7.35 (m, 2H), 7.52 (d, J = 9.00Hz, 2H), 7.60.–7.75 (m, 1H), 8.50–8.65 (m, 1H). | 340 |
| 4-(c)-52 | Z | 2.32 (s, 3H), 3.82 (s, 3H), 5.37 (s, 2H), 6.88 (d, J = 8.96Hz, 2H), 7.17–7.41 (m, 2H), 7.47 (d, J = 8.96Hz, 2H), 7.60–7.28 (m, 1H), 8.50–8.62 (m, 1H). | 324 |
| 5-(a)-17 | Z | 2.55 (s, 3H), 5.45 (s, 2H), 7.18–7.4 (m, 2H), 7.5–7.9 (m, 3H), 8.02 (m), 8.20 (m), 8.2–8.4 (m), 8.59 (m, 1H). | 355 |
| 5-(b)-21 | Z | 2.51 (s, 3H), 5.39 (s, 2H), 7.10–7.80 (m, 12H), 8.57 (d, J = 4.63Hz, 1H). | 386 |
| 5-(b)-21 | E | 2.62 (s, 3H), 5.44 (s, 2H), 7.10–7.80 (m, 12H), 8.57–8.68 (m, 1H). | 386 |
| 5-(a)-24 | Z | 2.54 (s, 3H), 5.40 (s, 2H), 7.12–7.34 (m, 4H), 7.43–7.57 (m, 2H), 7.60–7.73 (m, 1H), 8.51–8.61 (m, 1H). | 394 |
| 5-(a)-24 | E | 2.62 (s, 3H), 5.40 (s, 2H), 7.16–7.38 (m, 4H), 7.56–7.74 (m, 3H), 8.55–8.63 (m, 1H). | 394 |
| 5-(a)-29 | Z | 2.57 (s, 3H), 5.46 (s, 2H), 7.19–7.33 (m, 2H), 7.62–7.75 (m, 1H), 7.86–7.97 (m, 3H), 8.53–8.62 (m, 1H). | 446 |
| 5-(a)-29 | E | 2.70 (s, 3H), 5.41 (s, 2H), 7.19–7.33 (m, 2H), 7.61–7.76 (m, 1H), 7.91–8.03 (m, 3H), 8.55–8.62 (m, 1H). | 446 |

TABLE 73

| Compound Table-(a), (b), (c)- No. | E/Z | ¹H-NMR (CDCl₃) δ | MS (m/e, M⁺) |
|---|---|---|---|
| 6-(b)-2 | Z | 2.36 (s, 3H), 5.20 (s, 2H), 7.04 (s, 1H), 7.25–7.45 (m, 5H), 7.55 (s, 1H). | 299 |
| 6-(b)-4 | Z | 2.35 (s, 3H), 5.28 (s, 2H), 6.33 (d, J = 2.1Hz, 1H), 7.25–7.5 (m, 5H), 7.51 (d, J = 2.1Hz, 1H). | 299 |
| 6-(b)-6 | Z | 2.40 (s, 3H), 5.40 (s, 2H), 7.3–7.5 (m, 5H), 8.06 (s, 1H). | 299 (M⁺ − 1) |
| 6-(a)-18 | Z | 2.48 (s, 3H), 5.45 (s, 2H), 7.28–7.54 (m, 6H), 8.76 (d, J = 2.01Hz, 1H). | 316 |
| 6-(b)-18 | Z | 2.43 (s, 3H), 5.42 (s, 2H), 7.26–7.53 (m, 6H), 8.78 (d, J = 2.02Hz, 1H). | 316 |
| 6-(b)-18 | E | 2.66 (s, 3H), 5.45 (s, 2H), 7.18–7.58 (m, 6H), 8.82 (d, J = 1.99Hz, 1H). | 316 |
| 6-(c)-18 | Z | 2.28 (s, 3H), 5.46 (s, 2H), 7.26–7.60 (m, 6H), 8.80 (d, J = 1.99Hz, 1H). | 300 |
| 6-(a)-19 | Z | 2.50 (s, 3H), 5.54 (s, 2H), 7.30–7.60 (m, 6H), 7.78 (d, J = 3.24Hz, 1H). | 316 |
| 6-(b)-19 | Z | 2.44 (s, 3H), 5.51 (s, 2H), 7.30–7.60 (m, 6H), 7.78 (d, J = 3.34Hz, 1H). | 316 |
| 6-(b)-19 | E | 2.69 (s, 3H), 5.54 (s, 2H), 7.30–7.60 (m, 6H), 7.81 (d, J = 3.35Hz, 1H). | 316 |
| 6-(a)-21 | Z | 2.41 (s, 3H), 5.79 (s, 2H), 7.33–7.62 (m, 5H), 8.64 (s, 1H). | 317 |
| 6-(a)-21 | E | 2.61 (s, 3H), 5.81 (s, 2H), 7.35–7.60 (m, 5H), 8.53 (s, 1H). | 317 |

TABLE 74

| Compound Table-(a), (b), (c)- No. | E/Z | ¹H-NMR (CDCl₃) δ | MS (m/e, M⁺) |
|---|---|---|---|
| 7-(a)-6 | Z | 2.55 (s, 3H), 5.63 (s, 2H), 7.33–7.60 (m, 7H), 7.90 (d, d = 8.00Hz, 1H), 8.03 (d, J = 8.10Hz, 1H). | 366 |

TABLE 74-continued

| Compound Table-(a), (b), (c)- No. | E/Z | ¹H-NMR (CDCl₃) δ | MS (m/e, M⁺) |
|---|---|---|---|
| 7-(a)-8 | Z | 2.39 (s, 3H), 5.56 (s, 2H), 7.10–7.50 (m, 9H), 7.53–7.70 (brd, 1H). | 349 |
| 7-(b)-8 | Z | 2.42 (s, 3H), 5.52 (s, 2H), 7.20–7.60 (m, 9H), 7.60–7.90 (brd, 1H). | 349 |
| 7-(a)-10 | Z | 2.51 (s, 3H), 5.46 (s, 2H), 6.74 (t, J = 6.75Hz, 1H), 7.13 (t, J = 6.96Hz, 1H), 7.30–7.60 (m, 7H), 8.05 (d, J = 6.75Hz, 1H). | 349 |
| 7-(b)-10 | Z | 2.47 (s, 3H), 5.44 (s, 2H), 6.75 (t, J = 6.57Hz, 1H), 7.15(t, J = 6.64Hz, 1H), 7.30–7.70 (m, 7H), 8.05 (d, J = 6.80Hz, 1H). | 349 |
| 8-(a)-1 | Z | 2.50 (s, 3H), 4.90–5.15 (brd, 2H), 5.13 (s, 2H), 6.45 (s, 1H), 7.29–7.55 (m, 5H). | 332 (M⁺ + 1) |
| 8-(b)-1 | Z | 2.45 (s, 3H), 5.09 (s, 2H), 5.20–5.38 (brd, 2H), 6.39 (s, 1H), 7.30–7.52 (m, 5H). | 331 |
| 8-(b)-1 | E | 2.68 (s, 3H), 5.10 (s, 2H), 5.39–5.50 (brd, 2H), 6.40 (s, 1H), 7.30–7.52 (m, 5H). | 331 |
| 9-(c)-1 | Z | 2.31 (s, 3H), 4.83–510 (brd, 1H), 5.14 (s, 2H), 6.46 (s, 1H), 7.32–7.66 (m, 5H). | 315 |
| 8-(b)-2 | Z | 2.35 (s, 3H), 5.20 (s, 2H), 6.99 (s, 1H), 7.30–7.50 (m, 5H), 8.33 (m, 1H). | 359 |
| 8-(b)-3 | Z | 2.15 (s, 3H), 2.38 (s, 3H), 5.22 (s, 2H), 6.91 (s, 1H) 7.30–7.55 (m, 5H). | 373 |
| 8-(b)-3 | E | 2.15 (s, 3H), 2.64 (s, 3H), 5.24 (s, 2H), 6.92 (s, 1H) 7.30–7.55 (m, 5H). | 373 |

TABLE 75

| Compound Table-(a), (b), (c)- No. | E/Z | ¹H-NMR (CDCl₃) δ | MS (m/e, M⁺) |
|---|---|---|---|
| 8-(b)-4 | Z | 1.21 (t, J = 7.48Hz, 3H), 2.39 (s, 3H), 2.42 (q, J = 7.48Hz, 2H), 5.21 (s, 2H), 6.89 (s, 1H) 7.28–7.50 (m, 5H). | 387 |
| 8-(b)-4 | E | 1.25 (t, J = 7.57Hz, 3H), 2.42 (s, 3H), 2.46 (q, J = 7.57Hz, 2H), 5.21 (s, 2H), 6.88 (s, 1H) 7.29–7.57 (m, 5H). | 387 |
| 8-(a)-7 | Z | 1.25 (d, J = 6.95Hz, 6H), 2.46 (s, 3H), 2.50–2.70 (m, 1H), 5.24 (s, 1H), 6.91 (s, 1H), 7.28–7.50 (m, 5H), 9.20–9.45 (brd, 1H). | 401 |
| 8-(b)-7 | Z | 1.22 (d, J = 6.91Hz, 6H), 2.41 (s, 3H), 2.47–2.76(m, 1H), 5.21 (s, 2H), 6.89 (s, 1H), 7.28–7.60 (m, 5H), 9.50–9.90 (brd, 1H). | 401 |
| 8-(c)-7 | Z | 1.27 (d, J = 6.95Hz, 6H), 2.28 (s, 3H), 2.50–2.75 (m, 1H), 5.25 (s, 2H), 6.91 (s, 1H), 7.30–7.62 (m, 5H), 8.90–9.10 (brd, 1H). | 385 |
| 8-(b)-8 | Z | 0.97 (d, J = 6.39Hz, 6H), 2.08–2.36 (m, 3H), 2.41 (s, 3H), 5.22 (s, 2H), 6.87 (s, 1H), 7.30–7.52 (m, 5H), 9.54–9.80 (brd, 1H). | 415 |
| 8-(c)-8 | Z | 0.97 (d, J = 6.45Hz, 6H), 2.20–2.30 (m, 3H), 2.25 (s, 3H), 5.25 (s, 2H), 6.91 (s, 1H), 7.30–7.60 (m, 5H), 9.59–9.83 (brd, 1H). | 399 |
| 8-(b)-9 | Z | 0.92 (t, J = 8.0Hz, 3H), 1.23 (d, J = 6.89Hz, 3H), 1.42–1.90 (m, 2H), 2.25–2.50 (m, 1H), 2.43 (s, 3H), 5.22 (s, 2H), 6.88 (s, 1H), 7.28–7.52 (m, 5H), 9.15–9.40 (brd, 1H). | 415 |
| 8-(b)-10 | Z | 1.32 (s, 9H), 2.44 (s, 3H), 5.22 (s, 2H), 6.88 (s, 1H), 7.28–7.59 (m, 5H), 8.86–9.09 (brd, 1H). | 415 |
| 8-(c)-10 | Z | 1.33 (s, 9H), 2.29 (s, 3H), 5.26 (s, 2H), 6.91 (s, 1H), 7.30–7.60 (m, 5H), 8.76–8.99 (brd, 1H). | 399 |

TABLE 76

| Compound Table-(a), (b), (c)-No. | E/Z | $^1$H-NMR (CDCl$_3$) δ | MS (m/e, M$^+$) |
|---|---|---|---|
| 8-(b)-13 | Z | 0.89 (t, J = 7.42Hz, 6H), 1.40–1.88 (m, 4H), 2.04–2.21 (m, 1H), 2.43 (s, 3H), 5.23 (s, 2H), 6.88 (s, 1H), 7.29–7.50 (m, 5H), 9.28–9.52 (brd, 1H). | 429 |
| 8-(b)-14 | Z | 2.42 (s, 3H), 5.23 (s, H), 7.10 (s, 1H), 7.30–7.50 (m, 5H), 8.90–9.20 (brd, 1H). | 427 |
| 8-(c)-14 | Z | 2.26 (s, 3H), 5.26 (s, 2H), 7.07 (s, 1H), 7.28–7.56 (m, 5H), 7.68–8.10 (brd, 1H). | 411 |
| 8-(b)-16 | Z | 2.43 (s, 3H), 5.23 (s, 2H), 7.02 (s, 1H), 7.29–7.56 (m, 5H). | 527 |
| 8-(b)-17 | Z | 2.44 (s, 3H), 4.27 (s, 2H), 5.24 (s, 2H), 6.94 (s, 1H) 7.30–7.52 (m, 5H), 9.50–9.75 (brd., 1H). | 407 |
| 8-(b)-18 | Z | 2.45 (s, 3H), 5.25 (s, 2H), 6.15 (s, 1H), 6.99 (s, 1H), 7.30–7.60 (m, 5H), 9.10–10.3 (brd, 1H). | 441 |
| 8-(b)-18 | E | 2.67 (s, 3H), 5.28 (s, 2H), 6.16 (s, 1H), 6.99 (s, 1H) 7.30–7.60 (m, 5H), 9.10–10.3 (brd, 1H). | 441 |
| 8-(b)-19 | Z | 2.45 (s, 3H), 5.24 (s, 2H), 7.03 (s, 1H), 7.28–7.52 (m, 5H). | 476 (M$^+$ + 1) |
| 8-(b)-19 | E | 2.67 (s, 3H), 5.27 (s, 2H), 7.03 (s, 1H), 7.28–7.52 (m, 5H). | 476 (M$^+$ + 1) |
| 8-(b)-20 | Z | 2.06 (s, 6H), 2.45 (s, 3H), 5.23 (s, 2H), 6.93 (s, 1H) 7.30–7.53 (m, 5H). | 479 |
| 8-(b)-20 | E | 2.05 (s, 6H) 2.68 (s, 3H), 5.26 (s, 2H), 6.94 (s, 1H) 7.30–7.50 (m, 5H). | 479 |
| 8-(b)-21 | Z | 2.44 (s, 3H), 5.25 (s, 2H), 7.15 (s, 1H), 7.30–7.56 (m, 5H), 10.80–11.15 (brd, 1H). | 443 |
| 8-(b)-21 | E | 2.65 (s, 3H), 5.26 (s, 2H), 7.06 (s, 1H), 7.29–7.50 (m, 5H). | 443 |

TABLE 77

| Compound Table-(a), (b), (c)-No. | E/Z | $^1$H-NMR (CDCl$_3$) δ | MS (m/e, M$^+$) |
|---|---|---|---|
| 8-(b)-22 | Z | 2.41 (s, 3H), 3.84 (s, 3H), 5.21 (s, 2H), 6.85 (s, 1H) 7.29–7.50 (m, 5H). | 389 |
| 9-(b)-2 | Z | 2.47 (s, 3H), 2.92 (s, 3H), 5.12 (s, 2H), 6.39 (s, 1H) 7.30–7.52 (m, 5H). | 345 |
| 9-(b)-6 | Z | 2.41 (s, 3H), 5.02 (s, 2H), 6.23 (s, 1H), 6.63 (s, 1H) 7.20–7.50 (m, 20H). | 574 (M$^+$ + 1) |
| 9-(c)-6 | Z | 2.23 (s, 3H), 5.11 (s, 2H), 6.27 (s, 1H), 6.80–6.97 (brd, 1H), 7.13–7.60 (m, 20H). | 557 |
| 9-(b)-7 | Z | 1.26 (d, J = 6.77Hz, 6H), 2.48 (s, 3H), 2.93–3.23 (m, 1H), 3.75 (s, 3H), 5.25 (s, 2H), 6.90 (s, 1H), 7.30–7.53 (m, 5H). | 415 |
| 9-(b)-8 | Z | 2.15 (s, 3H), 3.07 (s, 6H), 5.14 (s, 2H), 6.37 (s, 1H) 7.2–7.51 (m, 5H). | 359 |
| 9-(b)-9 | Z | 2.45 (s, 3H), 2.17 (s, 3H), 5.13 (s, 2H), 7.04 (s, 1H) 7.28–7.55 (m, 5H). | 330 |
| 9-(b)-14 | Z | 2.45 (s, 3H), 5.41 (s, 2H), 7.30–7.60 (m, 6H). | 384 |
| 9-(b)-14 | E | 2.66 (s, 3H), 5.44 (s, 2H), 7.30–7.60 (m, 6H). | 384 |
| 9-(b)-16 | Z | 2.44 (s, 3H), 5.34 (s, 2H), 7.30–7.52 (m, 5H), 8.76 (s, 1H). | 394 |
| 9-(b)-16 | E | 2.67 (s, 3H), 5.36 (s, 2H), 7.30–7.50 (m, 5H), 8.79 (s, 1H). | 394 |
| 9-(b)-20 | Z | 1.35 (d, J = 6.85Hz, 6H), 2.44 (s, 3H), 3.95–4.22 (m, 1H), 4.95 (s, 2H), 6.16 (s, 1H), 7.30–7.55 (m, 5H). | 374 |
| 9-(b)-21 | Z | 0.88 (d, J = 6.47Hz, 6H), 1.32–1.67 (m, 3H), 2.42 (s, 3H), 3.50–3.73 (m, 2H), 4.98 (s, 2H), 6.20 (s, 1H), 7.30–7.52 (m, 5H). | 402 |

TABLE 78

| Compound Table-(a), (b), (c)-No. | E/Z | $^1$H-NMR (CDCl$_3$) δ | MS (m/e, M$^+$) |
|---|---|---|---|
| 9-(b)-22 | Z | 2.46 (s, 3H), 5.15 (s, 2H), 6.80 (s, 1H), 7.22 (t, J = 71.7 Hz, 1H), 7.25–7.50 (5H, m). | 414 |
| 9-(b)-23 | Z | 2.46 (s, 3H), 2.67 (s, 3H), 5.29 (s, 2H), 7.06 (s, 1H), 7.25–7.5 (m, 5H). | 362 |
| 9-(b)-26 | Z | 1.40 (d, J = 6.7 Hz, 6H), 2.45 (s, 3H), 3.77 (sep, J = 6.7 Hz, 1H), 5.30 (d, J = 0.7 Hz, 2H), 7.11 (s, 1H), 7.25–7.5 (m, 5H). | 390 |
| 10-(b)-2 | Z | 2.45 (s, 3H), 5.36 (d, J = 0.6 Hz, 2H), 7.23 (t, J = 56.5 Hz, 1H), 7.25–7.5 (m, 5H). | 398 |
| 10-(b)-3 | Z | 2.46 (s, 3H), 3.30 (s, 3H), 5.41 (s, 2H), 7.3–7.5 (m, 5H), 7.61 (s, 1H). | 394 |
| 10-(b)-4 | Z | 1.40 (d, J = 6.9 Hz, 6H), 2.45 (s, 3H), 3.59 (sep, J = 6.9 Hz, 1H), 5.42 (s, 2H), 7.25–7.5 (m, 5H), 7.63 (s, 1H). | 422 |
| 10-(b)-5 | Z | 2.43 (s, 3H), 5.40 (s, 2H), 6.45 (t, J = 54.4Hz, 1H), 7.25–7.5 (m, 5H), 7.68 (s, 1H). | 414 |
| 10-(b)-6 | Z | 2.44 (s, 3H), 5.47 (s, 2H), 6.46 (t, J = 53.1Hz, 1H), 7.25–7.5 (m, 5H), 7.86 (s, 1H). | 430 |
| 10-(b)-7 | Z | 1.27 (d, J = 6.78Hz, 6H), 2.44 (s, 3H), 2.80–3.10 (m, 1H), 4.02 (s, 2H), 5.31 (s, 2H), 7.16 (s, 1H), 7.30–7.52 (m, 5H). | 405 |
| 10-(b)-8 | Z | 1.41 (t, J = 7.16Hz, 3H), 2.47 (s, 3H), 4.43 (q, J = 7.16Hz, 2H), 5.53 (s, 2H), 7.30–7.56 (m, 5H), 8.18 (s, 1H). | 388 |
| 10-(b)-11 | Z | 1.27 (d, J = 6.56Hz, 6H), 2.45 (s, 3H), 4.15–4.42 (m, 1H), 5.44 (s, 2H), 7.00–7.20 (brd, 1H), 7.30–7.54 (m, 5H) 8.09 (s, 1H). | 401 |
| 10-(b)-14 | Z | 2.37 (s, 3H), 2.60 (s, 3H), 3.45 (s, 3H), 5.15 (s, 2H), 7.11 (s, 1H), 7.25–7.45 (m, 5H). | 359 |
| 10-(b)-15 | Z | 2.39 (s, 3H), 3.37 (s, 3H), 3.88 (s, 3H), 5.20 (s, 2H), 7.16 (s, 1H), 7.25–7.5 (m, 5H). | 392 |

TABLE 79

| Compound Table-(a), (b), (c)-No. | E/Z | $^1$H-NMR (CDCl$_3$) δ | MS (m/e, M$^+$) |
|---|---|---|---|
| 10-(b)-16 | Z | 2.45 (s, 3H), 2.83 (s, 6H), 5.20 (s, 2H), 7.22 (d, J = 1.2 Hz, 1H), 7.3–7.5 (m, 5H), 7.85 (d, J = 1.2 Hz, 1H). | 406 |
| 10-(b)-20 | Z | 2.33 (s, 3H), 5.32 (s, 2H), 7.05–7.2 (m, 6H), 7.2–7.5 (m, 14H), 7.94 (s, 1H). | 542 |
| 11-(b)-1 | Z | 2.46 (s, 3H), 5.14 (s, 2H), 6.97 (brd., 2H), 7.25–7.55 (m, 5H). | 333 (M$^+$ + 1) |
| 11-(b)-3 | Z | 2.24 (s, 3H), 2.41 (s, 3H), 5.33 (s, 2H), 7.2–7.5 (m, 5H). | 375 (M$^+$ + 1) |
| 11-(b)-7 | Z | 1.25 (d, J = 7.0 Hz, 6H), 2.47 (s, 3H), 2.70 (m, 1H), 5.32 (s, 2H), 7.25–7.45 (m, 5H). | 403 (M$^+$ + 1) |
| 11-(b)-10 | Z | 0.85–1.35 (m), 1.55–2.0 (m), 2.39 (d, J = 6.9 Hz, 2H), 2.51 (s, 3H), 5.32 (s, 2H), 7.25–7.5 (m, 5H). | 457 (M$^+$ + 1) |
| 11-(b)-11 | Z | 2.46 (s, 3H), 5.33 (s, 2H), 7.25–7.45 (m, 5H). | 359 (M$^+$ − CF$_3$) |
| 11-(b)-12 | Z | 2.45 (s, 3H), 5.18 (s, 2H), 7.25–7.45(m, 5H), 7.5–7.6 (m, 2H), 7.6–7.7 (m, 1H), 7.9–8.0 (m, 2H). | 437 (M$^+$ + 1) |
| 11-(b)-13 | Z | 2.41 (s, 3H), 3.84 (s, 3H), 5.34 (s, 2H), 7.2–7.45 (m, 5H). | 391 (M$^+$ + 1) |
| 11-(b)-14 | Z | 2.48 (s, 3H), 5.19 (s, 2H), 7.15–7.5 (m, 20H). | 574 |

TABLE 80

| Compound Table-(a), (b), (c)- No. | E/Z | $^1$H-NMR (CDCl$_3$) δ | MS (m/e, M$^+$) |
|---|---|---|---|
| 13-(a)-2 | Z | 1.26 (d, J = 6.8 Hz, 6H), 2.47 (s, 3H), 2.61 (sep, J = 6.8 Hz, 1H), 5.25 (s, 2H), 6.90 (s, 1H), 7.25–7.40 (m, 3H), 7.50 (m, 1H). | 435 |
| 13-(a)-3 | Z | 1.27 (d, J = 6.9 Hz, 6H), 2.48 (s, 3H), 2.61 (sep, J = 6.9 Hz, 1H), 5.24 (s, 2H), 6.89 (s, 1H), 7.32 (d, J = 8.5 Hz, 2H), 7.41 (d, J = 8.5 Hz, 2H), 8.80 (brd, 1H). | 435 |
| 13-(b)-3 | Z | 1.26 (d, J = 6.85Hz, 6H), 2.42 (s, 3H), 2.50–2.74 (m, 1H), 5.20 (s, 2H), 6.87 (s 1H), 7.20–7.45 (m, 4H), 9.08–9.29 (brd, 1H). | 435 |
| 13-(a)-8 | Z | 1.28 (d, J = 6.7 Hz, 6H), 2.49 (s, 3H), 2.62 (sep, J = 6.7 Hz, 1H), 5.25 (s, 2H), 6.90 (s, 1H), 7.29 (dd, J = 2.0, 8.5 Hz, 1H), 7.42 (d, J = 8.5 Hz, 1H), 7.60 (d, J = 2.0 Hz, 1H), 8.72 (brd, 1H). | 469 |
| 13-(a)-9 | Z | 1.28 (d, J = 7.1 Hz, 6H), 2.49 (s, 3H), 2.62 (sep, J = 7.1 Hz, 1H), 5.25 (s, 2H), 6.90 (s, 1H), 7.37 (m, 3H), 8.81 (brd, 1H). | 469 |
| 13-(b)-12 | Z | 1.28 (d, J = 7.0 Hz, 6H), 2.43 (s, 3H), 2.62 (sep, J = 7.0 Hz, 1H), 5.21 (s, 2H), 6.88 (s, 1H), 7.0–7.4 (m, 4H), 8.95 (brd, 1H). | 469 |
| 13-(b)-13 | Z | 2.27 (d, J = 6.88Hz, 6H), 2.43 (s, 3H), 2.50–2.74 (m, 1H), 5.20 (s, 2H), 6.87 (s, 1H). 7.20–7.45 (m, 4H), 9.08–9.29 (brd, 1H). | 419 |
| 13-(b)-33 | Z | 1.26 (d, J = 7.0 Hz, 6H), 2.44 (s, 3H), 2.61 (sep, J = 7.0 Hz, 1H), 5.25 (s, 2H), 6.89 (s, 1H), 7.46 (dd, J = 7.5, 8.1 Hz, 1H), 7.55 (d, J = 8.1 Hz, 1H), 7.65 (d, J = 7.5 Hz, 1H), 7.79 (s, 1H), 9.25 brd, 1H). | 469 |

TABLE 81

| Compound Table-(a), (b), (c)- No. | E/Z | $^1$H-NMR (CDCl$_3$) δ | MS (m/e, M$^+$) |
|---|---|---|---|
| 23-(b)-12 | Z | 1.00 (d, J = 6.4 Hz, 6H), 2.1–2.4 (m, 3H), 2.41 (s, 3H), 5.20 (s, 2H), 6.86 (s, 1H), 7.0–7.4 (m, 4H), 9.9–10.0 (br, 1H). | 433 |
| 35-(b)-12 | Z | 2.46 (s, 3H), 4.95 (brd, 2H), 5.11 (s, 2H), 6.43 (s, 1H), 7.0–7.2 (m, 2H), 7.2–7.4 (m, 2H). | 349 |
| 61-(b)-6 | Z | 2.48 (s, 3H), 5.42 (s, 2H), 7.29–7.50 (m, 5H), 7.78 (d, J = 6.16Hz, 2H), 8.70 (d, J = 6.16Hz, 2H). | 393 |
| 61-(b)-14 | Z | 0.80–1.00 (m, 2H), 1.10–1.23 (m, 2H), 1.45–1.70 (m, 1H), 2.37 (s, 3H), 5.23 (s, 2H), 6.89 (s, 1H), 7.30–7.50 (m, 5H), 10.8–11.0 (brd, 1H). | 399 |
| 61-(b)-17 | Z | 1.12–2.03 (m, 10H), 2.20–2.42 (m, 1H), 2.42 (s, 3H), 5.22 (s, 2H), 6.87 (s, 1H), 7.30–7.50 (m, 5H), 9.10–9.40 (brd, 1H). | 441 |
| 61-(b)-19 | Z | 2.35 (s, 1H), 4.93 (s, 2H), 6.90 (s, 1H), 7.30–7.70 (m, 8H), 7.85–8.00 (m, 2H). | 436 (M$^+$ + 1) |
| 63-(b)-20 | Z | 2.41 (s, 3H), 5.19 (s, 2H), 6.92 (s, 1H), 7.15 (dd, J = 3.9, 4.8 Hz, 1H), 7.39–7.50 (m, 5H), 7.64 (d, J = 4.8 Hz, 1H) , 7.73 (d, J = 3.9 Hz, 1H). | 441 |
| 64-(b)-17 | Z | 2.40–2.55 (m, 6H), 3.90–4.15 (m, 1H), 5.22 (s, 2H), 7.29 (s, 1H), 7.40–7.55 (m, 5H). 8.20–8.60(m, 3H)[1]. | 403 (M$^+$ + 1) |
| 64-(b)-18 | Z | | 431 (M$^+$ + 1) |
| 64-(b)-21 | Z | 1.30–1.60 (m, 3H), 1.48 (s, 9H), 2.43 (s, 3H), 4.20–4.50 (m, 1H), 5.20 (s, 2H), 6.88 (s, 1H), 7.30–7.50 (m, 5H). | 503 (M$^+$ + 1) |
| 64-(b)-22 | Z | 0.94 (d, J = 6.8 Hz, 3H), 1.00 (d, J = 6.8 Hz, 3H), 1.45 (s, 9H), 2.43 (s, 3H), 4.16–4.40 (m, 1H), 5.21 (s, 2H), 6.88 (s, 1H), 7.30–7.50 (m, 5H). | 531 (M$^+$ + 1) |
| 65-(b)-12 | Z | 1.11 (d, J = 6.76Hz, 6H), 1.42 (s, 9H), 2.44 (s, 3H), 4.57 (s, 2H), 5.31 (s, 2H), 7.15 (s, 1H), 7.30–7.50 (m, 5H). | 488 (M$^+$ + 1) |

[1] Measured in DMSO-d$_6$

The representations of respective compounds in these tables indicate that a compound, for example, represented by Compound No. 1-(a)-1 is one of the compounds shown in Table 1 and Het B of which is type (a).

Hereinafter, examples of formulating agricultural chemicals using compounds of oxime derivatives obtained by present invention will be described. Unless otherwise shown, the compounds are mixtures of the "Z" and the "E" forms.

FORMULATING EXAMPLE 1

Dust powder 2 parts by weight of the oxime derivatives from Compound No. 1-(a)-1 to Compound No. 66-(b)-10 were mixed with 98 parts by weight of clay and the mixture was pulverized so that dusting powder was produced.

FORMULATING EXAMPLE 2

Water-dispersible powder 20 parts by weight of the oxime derivatives from Compound No. 1-(a)-1 to Compound No. 66-(b)-10 were mixed with 68 parts by weight of clay, 8 parts by weight of white carbon, and 4 parts by weight of polyoxyethylenenonylphenylether and the mixture was pulverized so that water-dispersible powder was produced.

FORMULATION EXAMPLE 3

Granular 5 parts by weight of the oxime derivatives from Compound No. 1-(a)-1 to Compound No. 66-(b)-10 were mixed with 90 parts by weight of a mixture of equivalent weights of bentonite and talc and 5 parts by weight of sodium alkylbenzenesulfonate and the mixture was pulverized for forming granules.

The effectiveness of the compounds obtained by the present invention against various plant diseases will be hereinafter described with reference to following test examples. The status of the test plants at the time of testing the control effects of the present chemicals, that is, the degree of lesions appearing on foliage or the number of plants attacked by Phytophthora are visually observed, and the results were evaluated by four grades "A", "B", "C", and "D". Grade "A" was selected when there is no plant with lesions or no withered plant, and grade "B" was selected when the number of diseased plants, which include plants with lesions or withered plants, is around 10% among the total numbers of plants. Grade "C" was selected when the number of diseased plant is around 25%, and grade "D" was selected when the diseased plants exceed 50%.

TEST EXAMPLE 1

Control Test of Plant Disease Caused by *Phytophthora infestans*

The water-dipersable powder prepared by the method shown in Formulation Example 2 was diluted with water containing a surface active agent (0.02%) so as to contain the effective component at a concentration of 250 ppm. The thus prepared solution was sprayed on foliage at the 3 to 4 leaf stage of tomatoes (variety: Toyofuku) which were grown in plastic pots with a diameter of 9 cm. After drying in air, a dispersion of spores of Phytophthora infestans was spray-inoculated and, after standing in a wet room at 20° C. for 24hours, the spores were made grow at room temperature. After 5 days, the degree of disease was determined. The test results in terms of *Phytophthora infestans* of tomato are shown in Table 82. Water dispersible powder of manzeb in amounts of 1,250 ppm and 250 ppm was used as a reference agricultural chemical.

TABLE 82

| Compound number | Evaluation |
|---|---|
| 1-(a)-1 | A |
| 1-(b)-9 | B |
| 4-(a)-3 | B |
| 4-(a)-13 | A |
| 4-(b)-13 | B |
| 4-(a)-22 | B |
| 4-(a)-33 | A |
| 6-(a)-18 | B |
| 6-(a)-19 | B |
| 6-(b)-19 | B |
| 8-(a)-1 | B |
| 8-(b)-4 | B |
| 8-(a)-7 | A |
| 8-(b)-7 | A |
| 8-(c)-7 | A |
| 8-(b)-8 | B |
| 8-(b)-9 | B |
| 8-(b)-10 | B |
| 8-(b)-14 | B |
| 13-(a)-2 | A |
| Reference chemical | |
| 1250 ppm | A |
| 250 ppm | C |

TEST EXAMPLE 2

Control Test of Plant Disease Caused by
*Pseudoperonospora cubensis*

The water-dipersable powder prepared by the method shown in Formulation Example 2 was diluted with water containing a surface active agent (0.02%) so as to contain the effective component at a concentration of 50 ppm. The thus prepared solution was sprayed on foliage at the 3 leaf stage of a cucumber (variety: Tokiwa Shinchibai) which was grown in a plastic pot with a diameter of 9 cm. After drying in air, a dispersion of spores of Pseudoperonospora cubensis was spray-inoculated and, after standing in a wet room at 25° C. for 24hours, the spores were made grow at room temperature. After 5 days, the degree of disease was determined. The test results in terms of *Pseudoperonospora cubensis* of cucumber are shown in Table 83. Water dispersible powder of manzeb in amounts of 1,250 ppm and 50 ppm was used as a reference agricultural chemical.

TABLE 83

| Compound number | Evaluation |
|---|---|
| 1-(a)-1 | A |
| 1-(b)-1 | A |
| 6-(a)-18 | A |
| 8-(a)-1 | B |
| 8-(b)-3 | A |
| 8-(b)-7 | A |
| 8-(c)-7 | A |
| 8-(b)-9 | A |
| 8-(b)-10 | A |
| 8-(b)-14 | B |
| 13-(a)-2 | B |
| 13-(b)-13 | A |

TABLE 83-continued

| Compound number | Evaluation |
|---|---|
| Reference chemical | |
| 1250 ppm | A |
| 50 ppm | D |

TEST EXAMPLE 3

Control Test of Plant Disease Caused by
*Pseudoperonospora cubensis* (Leaf disc test)

The first leaf of a cucumber (variety: Tokiwa Shinchibai) at a 2 to 3 leaf stage was stamped into a disc with a diameter of 10 mm. The disc was then immersed for 30 minutes in a solution of a pharmaceutical chemical at an effective ingredient concentration of 10 ppm using a water-dispersible powder prepared according to the Formulating Example 2. After drying in air, a dispersion of spores of *Pseudoperonospora cubensis* (a metalaxyl resistant fungi strain) was drop-inoculated. Standing in a wet room, the bacteria was cultured in an artificial weathering equipment (14 hours a day, 2° C. in a day, 18° C. at night) for 7 days, and the degree of the disease was determined. The test result of this leaf test in relation to *Pseudoperonospora cubensis* is shown in Table 84. A 10 ppm of the water-dispersible powder of manzeb and that of metalaxyl was used as the reference agricultural chemical.

TABLE 84

| Compound number | Evaluation | Reference chemical | Evaluation |
|---|---|---|---|
| 1-(a)-1 | A | Manzeb | C |
| 8-(b)-1 | A | Metalaxyl | D |
| 8-(b)-3 | A | | |
| 8-(b)-4 | A | | |
| 8-(b)-7 | A | | |
| 8-(b)-8 | A | | |
| 8-(b)-9 | A | | |
| 8-(b)-13 | A | | |
| 8-(b)-18 | B | | |
| 9-(b)-16 | A | | |
| 9-(b)-22 | B | | |
| 9-(b)-23 | A | | |
| 9-(b)-26 | A | | |
| 10-(b)-2 | B | | |
| 10-(b)-5 | B | | |
| 13-(a)-2 | A | | |
| 13-(b)-3 | A | | |
| 13-(b)-12 | A | | |
| 13-(b)-13 | A | | |
| 13-(b)-33 | A | | |
| 61-(b)-6 | A | | |
| 61-(b)-14 | A | | |
| 61-(b)-19 | A | | |
| 63-(b)-20 | B | | |

TEST EXAMPLE 4

Control Test of Plant Disease Caused by
*Plasmopara viticola* (leaf disc test)

A leaf disc formed by stamping a leaf of an alley grown vine (variety: neo masukatto) was immersed in a chemical-containing solution which was prepared using a water-dispersible powder at an effective component concentration of 10 ppm for 30 min. After drying in air, a dispersion of spores of two fungi consisting of (A) metalaxyl-sensitive *Plasmopara viticola* and (B) metalaxyl-resistant *Plasmopara viticola* was drop-inoculated, and the fungi was cultured for seven days in a wet room by an artificial weathering instrument. The test result of this leaf test in relation to *Plasmopara viticola* was shown in Table 85.

TABLE 85

| Compound number | Evaluation | |
|---|---|---|
| | Metalaxyl-sensitive *Plasmopara viticola* A | Metalaxyl-resistant *Plasmopara viticola* B |
| 8-(b)-4 | A | A |
| 8-(b)-4 | A | A |
| 8-(b)-4 | A | A |
| 8-(b)-10 | A | A |
| 8-(b)-13 | B | B |
| 61-(b)-14 | B | B |
| 61-(b)-19 | A | A |
| Reference chemical | | |
| Manzeb | C | C |
| Metalaxyl | A | D |

TEST EXAMPLE 5

Control Test of a Plant Disease Caused by *Pythium aphanidermatum*

A mixture of sterilized soil and *Pythium aphanidermatum* was put in a deep petri-dish with a diameter of 15 cm. After seeding 10 seeds of cucumber (variety: Nouryoku Shintokiwa) for each pot, a water-diluted dispersion of water-dispersible powder prepared according to the Formulating Example 2 at the effective component concentration of 1,000 ppm was drenched on the soil. After drenched, the pot was placed in a wet room and was subjected to a weathering instrument with a day-length of 14 hours for 4 days. The degree of the plant disease was determined. The test result in relation to Pythium aphanidermatum was shown in Table 86. The reference agricultural chemical of this test was 1,000 ppm of a water-dispersible powder of captan.

TABLE 86

| Compound number | Evaluation |
|---|---|
| 1-(a)-1 | A |
| 8-(b)-7 | A |
| 8-(b)-10 | A |
| Reference chemical | B |

TEST EXAMPLE 6

Control Test of a Plant Disease Caused by *Pyricularia oryzae*

A water diluted solution of a water-dispersible powder prepared according to Formulating Example 2 at an effective component concentration of 250 ppm was sprayed on foliage of a rice plant (variety: Aichi Asahi) at a 3 to 4 leaf stage which was grown in a plastic pot with a diameter of 9 cm. After drying in air, a dispersion of spores of *Pyricularia oryzae* was spray-inoculated, and after standing in a wet room for 24 hours, the plant disease was developed in a glass house, and the degree of the plant disease was determined after 7 days. The test result in relation to *Pyricularia oryzae* was shown in Table 87. The reference agricultural chemical of this test was 500 ppm of a water-dispersible powder of phthalide.

TABLE 87

| Compound number | Evaluation |
|---|---|
| 1-(a)-1 | A |
| 1-(a)-9 | A |
| 1-(b)-9 | A |
| 4-(a)-3 | A |
| 4-(a)-13 | A |
| 4-(a)-22 | B |
| 6-(a)-18 | A |
| 6-(b)-18 | A |
| 6-(a)-19 | B |
| 6-(b)-19 | B |
| Reference chemical | |
| 500 ppm | A |
| 250 ppm | B |

Furthermore, the practical structures of compounds of the present invention are shown in Table 88 to 90, wherein Het B, Het C, X, Y, and n are the same as those defined in the general formulas (1) and (2), and Me represents a methyl group.

TABLE 88

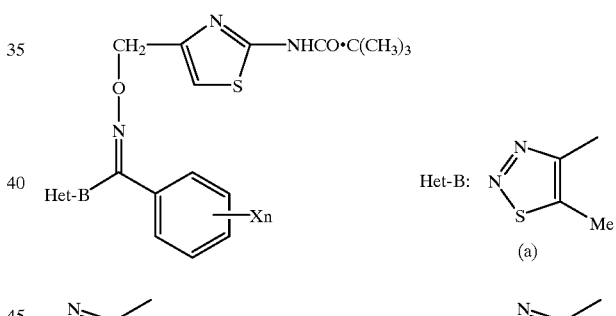

| No | Xn |
|---|---|
| 1 | 2-Cl |
| 2 | 3-Cl |
| 3 | 4-Cl |
| 4 | 2,3-(Cl)$_2$ |
| 5 | 2,4-(Cl)$_2$ |
| 6 | 2,5-(Cl)$_2$ |
| 7 | 2,6(Cl)$_2$ |
| 8 | 3,4-(Cl)$_2$ |
| 9 | 3,5-(Cl)$_2$ |
| 10 | 2,4,6-(Cl)$_3$ |
| 11 | 2-F |
| 12 | 3-F |
| 13 | 4-F |
| 14 | 2,3-(F)$_2$ |
| 15 | 2,4-(F)$_2$ |
| 16 | 2,5-(F)$_2$ |
| 17 | 2,6-(F)$_2$ |
| 18 | 3,4-(F)$_2$ |

TABLE 88-continued

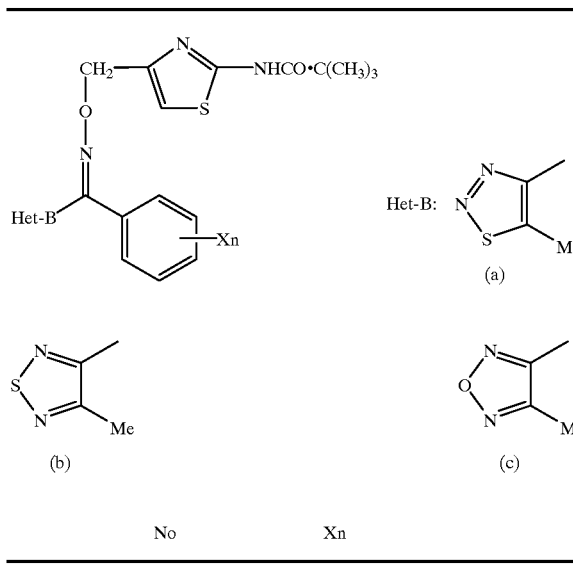

| No | Xn |
|---|---|
| 19 | 3,5-(F)₂ |
| 20 | 2,4,6-(F)₃ |
| 21 | 2-CH₃ |
| 22 | 3-CH₃ |
| 23 | 4-CH₃ |
| 24 | 2,3-(CH₃)₂ |
| 25 | 2,4-(CH₃)₂ |
| 26 | 2,5-(CH₃)₂ |
| 27 | 2,6-(CH₃)₂ |
| 28 | 3,5-(CH₃)₂ |
| 29 | 3-Cl,5-CH₃ |
| 30 | 3-F,5-CH₃ |
| 31 | 3-F,5-Cl |
| 32 | 2-CF₃ |
| 33 | 3-CF₃ |
| 34 | 4-CF₃ |
| 35 | 2-CN |
| 36 | 3-CN |
| 37 | 4-CN |
| 38 | 2-SMe |
| 39 | 3-SMe |
| 40 | 4-SMe |
| 41 | 2-SO₂Me |
| 42 | 3-SO₂Me |
| 43 | 4-SO₂Me |
| 44 | 2-Br |
| 45 | 3-Br |
| 46 | 4-Br |
| 47 | 2-OH |
| 48 | 3-OH |
| 49 | 4-OH |
| 50 | 2-OMe |
| 51 | 3-OMe |
| 52 | 4-OMe |

TABLE 89

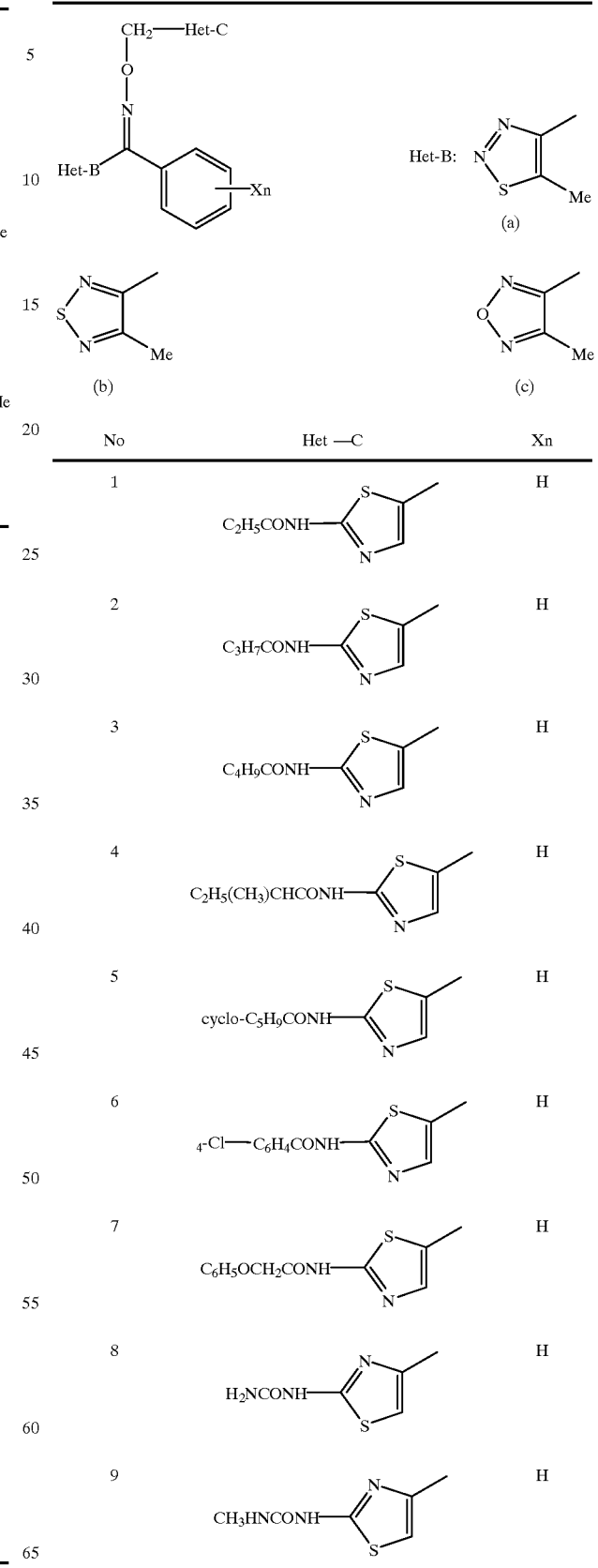

| No | Het—C | Xn |
|---|---|---|
| 1 | C₂H₅CONH-[4-methylthiazol-2-yl] | H |
| 2 | C₃H₇CONH-[4-methylthiazol-2-yl] | H |
| 3 | C₄H₉CONH-[4-methylthiazol-2-yl] | H |
| 4 | C₂H₅(CH₃)CHCONH-[4-methylthiazol-2-yl] | H |
| 5 | cyclo-C₅H₉CONH-[4-methylthiazol-2-yl] | H |
| 6 | 4-Cl—C₆H₄CONH-[4-methylthiazol-2-yl] | H |
| 7 | C₆H₅OCH₂CONH-[4-methylthiazol-2-yl] | H |
| 8 | H₂NCONH-[4-methylthiazol-2-yl] | H |
| 9 | CH₃HNCONH-[4-methylthiazol-2-yl] | H |

TABLE 89-continued

Structure:
CH₂—Het-C, O, N, Het-B, phenyl with Xn substituent

Het-B:
(a) 4-methyl-5-methyl-1,2,3-thiadiazole
(b) 4-methyl-3-methyl-1,2,5-thiadiazole
(c) 4-methyl-3-methyl-1,2,5-oxadiazole (furazan)

| No | Het—C | Xn |
|----|-------|-----|
| 10 | C₂H₅NHCONH-(4-methylthiazol-2-yl) | H |
| 11 | C₃H₇NHCONH-(4-methylthiazol-2-yl) | H |
| 12 | (CH₃)₂NCONH-(4-methylthiazol-2-yl) | H |
| 13 | cyclo-C₆H₁₁NHCONH-(4-methylthiazol-2-yl) | H |
| 14 | C₆H₅NHCONH-(4-methylthiazol-2-yl) | H |
| 15 | (CH₃)₂CHNHCONH-(4-methylthiazol-2-yl) | H |
| 16 | (CH₃)₂CHNHCONH-(4-methylthiazol-2-yl) | H |

TABLE 90

Structure:
CH₂—Het-C, O, N, Het-B, phenyl with Xn substituent

Het-B:
(a) 4-methyl-5-methyl-1,2,3-thiadiazole
(b) 4-methyl-3-methyl-1,2,5-thiadiazole
(c) 4-methyl-3-methyl-1,2,5-oxadiazole (furazan)

| No | Het—C | Xn |
|----|-------|-----|
| 1 | C₆H₅OCH₂CONH-(4-methylthiazol-2-yl) | 3-F |
| 2 | C₆H₅OCH₂CONH-(4-methylthiazol-2-yl) | 4-F |
| 3 | C₆H₅OCH₂CONH-(4-methylthiazol-2-yl) | H |
| 4 | (FCH₂)(CH₃)₂CCONH-(4-methylthiazol-2-yl) | H |
| 5 | (BrCH₂)(CH₃)₂CCONH-(4-methylthiazol-2-yl) | H |
| 6 | (ClCH₂)(CH₃)₂CCONH-(4-methylthiazol-2-yl) | H |
| 7 | (CH₃OCH₂)(CH₃)₂CCONH-(4-methylthiazol-2-yl) | H |
| 8 | (H₂FCOCH₂)(CH₃)₂CCONH-(4-methylthiazol-2-yl) | H |
| 9 | (CH₃SCH₂)(CH₃)₂CCONH-(4-methylthiazol-2-yl) | H |

TABLE 90-continued

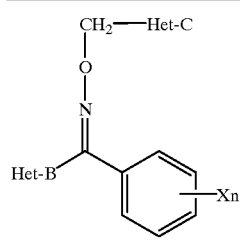
(a) 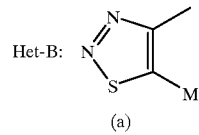
(b) 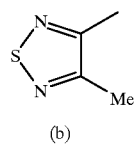
(c) 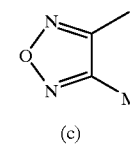

| No | Het—C | Xn |
|---|---|---|
| 10 | (CH$_3$SO$_2$CH$_2$)(CH$_3$)$_2$CCONH— | H |
| 11 | (NCCH$_2$)(CH$_3$)$_2$CCONH— | H |
| 12 | (CH$_3$)$_2$CHCH$_2$OCONH— | H |
| 13 | C$_6$H$_5$OCONH— | H |
| 14 | CH$_2$=C(CH$_3$)OCONH— | H |
| 15 | (CH$_3$)CHCONH— (5-Cl) | H |
| 16 | n-C$_5$H$_{11}$CONH— | H |
| 17 | 3-MeO-C$_6$H$_4$-CONH— | H |
| 18 | 2-CN-C$_6$H$_4$-CONH— | H |

TABLE 90-continued

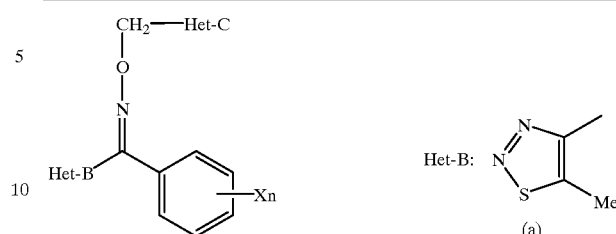
(a) 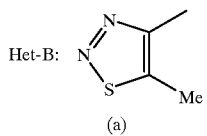
(b) 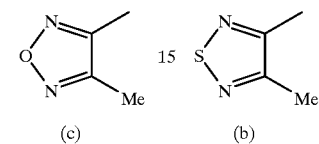
(c) 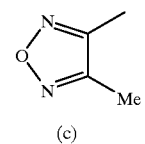

| No | Het—C | Xn |
|---|---|---|
| 19 | MeO-CH=CH-CONH— | H |
| 20 | MeO-C(Me)=CH-CONH— | H |
| 21 | (CH$_3$)$_3$CCONH— (5-Cl) | H |
| 22 | (CH$_3$)$_2$CHCONH— (5-Br) | H |
| 23 | (CH$_3$)$_3$CCONH— (5-Br) | H |
| 24 | (CH$_3$)$_2$CHCONH— (5-CH$_3$) | H |
| 25 | (CH$_3$)$_3$CCONH— (5-CH$_3$) | H |
| 26 | (CH$_3$)$_2$CHCONH— (5-Cl) | 3-F |

Physical chemical data such as $^1$H-NMR spectra and mass spectra of oxime derivatives prepared by the same methods as those shown in Manufacturing Example 1 to 9 are shown in Tables 91 to 97.

TABLE 91

| Compound Table-(a), (b), (c)-No. | E/Z | $^1$H-NMR (CDCl$_3$) δ | MS (m/e, M+) |
|---|---|---|---|
| 4-(c)-2 | Z | 2.32 (s, 3H), 5.41 (s, 2H), 7.12–7.48 (m, 5H), 7.53–7.62 (m, 1H), 7.70 (t, J = 7.69Hz, 1H), 8.59 (d, J = 4.83Hz, 1H). | 328 |
| 4-(c)-3 | Z | 2.32 (s, 3H), 5.40 (s, 2H), 7.11–7.41 (m, 4H), 7.48 (d, J = 8.69Hz, 2H), 7.69 (t, 7.63Hz, 1H), 8.58 (d, J = 4.64Hz, 1H). | 328 |
| 4-(c)-12 | Z | 2.32 (s, 3H), 5.41 (s, 2H), 6.98–7.48 (m, 6H), 7.70 (t, J = 7.63Hz, 1H), 8.59 (d, J = 4.81Hz, 1H). | 312 |
| 4-(c)-13 | Z | 2.33 (s, 3H), 5.40 (s, 2H), 6.98–7.13 (m, 2H), 7.14–7.36 (m, 2H), 7.45–7.63 (m, 2H), 7.69 (t, J = 7.75Hz, 1H), 8.58 (d, J = 4.63Hz, 1H). | 312 |
| 4-(c)-33 | Z | 2.34 (s, 3H), 5.44 (s, 2H), 7.16–7.35 (m, 2H), 7.41–7.58 (m, 1H), 7.61–7.82 (m,3H), 7.87 (s, 1H), 8.60 (d, J = 4,69z, 1H). | 362 |
| 8-(b)-5 | Z | 1.00 (t, J = 7.37Hz, 3H), 1.61–1.90 (m, 2H), 2.28–2.54 (m, 2H), 2.43 (s, 3H), 5.22 (s, 2H), 6.87 (s, 1H), 7.28–7.51 (m, 5H), 8.95–9.23 (brd, 1H). | 401 |
| 8-(b)-6 | Z | 0.39 (t, J = 7.6Hz, 3H), 1.30–1.49 (m, 2H), 1.62–1.79 (m, 2H), 2.42 (t, J = 7.6Hz, 2H), 2.42 (s, 3H), 5.21 (s, 2H), 6.87 (s, 1H), 7.30–7.46 (m, 5H), 9.18–9.36 (brd, 1H). | 415 |
| 8-(b)-11 | Z | 1.07 (s, 9H), 2.30 (s, 2H), 2.40 (s, 3H), 5.21 (s, 2H), 6.87 (s, 1H), 7.25–7.5 (m, 5H), 7.8–8.2 (brd, 1H). | 429 |
| 8-(b)-23 | Z | 1.33 (t, J = 7.09Hz, 3H), 2.39 (s, 3H), 4.28 (q, J = 7.14Hz, 2H), 5.25 (s, 2H), 6.83 (s, 1H), 7.28–7.50 (m, 5H). | 403 |
| 8-(b)-24 | Z | 1.32 (t, J = 6.22Hz, 6H), 2.40 (s, 3H), 4.95–5.19 (m, 1H), 5.24 (s, 2H), 6.81 (s, 1H), 7.30–7.52 (m, 5H). | 417 |
| 13–(b)-2 | Z | 1.28(d, J = 7.0Hz, 6H), 2.43(s, 3H), 2.61(seq, J = 7.0Hz, 1H), 5.22(s, 2H), 6.87(s, 1H), 7.2–7.5(m, 4H), 8.79(brd, 1H). | 435 |
| 13-(b)-22 | Z | 1.28(d, J = 7.0Hz, 6H), 2.33(s, 3H), 2.43(s, 3H), 2.61(seq, J = 7.0Hz, 1H), 5.21(s, 2H), 6.86(s, 1H), 7.15–7.4(m, 4H), 8.78(brd, 1H). | |
| 13-(b)-23 | Z | 1.27(d, J = 7.0Hz, 6H), 2.35(s, 3H), 2.43(s, 3H), 2.61(seq, J = 7.0Hz, 1H), 5.20(s, 2H), 6.86(s, 1H), 7.14(d, J = 8.0Hz, 2H), 7.31 (d, J = 8.0Hz, 2H), 8.80(brd, 1H). | |
| 13-(b)-45 | Z | 1.28(d, J = 6.8Hz, 6H), 2.43(s, 3H), 2.59(seq, J = 6.8Hz, 1H), 5.22(s, 2H), 6.88(s, 1H), 7.20(dd, J = 7.8, 7.8Hz, 1H), 7.29(d, J = 7.8Hz, 1H), 7.52(d, J = 7.8Hz, 1H), 7.66(s, 1H), 8.74(brd, 1H). | 479 |

TABLE 92

| Compound Table-(a), (b), (c)-No. | E/Z | $^1$H-NMR (CDCl$_3$) δ | MS (m/e, M+) |
|---|---|---|---|
| 13-(b)-46 | Z | 1.28(d, J = 6.8Hz, 6H), 2.43(s, 3H), 2.61 (seq, J = 6.8Hz, 1H), 5.21(s, 2H), 6.87(s, 1H), 7.30(m, 2H), 7.48(m, 2H), 8.71(brd, 1H). | 479 |
| 13-(b)-52 | Z | 1.26(d, J = 5.3Hz, 6H), 2.42(s, 3H), 2.58(seq, J = 5.3Hz, 1H), 3.81(s, 3H), 5.18(s, 2H), 6.85(m, 3H), 7.35(m, 2H), 9.11(brd, 1H). | |
| 13-(c)-2 | Z | 1.28 (d,J = 6.88Hz, 6H), 2.28 (s, 3H), 2.45–2.76 (m, 1H), 5.26 (s, 2H), 6.91 (s, 1H), 7.26–7.48 (m, 3H), 7.53–7.69 (m,1H), 8.70–8.91 (brd, 1H). | 419 |
| 13-(c)-3 | Z | 1.28 (d, J = 6.96Hz, 6H), 2.28 (s, 3H), 2.50–2.75 (m, 1H), 5.24 (s, 2H), 6.91 (s, 1H), 7.34 (d, J = 8.67 Hz, 2H), 7.48 (d, J = 8.73Hz, 2H), 8.63–8.85 (brd, 1H). | 419 |
| 13-(c)-12 | Z | 1.28 (d, J = 6.94Hz, 6H), 2.29 (s, 3H), 2.49–2.74 (m, 1H), 5.25 (s, 2H), 6.91 (s, 1H), 7.04–7.45 (m, 4H), 8.78 (s, 1H). | 403 |
| 13-(c)-13 | Z | 1.28 (d, J = 6.94Hz, 6H), 2.29 (s, 3H), 2.48–2.78 (m, 1H), 5.24 (s, 2H), 6.90 (s, 1H), 7.07 (t, J = 8.90 Hz, 2H), 7.45–7.53 (m, 2H), 8.63–8.90 (brd, 1H). | 403 |
| 13-(c)-33 | Z | 1.27 (d, J = 6.93Hz, 6H), 2.29 (s, 3H), 2.47–2.77 (m, 1H), 5.28 (s, 2H), 6.93 (s, 1H), 7.39–7.60 (m, 1H), 7.61–7.78 (m, 2H), 7.68 (s, 1H), 9.20 (s, 1H). | 453 |
| 17-(c)-13 | Z | 1.50–2.10 (m, 8H), 2.29 (s, 3H), 2.70–2.92 (m, 1H), 5.23 (s, 2H), 6.89 (s, 1H), 7.00–7.12 (m, 2H), 7.51–7.62 (m, 2H), 8.71–8.92 (brs, 1H) | 429 |
| 23-(a)-2 | Z | 0.99 (d, J = 6.4Hz, 3H), 2.0–2.4 (m, 1H), 2.47 (s, 3H), 5.25 (s, 2H), 6.90 (s, 1H), 7.25–7.45 (m, 4H), 9.29 (brd, 1H). | 449 |
| 23-(b)-2 | Z | 1.01 (d, J = 6.2Hz, 6H), 2.22(m, 1H), 2.30(d, J = 6.4Hz, 2H), 2.43(s, 3H), 5.22(s, 2H), 6.87(s, 1H), 7.2–7.5(m, 4H), 8.80(brd, 1H). | 449 |
| 23-(b)-12 | Z | 1.00(d, J = 6.4Hz, 6H), 2.1–2.4(m, 3H), 2.41(s, 3h), 5.20(s, 2H), 6.86(s, 1H), 7.0–7.4(m, 4H), 9.94 (brd, 1H). | 433 |
| 23-(b)-45 | Z | 1.01(d, J = 6.6Hz, 6H), 2.21(m, 1H), 2.30(d, J = 6.4Hz, 2H), 2.43(s, 3H), 5.22(s, 2H), 6.87(s, 1H), 7.20(dd, J = 7.9, 7.9Hz, 1H), 7.30(m, 1H), 7.52(m, 1H), 7.66(dd, J = 1.8, 1.8Hz, 1H), 8.89(brd, 1H). | 493 |
| 23-(b)-46 | Z | 1.01(d, J = 6.4Hz, 6H), 2.21 (m, 1H), 2.30(d, J = 6.4Hz, 2H), 2.42(s, 3H), 5.20(s, 2H), 6.86(s, 1H), 7.30(m, 2H), 7.47(m, 2H), 8.76(brd, 1H). | 493 |

TABLE 93

| Compound Table-(a), (b), (c)-No. | E/Z | $^1$H-NMR (CDCl$_3$) δ | MS (m/e, M+) |
|---|---|---|---|
| 23-(c)-2 | Z | 1.01 (d, J = 6.33Hz, 6H), 2.10–2.44 (m, 3H), 2.28 (s, 3H), 5.26 (s, 2H), 6.91 (s, 1H), 7.18–7.48 (m, 3H), 7.61 (s, 1H), 8.95 (s, 1H). | 433 |
| 23-(c)-3 | Z | 0.99 (d, J = 6.43Hz, 6H), 2.13–2.38 (m, 3H), 2.26 (s, 3H), 5.24 (s, 2H), 6.90 (s, 1H), 7.33 (d, J = 8.78Hz, 2H), 7.47 (d, J = 8.71Hz, 2H), 9.30 (s, 1H). | 433 |
| 23-(c)-12 | Z | 0.99 (d, J = 6.36Hz, 6H), 2.08–2.50 (m, 3H), 2.27 (s, 3H), 5.26 (s, 2H), 6.91 (s, 1H), 7.05–7.47 (m, 4H), 9.11–9.38 (brd, 1H). | 417 |
| 23-(c)-13 | Z | 1.00 (d, J = 6,23Hz, 6H), 2.07–2.45 (m, 3H), 2.28 (s, 3H), 5.24 (s, 2H), 6.90 (s, 1H), 6.96–7.18 (m, 2H), 7.42–7.68 (m, 2H), 8.82–9.14 (brd, 1H). | 417 |
| 37-(b)-45 | Z | 2.43(s, 3H), 5.24(s, 2H), 6.94(s, 1H), 7.15–7.35(m, 2H), 7.5–7.7(m, 5H), 7.9–7.95(m, 1H), 9.5(brd, 1H). | 513 |
| 37-(b)-46 | Z | 2.41 (s, 3H), 5.16 (s, 2H), 6.93 (s, 1H), 7.25–7.35 (m, 2H), 7.45–7.55 (m, 4H), 7.55–7.70 (m, 1H), 7.90–7.95 (m, 2H), 9.77 (brd, 1H). | 513 |
| 61-(b)-16 | Z | 1.46–2.02 (m, 8H), 2.42 (s, 3H), 2.65–2.91 (m,1H), 5.21 (s, 2H), 6.86 (s, 1H), 7.28–7.53 (m, 5H), 9.03–9.28 (brd, 1H). | 427 |
| 61-(b)-20 | Z | 2.41 (s, 3H), 5.16 (s, 2H), 6.94 (s, 1H), 7.28–7.48 (m, 5H), 7.49 (d, J = 8.63Hz, 2H), 7.91 (d, J = 8.59Hz, 2H). | 469 |
| 61-(b)-21 | Z | 2.44 (s, 3H), 5.23 (s, 2H), 6.95 (s, 1H), 7.30–7.66 (m, 7H), 7.75–7.88 (m, 1H), 7.98 (s, 1H). | 471 (M+ + 1) |
| 61-(b)-22 | Z | 2.45 (s, 3H), 5.21 (s, 2H), 6.95 (s, 1H), 7.31–7.60 (m, 8H), 7.91 (d, J = 6.59Hz,1H). | 469 |
| 61-(b)-23 | Z | 2.44 (s, 3H), 5.21 (s, 2H), 6.96 (s, 1H), 7.30–7.47 (m, 5H), 7.52 (d, J = 1.95Hz, 1H), 7.87(d, J = 8.43Hz, 1H). | 503 |

TABLE 93-continued

| Compound Table-(a), (b), (c)-No. | E/Z | $^1$H-NMR (CDCl$_3$) δ | MS (m/e, M+) |
|---|---|---|---|
| 62-(b)-3 | Z | 2.43 (s, 3H), 5.22 (s, 2H), 6.94 (s, 1H), 7.12–7.28 (m, 2H), 7.30–7.50 (m, 5H), 7.88–8.09 (m, 2H). | 453 |
| 62-(b)-11 | Z | 2.39 (s, 3H), 2.42 (s, 3H), 5.08 (s, 2H), 6.90 (s, 1H), 7.25–7.50 (m, 7H), 7.80 (d, J = 8.23Hz, 2H). | 449 |
| 62-(b)-20 | Z | 2.42 (s, 3H), 5.20 (s, 2H), 6.97 (s, 1H), 7.30–7.53 (m, 5H), 7.79 (d, J = 8.28Hz, 2H), 8.07 (d, J = 8.13Hz, 2H). | 503 |

TABLE 94

| Compound Table-(a), (b), (c)-No. | E/Z | $^1$H-NMR (CDCl$_3$) δ | MS (m/e, M+) |
|---|---|---|---|
| 62-(b)-21 | Z | 2.36 (s, 3H), 5.01 (s, 2H), 6.95 (s, 1H), 7.29–7.47 (m, 5H), 7.63 (t1 J = 7.82Hz, 1H), 7.84 (d, J = 7.83Hz,1H), 8.10 (d, J = 7.92Hz, 1H), 8.23 (s, 1H). | 503 |
| 62-(b)-17 | Z | 2.27 (s, 6H), 2.36 (s, 3H), 4.70 (s, 2H), 6.87 (s, 1H), 7.03 (d, J = 7.77Hz, 2H), 7.10–7.45 (m, 6H). | 464 (M$^+$ + 1) |
| 62-(b)-23 | Z | 2.38 (s, 3H), 3.86 (s, 3H), 5.06 (s, 2H), 6.89 (s, 1H), 6.96 (d, J = 8.93Hz, 2H), 7.30–7.50 (m, 5H), 7.88 (d, J = 8.93Hz, 2H), 10.20–10.70 (brd, 1H). | 465 |
| 62-(b)-24 | Z | 2.46 (s, 3H), 4.09 (s, 3H), 5.27 (s, 2H), 6.91 (s, 1H), 7.06 (d, J = 8.40Hz, 1H), 7.15 (t, J = 7.58Hz, 1H), 7.29–7.50 (m, 5H), 7.56 (t, J = 6.96Hz, 1H), 8.30 (d, J = 7.84Hz, 1H), 11.06 (s, 1H). | 465 |
| 62-(b)-26 | Z | 2.40 (s, 3H), 4.13 (brd, 2H), 5.12 (s, 2H), 6.67 (d, J = 10.0Hz, 2H), 6.87 (s, 1H), 7.28–7.43 (m, 5H), 7.74 (d, J = 10.0Hz, 2H), 9.95–10.36 (brd, 1H). | 450 |
| 63-(b)-5 | Z | 2.39 (s, 3H), 5.11 (s, 2H), 6.97 (s, 1H), 7.29–7.50 (m, 5H), 7.80 (d, J = 8.41Hz, 2H), 8.04 (d, J = 8.40Hz, 2H). | 460 |
| 64-(b)-14 | Z | 2.39 (s, 3H), 3.79 (s, 2H), 5.16 (s, 2H), 6.86 (s, 1H), 7.29–7.50 (m, 10H). | 449 |
| 65-(b)-4 | Z | 1.26 (d, J = 6.50Hz, 6H), 2.41 (s, 3H), 3.22–3.50 (m, 1H), 4.41–4.66 (m, 2H), 5.34 (s, 2H), 7.28–7.60 (m, 5H), 7.83 (s, 1H), 9.20–9.46 (brd, 1H). | 388 (M$^+$ + 1) |
| 88-(b)-2 | Z | 1.32 (s, 9H), 2.43 (s, 3H), 5.22 (s, 2H), 6.87 (s, 1H), 7.2–7.5 (m, 4H), 9.05 (brd, 1H). | 449 |
| 88-(b)-3 | Z | 1.32 (s, 9H), 2.42 (s, 3H), 5.20 (s, 2H), 6.87 (s, 1H), 7.20–7.45 (m, 4H), 9.35 (brd, 1H). | 449 |
| 88-(c)-3 | Z | 1.33 (s, 9H), 2.29 (s, 3H), 5.25 (s, 2H), 6.91 (s, 1H), 7.35 (d, J = 8.84Hz, 2H), 7.49 (d, J = 8.84Hz, 2H), 8.84 (s,1H). | 433 |
| 88-(b)-12 | Z | 1.32 (s, 9H), 2.42 (s, 3H), 5.21 (s, 2H), 6.88 (s, 1H), 7.0–7.4 (m, 4H), 9.55 (brd, 1H). | 433 |
| 88-(c)-12 | Z | 1.33 (s, 9H), 2.29 (s, 3H), 5.26 (s, 2H), 6.91 (s, 1H), 6.99–7.16 (m, 2H), 7.43–7.69 (m, 2H), 8.72–9.00 (brd, 1H). | 417 |
| 88-(b)-13 | Z | 1.32 (s, 9H), 2.43 (s, 3H), 5.20 (s, 2H), 6.87 (s, 1H), 7.2–7.45 (m, 4H), 9.30 (brd, 1H). | 433 |
| 88-(c)-13 | Z | 1.33 (s, 9H), 2.30 (s, 3H), 5.24 (s, 2H), 6.91 (s, 1H), 6.99–7.16 (m, 2H), 7.43–7.69 (m, 2H), 8.72–9.00 (brd, 1H). | 417 |

TABLE 95

| Compound Table-(a), (b), (c)-No. | E/Z | $^1$H-NMR (CDCl$_3$) δ | MS (m/e, M+) |
|---|---|---|---|
| 88-(b)-22 | Z | 1.32(s, 9H), 2.33(s, 3H), 2.44(s, 3H), 5.22(s, 2H), 6.87(s, 1H), 7.15–7.4(m, 4H), 8.83(brd, 1H). | |
| 88-(b)-23 | Z | 1.32(s, 9H), 2.35 (s, 3H), 2.43(s, 3H), 5.20(s, 2H), 6.86(s, 1H), 7.15(d, J = 8.0Hz, 2H), 7.31 (d, J = 8.0Hz, 2H), 8.86(brd, 1H). | |
| 88-(b)-52 | Z | 1.32(s, 9H), 2.44(s, 3H), 3.81(s, 3H), 5.19(s, 2H), 6.86(m, 3H), 7.36(m, 2H), 8.86(brd, 1H). | |
| 89-(b)-5 | Z | 1.60–2.05 (m, 8H), 2.39 (s, 3H), 2.70–2.97 (m, 1H), 5.30 (s, 2H), 7.30–7.57 (m, 6H). | 428 (M$^+$ + 1) |
| 89-(b)-6 | Z | 2.40 (s, 3H), 5.30 (s, 2H), 7.19 (s, 1H), 7.30–7.60 (m, 7H), 7.93 (d, J = 8.61Hz, 2H). | 470 (M$^+$ + 1) |
| 89-(b)-7 | Z | 2.39 (s, 3H), 4.72 (s, 2H), 5.32 (s, 2H), 6.86–7.14 (m, 3H), 7.24–7.58 (m, 8H). | 466 (M$^+$ + 1) |
| 89-(b)-8 | Z | 2.42 (s, 3H), 5.17 (s, 2H), 5.38–5.83 (brd, 2H), 6.71 (s, 1H), 7.30–7.52 (m, 5H). | 375 (M$^+$ + 1) |
| 89-(b)-12 | Z | 2.42 (s, 3H), 3.04 (s, 6H), 5.18 (s, 2H), 6.77 (s, 1H), 7.28–7.52 (m, 5H). | 403 (M$^+$ + 1) |
| 89-(b)-13 | Z | 1.06–2.01 (m, 10H), 2.41 (s, 3H), 3.53–3.88 (m, 1H), 5.19 (s, 2H), 6.69 (s, 1H), 7.27–7.51 (m, 5H). | 457 (M$^+$ + 1) |
| 89-(b)-14 | Z | 2.41 (s, 3H), 5.23 (s, 2H), 6.78 (s, 1H), 7.04–7.53 (m, 10H). | 451 (M$^+$ + 1) |
| 89-(b)-15 | Z | 1.20 (d, J = 6.54Hz, 6H), 2.41 (s, 3H), 3.84–4.10 (m, 1H), 5.18 (s, 2H), 6.69 (s, 1h), 7.29–7.52 (m, 5H). | 416 |
| 90-(c)-1 | Z | 2.27 (s, 9H), 4.72 (s, 2H), 5.29 (s, 2H), 6.80–7.40 (m, 10H), 9.80 (s, 1H). | 468 (M$^+$ + 1) |
| 90-(c)-2 | Z | 2.28 (s, 9H), 4.72 (s, 2H), 5.27 (s, 2H), 6.806–7.00 (m, 3H), 7.00–7.15 (m, 3H), 7.28–7.42 (m, 2H), 7.43–7.64 (m, 2H), 9.76 (s, 1H). | 467 |
| 90-(b)-3 | Z | 2.44 (s, 3H), 4.72 (s, 2H), 5.25 (s, 2H), 6.98–7.17 (m, 4H), 7.30–7.54 (m, 7H). | 465 |
| 90-(c)-3 | Z | 2.26 (s, 3H), 4.70 (s, 2H), 5.27 (s, 2H), 6.72–7.69 (m, 10H), 6.95 (s, 1H), 9.86 (s, 1H). | 449 |
| 90-(b)-6 | Z | 1.44 (s, 6H), 2.48 (s, 3H), 3.71 (s, 2H), 5.22 (s, 2H), 6.89 (s, 1H), 7.28–7.56 (m, 5H). | 449 |
| 90-(b)-9 | Z | 1.33 (s, 6H), 2.45 (s, 3H), 2.81 (s, 2H), 5.23 (s, 2H), 6.88 (s, 1H), 7.29–7.52 (m, 5H), 9.20–9.48 (brd, 1H) | 461 |

TABLE 96

| Compound Table-(a), (b), (c)-No. | E/Z | $^1$H-NMR (CDCl$_3$) δ | MS (m/e, M+) |
|---|---|---|---|
| 90-(b)-10 | Z | 1.57(s, 6H), 2.45(s, 3H), 2.95(s, 3H), 3.50(s, 2H), 5.23(s, 2H), 6.90(s, 1H), 7.28–7.52(m, 5H), 9.00–9.23(brd, 1H). | 493 |
| 90-(b)-12 | Z | 0.93 (d, J = 6.48Hz, 6H), 1.96–2.19 (m, 1H), 2.38 (s, 3H), 4.01 (d, J = 6.81Hz, 2H), 5.26 (s, 2H), 6.82 (s, 1H), 7.28–7.51 (m, 5H). | 432 (M$^+$ + 1) |
| 90-(b)-13 | Z | 2.30 (s, 3H), 5.32 (s, 2H), 6.90 (s, 1H), 7.06–7.20 (m, 2H), 7.21–7.48 (m, 8H). | 451 |
| 90-(b)-14 | Z | 1.98 (s, 3H), 2.33 (s, 3H), 4.77 (d, J = 5.95Hz, 2H), 5.27 (s, 2H), 6.88 (s, 1H), 7.20–7.48 (m, 5H), 11.15–11.55(brd, 1H). | 416 |
| 90-(b)-15 | Z | 1.27(d, J = 6.9Hz, 6H), 2.44(s, 3H), 2.60(seq, J = 6.9Hz, 1H), 5.18(s, 2H), 7.25–7.45(m, 5H), 8.68(brd, 1H). | |
| 90-(b)-16 | Z | 0.79–1.01 (m, 3H), 1.28–1.45 (m, 2H), 1.70–1.86 (m, 2H), 2.30–2.55 (m, 2H), 2.43 (s, 3H), 5.21 (s, brd, 1H). | 429 |

TABLE 96-continued

| Compound Table-(a), (b), (c)- No. | E/Z | $^1$H-NMR (CDCl$_3$) δ | MS (m/e, M+) |
|---|---|---|---|
| 90-(b)-17 | Z | 2.43 (s, 3H), 3.87 (s, 3H), 5.20 (s, 2H), 6.93 (s, 1H), 7.08–7.20 (m, 1H), 7.29–7.54 (m, 8H), 9.56–9.96 (brd, 1H). | 465 |
| 90-(b)-18 | Z | 2.50 (s, 3H), 5.43 (s, 2H), 7.22 (s, 1H), 7.30–7.50 (m, 5H), 7.80–7.89 (m, 2H), 7.98–8.03 (m, 2H). | 460 |

TABLE 97

| Compound Table-(a), (b), (c)- No. | E/Z | $^1$H-NMR (CDCl$_3$) δ | MS (m/e, M+) |
|---|---|---|---|
| 1-(b)-12 | Z | 2.50 (s, 3H), 5.32 (s, 2H), 7.15–7.26 (m, 2H), 7.30–7.50 (m, 5H), 7.64 (t, J = 7.77Hz, 1H). | 345 |
| 1-(c)-12 | Z | 2.35 (s, 3H), 5.36 (s, 2H), 7.12–7.30 (m, 2H), 7.32–7.57 (m, 5H), 7.66 (t, J = 7.80Hz, 1H). | 329 |
| 7-(b)-15 | Z | 2.41 (s, 3H), 5.07 (s, 2H), 7.02 (s, 1H), 7.32–7.53 (m, 5H), 8.93 (s, 2H). | 332 (M$^+$ + 1) |
| 7-(b)-16 | Z | 1.29 (d, J = 6.93Hz, 6H), 2.39 (s, 3H), 2.56–2.77 (m, 1H), 5.30 (s, 2H), 7.31–7.56 (m, 6H). | 402 (M$^+$ + 1) |
| 7-(b)-17 | Z | 1.33 (s, 9H), 2.39 (s, 9H), 5.30 (s, 2H), 7.30–7.55 (m, 6H). | 416 (M$^+$ + 1) |
| 7-(b)-18 | Z | 2.39 (s, 3H), 5.31 (s, 2H), 7.30–7.55 (m, 6H), 8.57 (s, 1H). | 360 (M$^+$ + 1) |
| 90-(b)-19 | Z | 1.92 (dd, J = 1.5, 7.0Hz, 3H), 2.40 (s, 3H), 5.22 (s, 2H), 5.96 (dd, J = 1.5, 15Hz, 1H), 7.11 (dq, J = 15, 7.0Hz, 1H), 7.2–7.5 (m, 5H), 9.5–10.0 (brd, 1H). | 399 |
| 90-(b)-20 | Z | 1.90 (d, J = 1.0Hz, 3H), 2.26 (d, J = 1.0Hz, 3H), 2.41 (s, 3H), 5.23 (s, 2H), 5.69 (t, J = 1.0Hz, 1H), 6.86 (s, 1H), 7.2–7.5 (m, 5H), 10.1 (brd, 1H). | 413 |

Furthermore, test examples of pesticides according to the present invention will be described hereinafter.

TEST EXAMPLE 7

Control Test of a Plant Disease Caused by *Pseudoperonospora cubensis*

A control test was executed by the same method as that shown in Test Example 2. The test result is shown in Table 98.

TABLE 98

| Compound number | Evaluation |
|---|---|
| 4-(c)-12 | A |
| 4-(a)-13 | A |
| 4-(b)-13 | A |
| 4-(c)-13 | A |
| 7-(a)-10 | A |
| 8-(c)-8 | A |
| 8-(c)-10 | A |
| 13-(a)-8 | B |
| 13-(b)-12 | A |
| 13-(c)-13 | A |
| 61-(b)-14 | B |
| 61-(b)-16 | A |
| 61-(b)-20 | A |
| 90-(b)-3 | A |

TEST EXAMPLE 8

Control Test of a Plant Disease Caused by *Pseudoperonospora cubensis* (Leaf disc test)

A control test was executed by the same method as that shown in Test Example 3. The test result is shown in Table 99.

TABLE 99

| Compound number | Evaluation |
|---|---|
| 1-(c)-1 | A |
| 2-(a)-1 | A |
| 4-(c)-3 | B |
| 4-(c)-12 | A |
| 4-(a)-13 | A |
| 4-(b)-13 | A |
| 4-(c)-13 | A |
| 8-(c)-7 | A |
| 8-(c)-8 | A |
| 8-(b)-10 | A |
| 8-(c)-10 | A |
| 8-(b)-24 | A |
| 13-(b)-2 | A |
| 13-(a)-3 | A |
| 13-(a)-8 | A |
| 13-(c)-13 | A |
| 23-(a)-2 | A |
| 61-(b)-16 | A |
| 61-(b)-20 | A |
| 64-(b)-14 | A |
| 64-(b)-22 | A |
| 90-(b)-3 | A |
| 90-(b)-19 | A |

TEST EXAMPLE 9

Control Test of a Plant Disease Caused by *Plasmopara viticola* (Leaf disc test)

A control test was executed by the same method as that shown in Test Example 4. The test result is shown in Table 100.

TABLE 100

| Compound number | Evaluation | Compound number | Evaluation |
|---|---|---|---|
| 1-(b)-9 | B | 13-(c)-12 | B |
| 1-(c)-9 | B | 13-(b)-13 | A |
| 4-(a)-2 | B | 13-(c)-13 | A |
| 4-(c)-2 | B | 13-(b)-22 | B |
| 4-(c)-12 | A | 13-(b)-23 | B |
| 4-(c)-13 | A | 13-(b)-45 | B |
| 4-(c)-33 | B | 23-(a)-2 | A |
| 6-(b)-19 | B | 23-(b)-2 | A |
| 8-(b)-5 | A | 23-(c)-12 | B |
| 8-(c)-7 | A | 23-(c)-13 | B |
| 8-(c)-8 | A | 23-(b)-45 | B |
| 8-(b)-9 | A | 61-(b)-16 | A |
| 8-(c)-10 | A | 61-(b)-20 | A |
| 8-(b)-11 | B | 62-(b)-24 | A |

TABLE 100-continued

| Compound number | Evaluation | Compound number | Evaluation |
|---|---|---|---|
| 8-(b)-17 | B | 63-(b)-5 | A |
| 8-(b)-24 | A | 64-(b)-14 | A |
| 13-(a)-2 | A | 88-(c)-13 | A |
| 13-(b)-2 | A | 88-(b)-22 | A |
| 13-(c)-2 | B | 89-(b)-12 | B |
| 13-(a)-3 | B | 90-(c)-1 | A |
| 13-(b)-3 | A | 90-(c)-2 | B |
| 13-(a)-8 | A | 90-(c)-3 | A |
| 13-(b)-12 | A | 90-(b)-15 | B |

INDUSTRIAL APPLICABILITY

The present invention provides novel oxime derivatives, which do not cause any chemical damage to plants and have sufficient effectiveness against various plant diseases, and also provides pesticides and control agents to remove plant diseases which contain those oxime derivatives as active ingredients.

What is claimed is:

1. An oxime derivative expressed by the following general chemical formula (1),

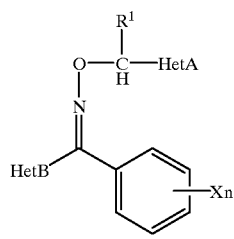

(1)

wherein, $R^1$ represents a hydrogen atom or a lower alkyl group; X represents a halogen atom, a nitro group, a hydroxyl group, a cyano group, a carboxyl group, an alkoxy-carbonyl group, a lower alkyl group which may be substituted with halogen atoms; a lower alkoxy group which may be substituted with halogen atoms; a lower alkylthio group which may be substituted with halogen atoms; a lower alkylsulfonyl group which may be substituted with a halogen atom; an aryl group which may be substituted with a halogen atom or a lower alkyl group; an aryloxy group which may be substituted with a halogen atom or a lower alkyl group; or an amino group which may be substituted with a lower alkyl group; and n represents an integer from 0 to 3; and Het A represents a 6-membered aromatic nitrogen-containing ring which contains one or two nitrogen atoms or its benzo-condensation ring-type nitrogen containing aromatic ring which may be substituted with one or two substitutable groups selected from the group consisting of a halogen atom, a lower alkyl group, a lower alkylthio group, a lower alkylsulfonyl group, a lower alkoxy group, a trifluoromethyl group, and a cyano group; and Het B represents oxime derivatives, each ring structure, expressed by the following formulas,

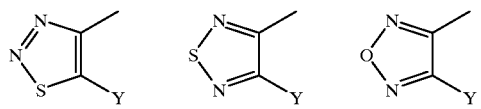

wherein, Y represents a hydrogen atom, a halogen atom, or a lower alkyl group which may be substituted with a halogen atom.

2. An oxime derivative expressed by the following general formula (2)

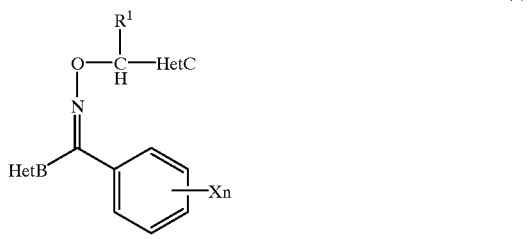

(2)

wherein, $R^1$, X, n, Het B, and Y are the same as those defined in the chemical formula (1), and Het C represents a 5-membered nitrogen containing aromatic ring or its benzo-condensation ring-type nitrogen containing aromatic ring which contains more than one nitrogen atom, or which may contain a sulfur atom or an oxygen atom, and which may be substituted with more than one substituting group, and the substitutable groups on a nitrogen atom of said 5-membered nitrogen containing aromatic ring are groups selected from the group consisting of a lower alkyl group, a lower alkyl-sulfonyl group, triphenylmethyl group, a lower alkoxymethyl group and a N, N-di-substituted sulfamoyl group substituted with lower alkyl groups, and the substitutable groups on a carbon atom of said 5 membered nitrogen containing aromatic ring are groups selected from the group consisting of a halogen atom, a cyano group, an alkyl group ranging from $C_1$ to $C_6$ which may be substituted with a halogen atom, and a cycloalkyl group ranging from $C_3$ to $C_6$; and an alkenyl group ranging from $C_2$ to $C_6$, an alkinyl group ranging from $C_2$ to $C_6$, an alkoxy group ranging from $C_1$ to $C_5$ which may be substituted with a halogen atom, a lower alkylthio group which may be substituted with a halogen atom, a lower alkylsulfonyl group which may be substituted with a halogen atom, a lower alkyl sulfinyl group which may be substituted with halogen atoms, an amino group which may be substituted with a lower alkyl group or a cycloalkyl group ranging from $C_3$ to $C_6$ or a triphenyl-methyl group; and a lower alkoxy-carbonyl group, a carbamoyl group which may be substituted with lower alkyl groups, an aminomethyl group which may be substituted with lower alkyl groups, an acylaminomethyl group, N-alkoxycarbonyl-aminomethyl group, an alkyl thiomethyl group, aryl group which may be substituted with halogen atoms, and a heteroaryl group which may be substituted with halogen atoms, and a group expressed by —N ($R^2$) C (=O) $R^3$ (wherein, $R^2$ represents a hydrogen atom or a methyl group, and $R^3$ represents a hydrogen atom, an alkyl group ranging from $C_1$ to $C_{10}$ which may be substituted with halogen atoms, a cycloalkyl group ranging from $C_3$ to $C_8$, an alkenyl group ranging from $C_2$ to $C_6$, an alkinyl atoms ranging from $C_2$ to $C_4$, an aralkyl group, a lower alkyl group substituted with an amino group, an aralkyl group substituted with an amino group, a lower alkyl group substituted with an acylamino group, an aralkyl group substituted with an acylamino group, a lower alkyl group substituted with an alkoxy-carbonyl-amino group, an aralkyl group substituted with an alkoxy-carbonyl-amino group, an aryl group which may be substituted with halogen atoms, lower alkyl groups which may be substituted with halogen atoms, lower alkoxy groups, lower alkylthio groups, amino groups, nitro groups or cyano groups, a heteroaryl group, a lower alkoxy group, a cycloalkyloxy group ranging from $C_3$ to $C_6$, a benzyloxy group and an aryloxy group).

3. An oxime derivatives according to claim 1, wherein Het A in the general formula (1) is a pyridyl group which may be substituted with a halogen atom or a lower alkyl group.

4. An oxime deivative according to claim 2, wherein Het C in the general formula (2) is expressed by the following formula

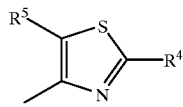

wherein, $R^4$ represents a hydrogen atom, an amino group, an alkoxy group ranging from $C_1$ to $C_5$ which may be substituted with halogen atoms, a lower alkylthio group which may be substituted with halogen atoms, a lower alkylsulfonyl group which may be substituted with halogen atoms, a lower alkylsulfinyl group which may be substituted with halogen atoms; or a —NHC (=O) $R^3$ group (wherein, $R^3$ represents a hydrogen atom, an alkyl group ranging from $C_1$ to $C_{10}$ which may be substituted with halogen atoms, a cycloalkyl group ranging from $C_3$ to $C_8$, an alkenyl group ranging from $C_2$ to $C_6$, an alkinyl group ranging from $C_2$ to $C_4$, an aralkyl group, a lower alkyl group substituted with an amino group, an aralkyl group substituted with an amino group, a lower alkyl group substituted with an acylamino group, an aralkyl group substituted with an acyl-amino group, a lower alkyl group substituted with an alkoxycarbonylamino group, an aralkyl group substituted with an alkoxycarbonylamino group; an aryl group which may be substituted with halogen atoms, lower alkyl groups which may be substituted with halogen atoms, lower alkoxy groups, lower alkylthio groups, amino groups, nitro groups, or cyano groups; a heteroaryl group, a lower alkoxy group, or a cycloalkyloxy group ranging from $C_3$ to $C_6$, a benzyl oxy group, or a aryloxy group); and $R^5$ represents a hydrogen atom, a halogen atom, or a lower alkyl group which may be substituted with a halogen atom.

5. An oxime derivative according to claim 4, wherein $R^4$ is a group expressed by —NHC (=O) $R^3$ (wherein, $R^3$ represents a hydrogen atom, an alkyl group ranging from $C_1$ to $C_6$ which may be substituted with halogen atoms, a lower cycloalkyl group ranging from $C_3$ to $C_6$, an aryl group which may be substituted with halogen atoms, lower alkyl groups which may be substituted with halogen atoms, lower alkoxy groups, amino groups, or cyano groups; a heteroaryl group, or a lower alkoxy group), and $R^5$ is a hydrogen atom.

6. A pesticide containing oxime derivatives according to claims 1 to 5 as active ingredient.

7. A plant disease control agent which contains at least one of the oxime derivatives according to claims 1 to 5 as active ingredient.

8. A plant disease control agent according to claim 7, which is effective for plant diseases caused by mold fungi.

9. A method of manufacturing a hydroxyimino compound expressed by the following general chemical formula (b):

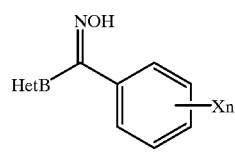

wherein X, n, and Het B are as defined for the following general chemical formula (a), the method comprising the step of reacting an azole-methanone compound expressed by the following general chemical formula (a) with a hydroxylamine:

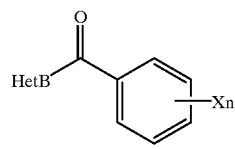

wherein X represents a halogen atom, a nitro group, a hydroxyl group, a cyano group, a carboxyl group, an alkoxy-carbonyl group, a lower alkyl group which may be substituted with halogen atoms; a lower alkoxy group which may be substituted with halogen atoms; a lower alkylthio group which may be substituted with halogen atoms; a lower alkylsulfonyl group which may be substituted with a halogen atom; an aryl group which may be substituted with a halogen atom or a lower alkyl group; an aryloxy group which may be substituted with a halogen atom or a lower alkyl group; or an amino group which may be substituted with a lower alkyl group; and n represents an integer from 0 to 3; and Het B represents oxime derviatives, each ring structure, expressed by the following formulas,

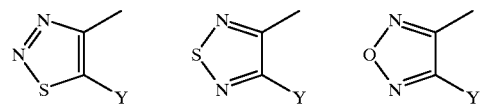

wherein, Y represents a hydrogen atom, a halogen atom, or a lower alkyl group which may be substituted with a halogen atom.

10. A method of manufacturing an oxime derivative expressed by the following general chemical formula (1) or (2):

general chemical formula (1):

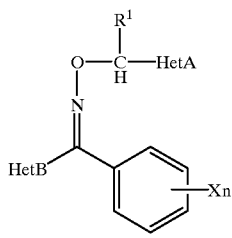

wherein Het B, X, and n are as defined for the following general chemical formula (b), and Het A and $R^1$ are as defined for the following general chemical formula (c)

general chemical formula (2):

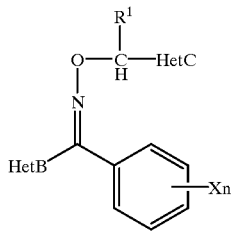

wherein Het B, X, and n are as defined for the following general chemical formula (b), and Het C and $R^1$ are as defined for the following general chemical formula (d), the method comprising the step of reacting a hydroxy-imino compound expressed by the following general chemical formula (b) with a halogen compound expressed by the following general chemical formula (c) or (d) in the presence of a base:

general chemical formula (b):

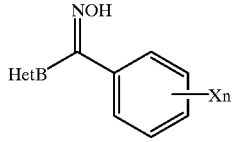

wherein X represents a halogen atom, a nitro group, a hydroxyl group, a cyano group, a carboxyl group, an alkoxy-carbonyl group, a lower alkyl group which may be substituted with halogen atoms; a lower alkoxy group which may be substituted with halogen atoms; a lower alkylthio group which may be substituted with halogen atoms; a lower alkylsulfonyl group which may be substituted with a halogen atom; an aryl group which may be substituted with a halogen atom or a lower alkyl group; an aryloxy group which may be substituted with a halogen atom or a lower alkyl group; or an amino group which may be substituted with a lower alkyl group; and n represents an integer from 0 to 3; and Het B represents oxime derivatives, each ring structure, expressed by the following formulas,

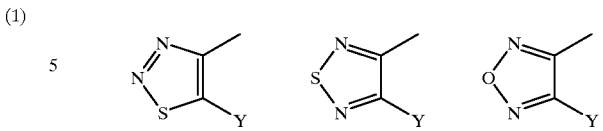

wherein, Y represents a hydrogen atom, a halogen atom, or a lower alkyl group which may be substituted with a halogen atom, general chemical formula (c):

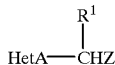

wherein, $R^1$ represents a hydrogen atom or a lower alkyl group; Het A represents a 6-membered aromatic nitrogen-containing ring which contains one or two nitrogen atoms or its benzo-condensation ring-type nitrogen containing aromatic ring which may be substituted with one or two substitutable groups selected from the group consisting of a halogen atom, a lower alkyl group, a lower alkylthio group, a lower alkylsulfonyl group, a lower alkoxy group, a trifluoromethyl group, and a cyano group; and Z represents a chlorine atom, a bromine atom, or an iodine atom, general chemical formula (d)

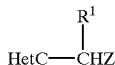

wherein, $R^1$ represents a hydrogen atom or a lower alkyl group;

Het C represents a 5-membered nitrogen containing aromatic ring or its benzo-condensation ring-type nitrogen containing aromatic ring which contains more than one nitrogen atom, or which may contain a sulfur atom or an oxygen atom, and which may be substituted with more than one substituting group, and the substitutable groups on a nitrogen atom of said 5-membered nitrogen containing aromatic ring are groups selected from the group consisting of a lower alkyl group, a lower alkyl-sulfonyl group, triphenylmethyl group, a lower alkoxymethyl group and a N, N-di-substituted sulfamoyl group substituted with lower alkyl groups, and the substitutable groups on a carbon atom of said 5 membered nitrogen containing aromatic ring are groups selected from the group consisting of a halogen atom, a cyano group, an alkyl group ranging from $C_1$ to $C_6$ which may be substituted with a halogen atom, and a cycloalkyl group ranging from $C_3$ to $C_6$; and an alkenyl group ranging from $C_2$ to $C_6$, an alkinyl group ranging from $C_2$ to $C_6$, an alkoxy group ranging from $C_1$ to $C_5$ which may be substituted with a halogen atom, a lower alkylthio group which may be substituted with a halogen atom, a lower alkyl-sulfonyl group which may be substituted with a halogen atom, a lower alkyl sulfinyl group which may be substituted with halogen atoms, an amino group which may be substituted with a lower alkyl group or a cycloalkyl group or a cycloalkyl group ranging from $C_3$ to $C_6$ or a triphenyl-methyl group; and a lower alkoxy-carbonyl group, a carbamoyl group which may be substituted with lower alkyl groups, an aminomethyl group which may be substituted with lower alkyl groups, an acylaminomethyl group, N-alkoxycarbonyl-aminomethyl group, an alkyl thiomethyl group, aryl group which may be substituted with halogen atoms, and a heteroaryl group which may be substituted with halogen atoms, and a group expressed by —N($R^2$) C(=O) $R^3$ (wherein, $R^2$ represents a hydrogen atom or a methyl group, and $R^3$ represents a hydrogen atom, an alkyl group ranging from $C_1$ to $C_{10}$ which may be substituted with halogen atoms, a cycloalkyl group ranging from $C_3$ to $C_8$, an alkenyl group ranging from $C_2$ to $C_6$, an alkinyl group ranging from $C_2$ to $C_4$, an aralkyl group, a lower alkyl group substituted with an amino group, an aralkyl group substituted with an amino group, a lower alkyl group substituted with an acylamino group, an aralkyl group substituted with an acylamino group, a lower alkyl group substituted with an alkoxy-carbonyl-amino group, an aralkyl group substituted with an alkoxy-carbonyl-amino group, an aryl group which may be substituted with halogen atoms, lower alkyl groups which may be substituted with halogen atoms, lower alkoxy groups, lower alkylthio groups, amino groups, nitro groups or cyano groups, a heteroaryl group, a lower alkoxy group, a cycloalkyloxy group ranging from $C_3$ to $C_6$, a benzyloxy group and an aryloxy group); and Z represents a chlorine atom, a bromine atom, or an iodine atom.

11. A hydroxyimino compound of the following general chemical formula (b):

HetB–C(=NOH)–C₆H₄–Xn wherein X represents a halogen atom, a nitro group, a hydroxyl group, a cyano group, a carboxyl group, an alkoxy-carbonyl group, a lower alkyl group which may be substituted with halogen atoms; a lower alkoxy group which may be substituted with halogen atoms; a lower alkylthio group which may be substituted with halogen atoms; a lower alkylsulfonyl group which may be substituted with a halogen atom; an aryl group which may be substituted with a halogen atom or a lower alkyl group; an aryloxy group which may be substituted with a halogen atom or a lower alkyl group; or an amino group which may be substituted with a lower alkyl group; and n represents an integer from 0 to 3; and Het B represents oxime derivatives, each ring structure, expressed by the following formulas,

[three ring structures: thiadiazole, thiadiazole, oxadiazole with Y substituent]

wherein, Y represents a hydrogen atom, a halogen atom, or a lower alkyl group which may be substituted with a halogen atom.

12. A hydroxyimino compound according to claim 11, wherein in the general chemical formula (b), X represents a halogen atom; a lower alkyl group which may be substituted with halogen atoms; a lower alkoxy group which may be substituted with halogen atoms; or an aryl group; and n represents 0 to 3.

13. A hydroxyimino compound according to claim 11, wherein in the general chemical formula (b), X represents a lower alkyl group ranging from $C_1$ to $C_2$, a fluoroalkyl group ranging from $C_1$ to $C_2$, or a halogen atom; and n represents 0 to 3.

14. A hydroxyimino compound according to claim 11, wherein in the general chemical formula (b), n is 0, and Y in Het B is a methyl group.

* * * * *